(12) United States Patent
Turliuc

(10) Patent No.: US 7,963,911 B2
(45) Date of Patent: Jun. 21, 2011

(54) LOCOMOTIVE ENDOSCOPE ASSEMBLY FOR FLUID SUPPLY

(75) Inventor: Gad Turliuc, Raanana (IL)

(73) Assignee: Smart Medical Systems Ltd., Raanana (IL)

( * ) Notice: Subject to any disclaimer, the term of this patent is extended or adjusted under 35 U.S.C. 154(b) by 719 days.

(21) Appl. No.: 11/980,025

(22) Filed: Oct. 30, 2007

(65) Prior Publication Data

US 2008/0064930 A1 Mar. 13, 2008

Related U.S. Application Data

(62) Division of application No. 10/588,131, filed on Apr. 16, 2007.

(60) Provisional application No. 60/542,680, filed on Feb. 9, 2004, provisional application No. 60/559,461, filed on Apr. 6, 2004.

(30) Foreign Application Priority Data

Feb. 7, 2005 (IL) .................... PCT/IL2005/000152

(51) Int. Cl.
*A61B 1/00* (2006.01)
(52) U.S. Cl. .................... 600/115; 600/114; 600/129
(58) Field of Classification Search .......... 600/114–116, 600/104, 127, 129, 139
See application file for complete search history.

(56) References Cited

U.S. PATENT DOCUMENTS

| | | | |
|---|---|---|---|
| 4,040,413 A | 8/1977 | Oshiro | |
| 4,066,070 A | 1/1978 | Utsugi | |
| 4,148,307 A | 4/1979 | Utsugi | |
| 4,176,662 A | 12/1979 | Frazer | |
| 4,195,633 A | 4/1980 | Nehring et al. | |
| 4,195,637 A | 4/1980 | Gruntzig et al. | |
| 4,224,929 A | 9/1980 | Furihata | |
| 4,445,892 A | 5/1984 | Hussein et al. | |
| 4,453,545 A | 6/1984 | Inoue | |
| 4,616,652 A | 10/1986 | Simpson | |
| 4,646,722 A | 3/1987 | Silverstein et al. | |

(Continued)

FOREIGN PATENT DOCUMENTS

WO WO 83/01893 6/1983

(Continued)

OTHER PUBLICATIONS

An English Abstract of JP 2003-250896, Sep. 2003.

(Continued)

*Primary Examiner* — John P Leubecker
*Assistant Examiner* — Victoria W Chen
(74) *Attorney, Agent, or Firm* — Husch Blackwell LLP

(57) ABSTRACT

Apparatus for fluid supply to the interior of a portion of a tubular body portion including a locomotive endoscope head extending along a longitudinal axis and having a first selectably radially extendible sealing element and a second selectably radially extendible sealing element, wherein at least one of the first and second selectably radially extendible sealing elements is axially displaceable with respect to the other, a fluid passageway operative for supplying fluid intermediate the first and second selectably radially extendible sealing elements and a locomotive endoscope head controller controlling the operation of the locomotive endoscope head and being operative for controlling selectable extension of the first and second selectably radially extendible sealing elements, axial displacement of the at least one of the first and second selectably radially extendible sealing elements, and fluid introduction through the fluid passageway.

4 Claims, 39 Drawing Sheets

U.S. PATENT DOCUMENTS

| | | | |
|---|---|---|---|
| 4,646,988 A | 3/1987 | Campbell | |
| 4,676,228 A | 6/1987 | Krasner et al. | |
| 4,690,131 A * | 9/1987 | Lyddy et al. | 600/115 |
| 4,807,593 A | 2/1989 | Ito | |
| 4,862,874 A | 9/1989 | Kellner | |
| 4,983,165 A | 1/1991 | Loiterman | |
| 5,025,778 A | 6/1991 | Silverstein et al. | |
| 5,050,585 A | 9/1991 | Takahashi | |
| 5,135,001 A | 8/1992 | Sinofsky et al. | |
| 5,144,848 A * | 9/1992 | Uenishi et al. | 73/866.5 |
| 5,152,277 A * | 10/1992 | Honda et al. | 600/116 |
| 5,259,366 A | 11/1993 | Reydel et al. | |
| 5,398,670 A * | 3/1995 | Ortiz et al. | 600/114 |
| 5,518,501 A | 5/1996 | Oneda et al. | |
| 5,577,992 A | 11/1996 | Chiba et al. | |
| 5,662,587 A | 9/1997 | Grundfest et al. | |
| 5,679,110 A | 10/1997 | Hamazaki | |
| 5,762,604 A | 6/1998 | Kieturakis | |
| 5,876,329 A | 3/1999 | Harhen | |
| 5,938,586 A | 8/1999 | Wilk et al. | |
| 6,007,482 A | 12/1999 | Madni et al. | |
| 6,161,049 A | 12/2000 | Rudie et al. | |
| 6,162,171 A | 12/2000 | Ng et al. | |
| 6,309,346 B1 | 10/2001 | Farhadi | |
| 6,461,294 B1 | 10/2002 | Oneda et al. | |
| 6,485,409 B1 | 11/2002 | Voloshin et al. | |
| 6,585,639 B1 | 7/2003 | Kotmel et al. | |
| 6,663,589 B1 | 12/2003 | Halevy | |
| 6,702,735 B2 | 3/2004 | Kelly | |
| 6,939,291 B2 * | 9/2005 | Phee Soo Jay et al. | 600/114 |
| 6,951,554 B2 | 10/2005 | Johansen et al. | |
| 6,988,986 B2 * | 1/2006 | Gross | 600/114 |
| 7,056,284 B2 | 6/2006 | Martone et al. | |
| 7,169,105 B2 | 1/2007 | Iwasaka et al. | |
| 7,798,992 B2 * | 9/2010 | Ortiz | 604/95.01 |
| 2002/0143237 A1 | 10/2002 | Oneda et al. | |
| 2002/0156347 A1 | 10/2002 | Kim et al. | |
| 2003/0065250 A1* | 4/2003 | Chiel et al. | 600/115 |
| 2004/0102681 A1 | 5/2004 | Gross | |
| 2005/0038335 A1 | 2/2005 | Gross et al. | |
| 2005/0059931 A1 | 3/2005 | Garrison et al. | |
| 2005/0124856 A1 | 6/2005 | Fujikura et al. | |
| 2005/0125005 A1 | 6/2005 | Fujikura | |
| 2005/0133453 A1 | 6/2005 | Woodruff et al. | |
| 2005/0137457 A1 | 6/2005 | Machida | |
| 2005/0159645 A1 | 7/2005 | Bertolero et al. | |
| 2005/0165233 A1 | 7/2005 | Hamedi et al. | |
| 2005/0165273 A1 | 7/2005 | Takano | |
| 2005/0273021 A1 | 12/2005 | Burgermeister | |
| 2006/0111610 A1 | 5/2006 | Machida | |
| 2006/0161044 A1 | 7/2006 | Oneda et al. | |
| 2006/0241345 A1 | 10/2006 | Oishi et al. | |
| 2007/0244361 A1 | 10/2007 | Ikeda et al. | |

FOREIGN PATENT DOCUMENTS

| | | |
|---|---|---|
| WO | WO 99/53827 | 10/1999 |
| WO | WO 02/064028 | 8/2002 |
| WO | WO 03/080155 | 3/2003 |
| WO | WO 2004/101059 | 11/2004 |

OTHER PUBLICATIONS

Office Action for related Israeli Patent Application dated Mar. 23, 2009.

An Office Action dated Sep. 28, 2009, which issued during the prosecution of Applicant's Australian Patent Application No. 2005211257.

An Office Action dated Oct. 9, 2009, which issued during the prosecution of Applicant's U.S. Appl. No. 10/588,131.

An Office Action dated Apr. 9, 2010, which issued during the prosecution of Applicant's U.S. Appl. No. 10/588,131.

An Office Action dated Nov. 3, 2007, which issued during the prosecution of Applicant's Chinese Patent Application No. 200580004311.4.

An Office Action dated Jan. 25, 2010, which issued during the prosecution of Applicant's Chinese Patent Application No. 200810173921.2.

An International Search Report dated Sep. 1, 2005, which issued during the prosecution of Applicant's PCT/IL05/00152.

An International Search Report dated Jun. 2, 2010, which issued during the prosecution of Applicant's PCT/IL09/00940.

An International Search Report dated Sep. 1, 2009, which issued during the prosecution of Applicant's PCT/IL09/00322.

An International Search Report dated Jul. 9, 2009, which issued during the prosecution of Applicant's PCT/IL08/00687.

An International Search Report dated Jul. 18, 2008, which issued during the prosecution of Applicant's PCT/IL07/00832.

An International Search Report dated Apr. 21, 2008, which issued during the prosecution of Applicant's PCT/IL05/00849.

An International Search Report dated May 19, 2008, which issued during the prosecution of Applicant's PCT/IL07/00600.

Single Balloon Endoscope product, including SIF-Q 180 enteroscope, ST-SB1 overtube, which interface with balloon pump control OBCU and EVIS EXERA II system video system, all commercially available from Olympus Inc., of 3500 Corporate Parkway Center Valley, PA 18034-0610, USA.

An Office Action dated Sep. 23, 2009, which issued during the prosecution of Applicant's Israel Patent Application No. 177148. (Including a translation of the relevant part).

Sleeve Expander Tool product, manufactured by HellermannTyton of 7930 N. Faulkner Road., Milwaukee, Wisconsin USA, and commercially distributed in the UK by Canford Audio PLC of Crowther Road, Washington, UK under catalog No. 55-601.

Double Balloon Endoscope product, including EN-450T5 enteroscope, TS-13140 overtube and BS-2 front balloon, which interface with balloon pump control BP-20 and 2200 video system, all commercially available from Fujinon Inc., of 10 High Point Drive, Wayne, New Jersey, USA.

* cited by examiner

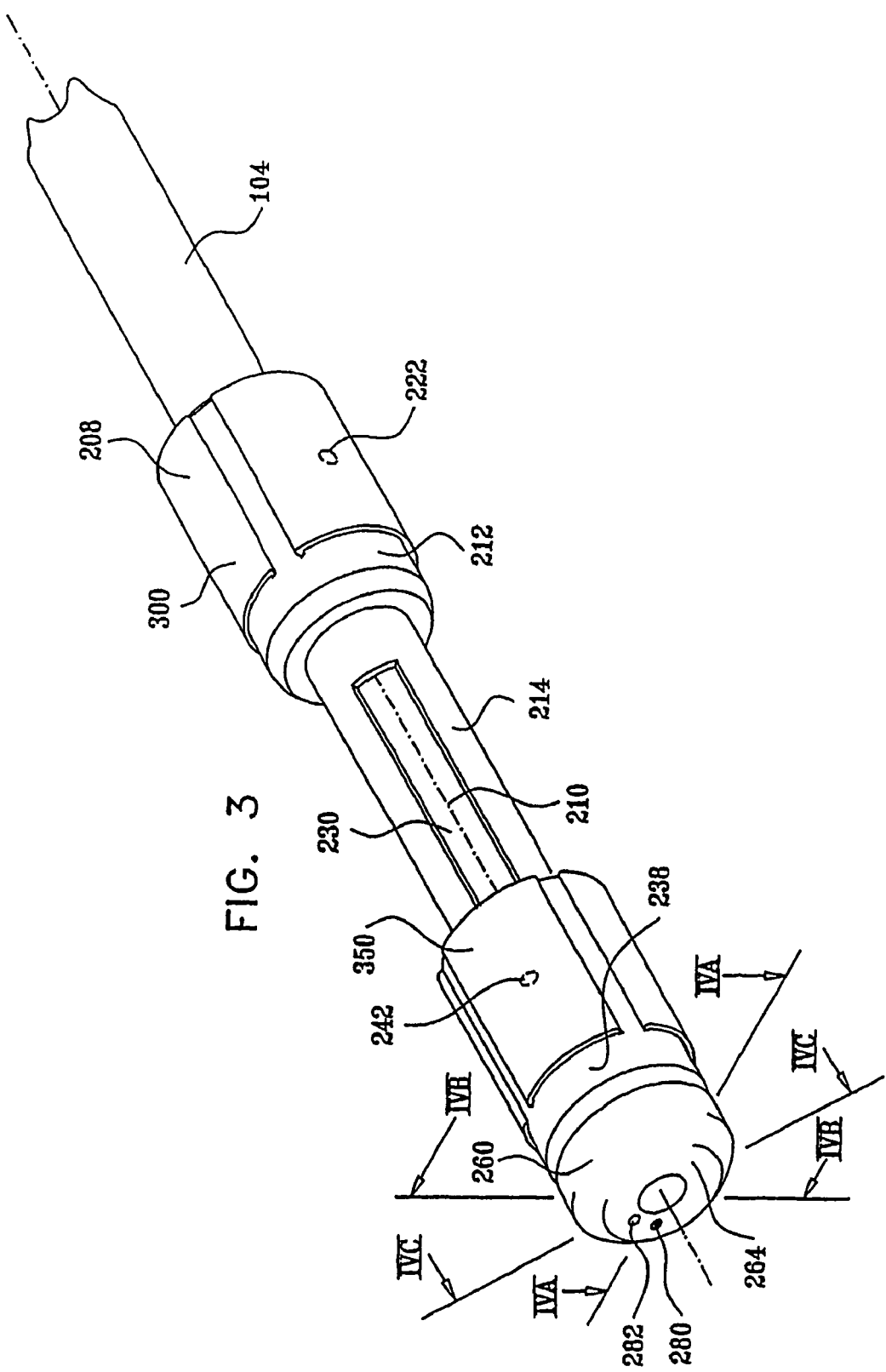

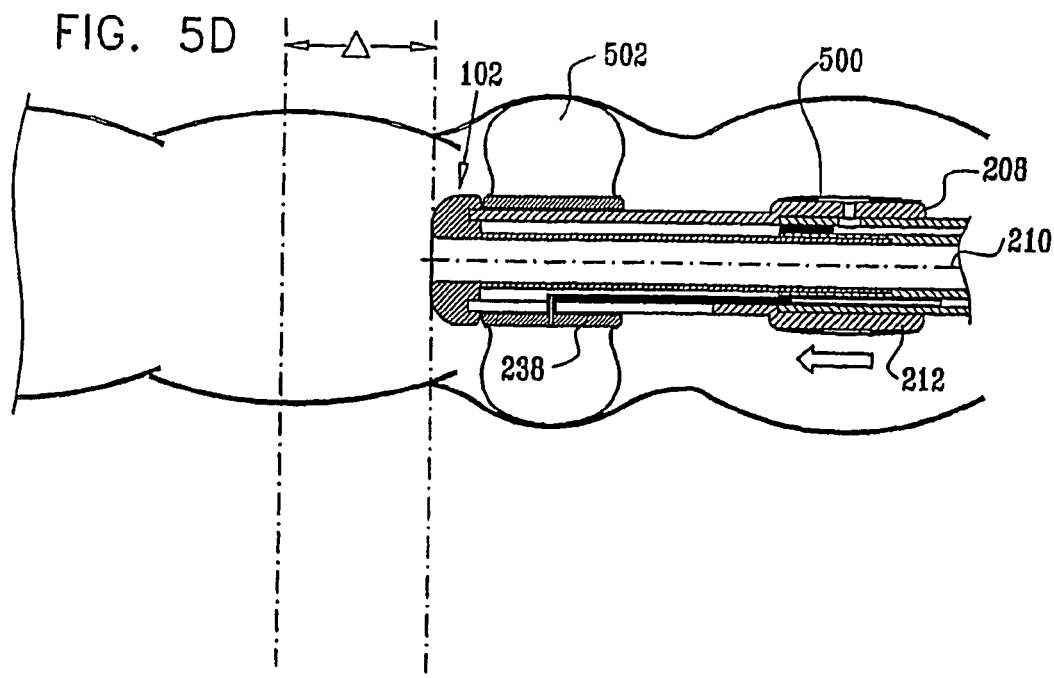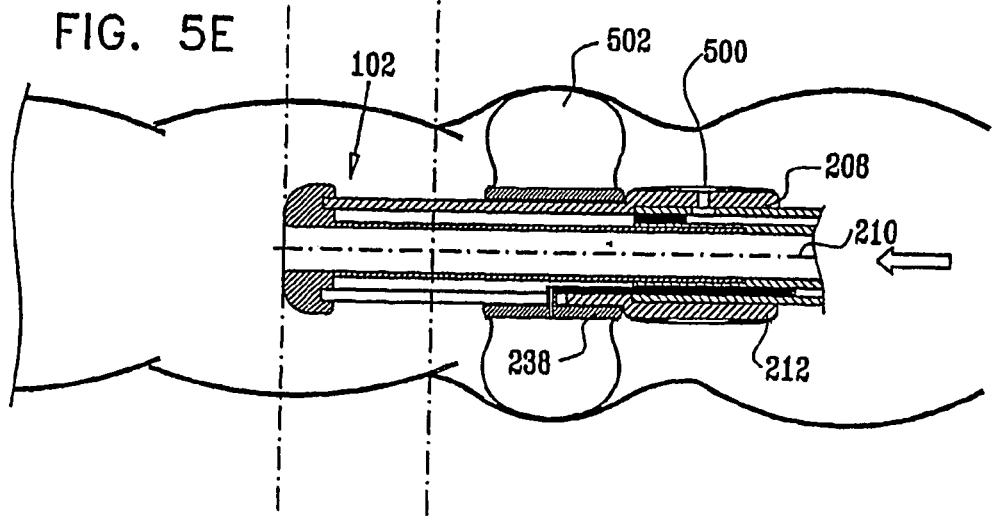

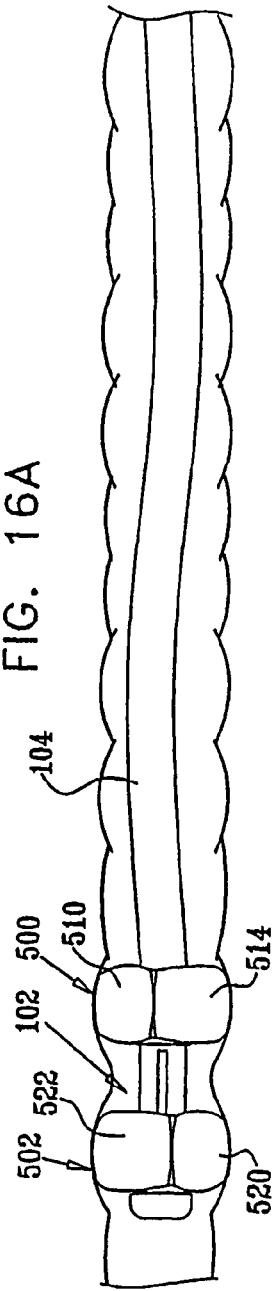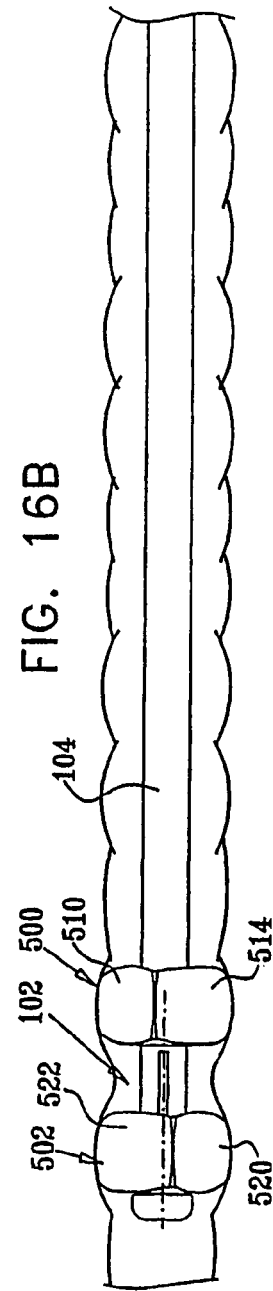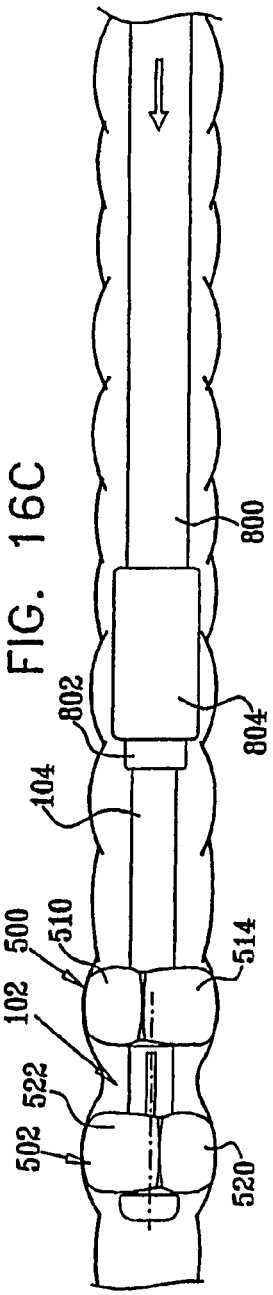

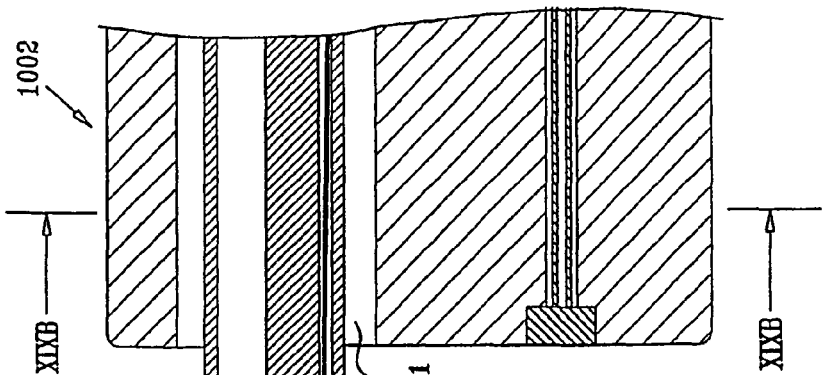
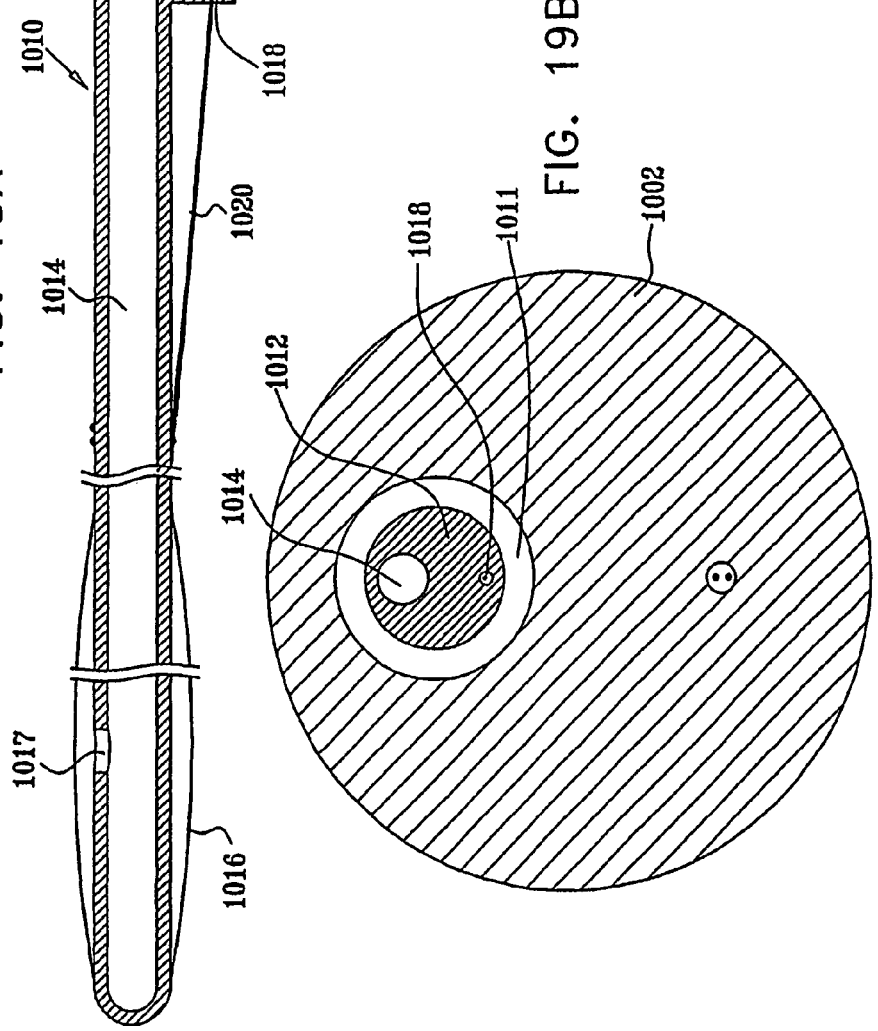

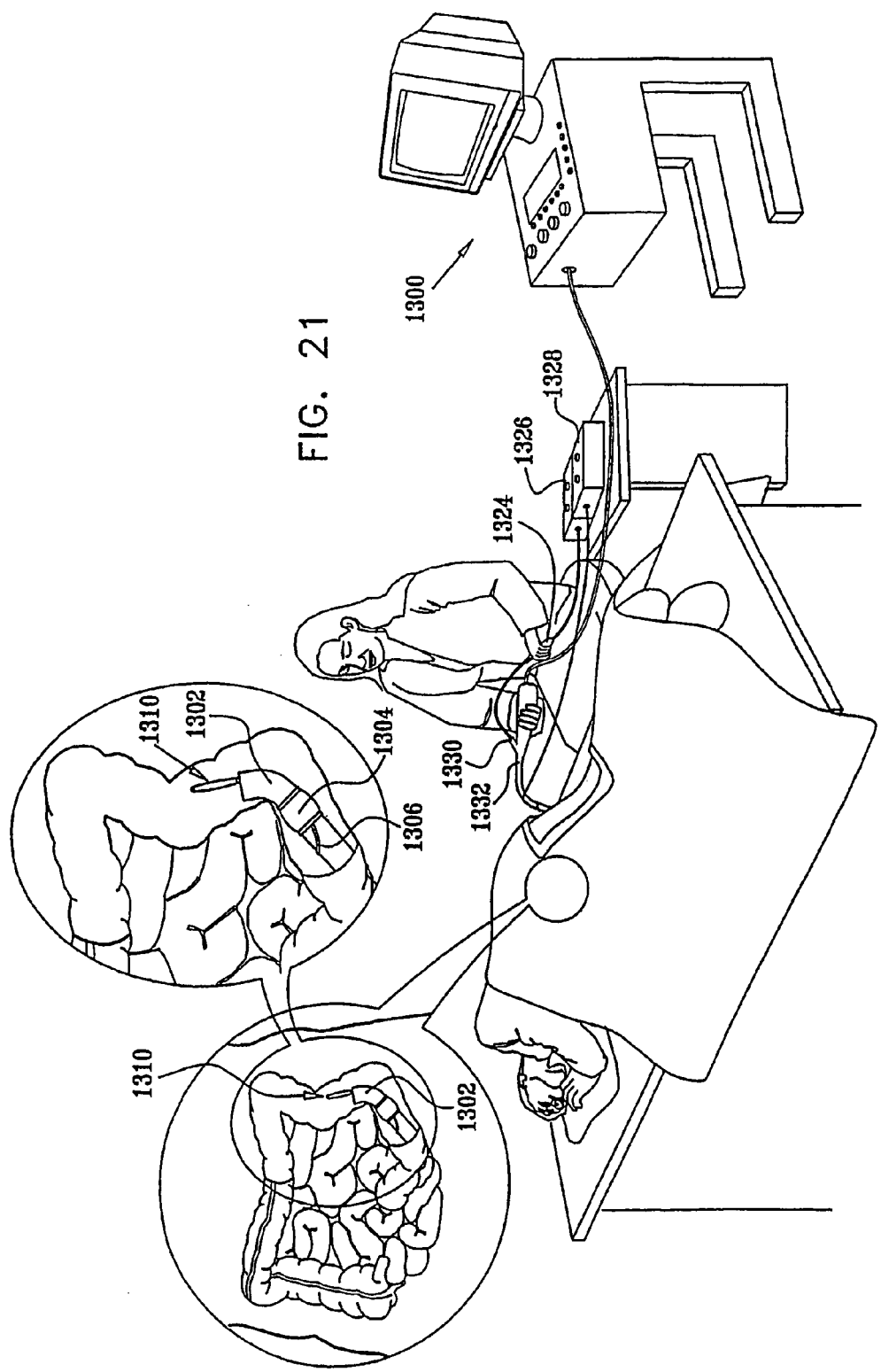

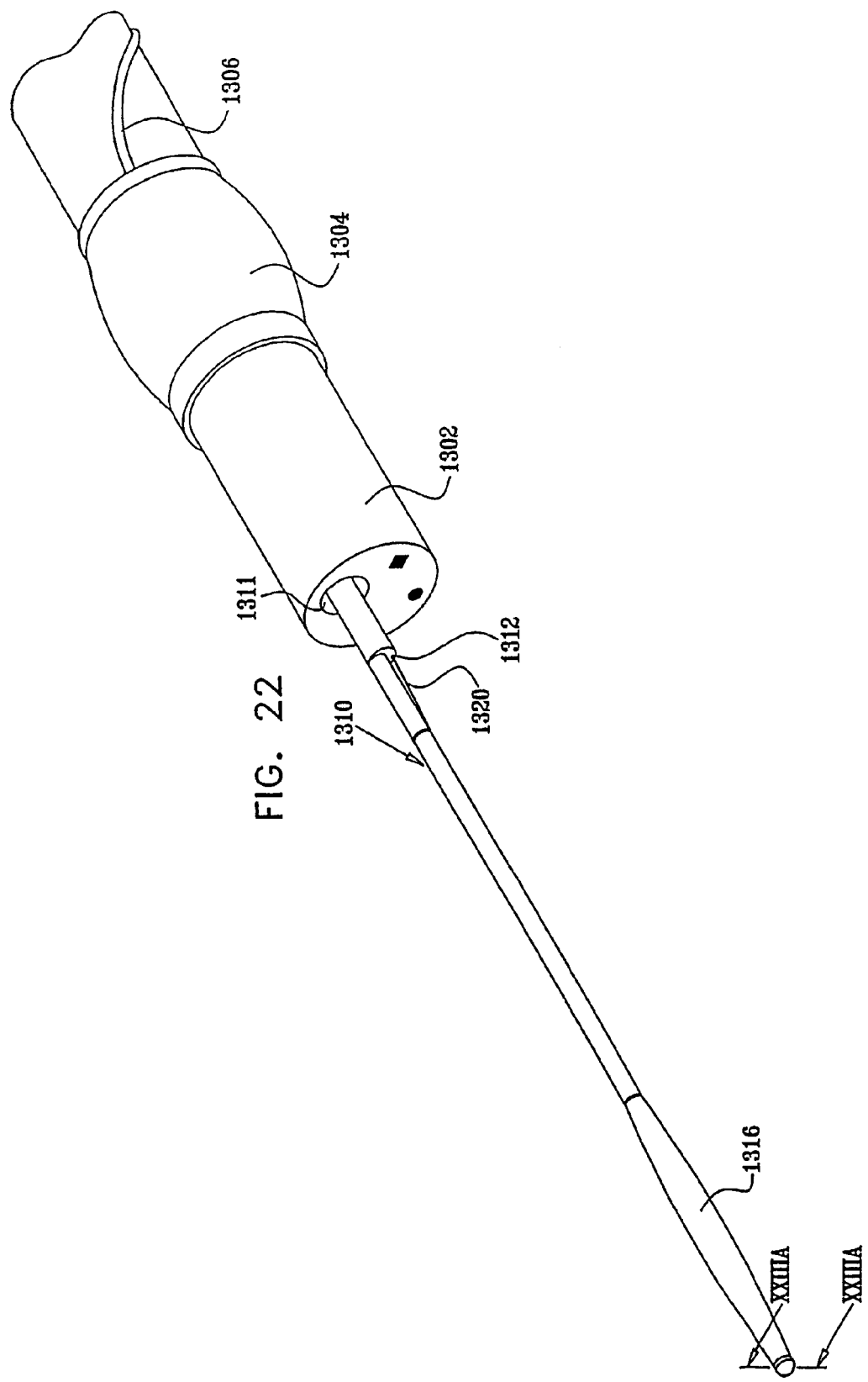

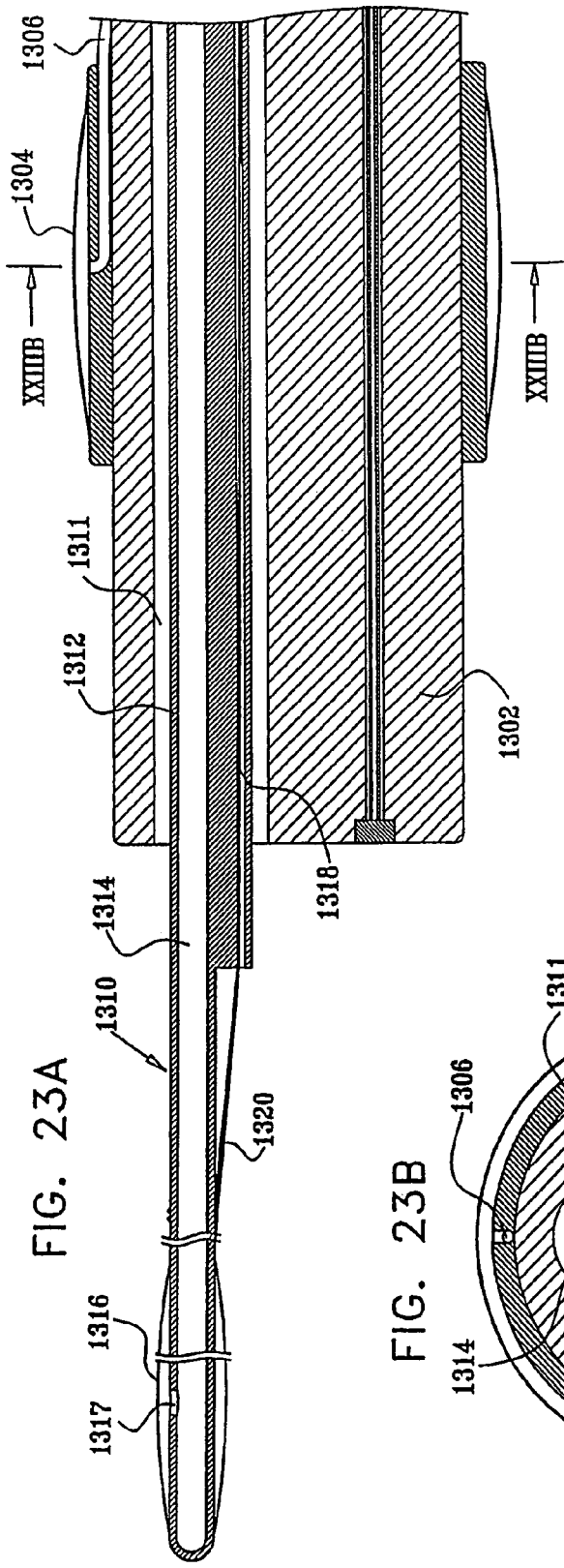

LOCOMOTIVE ENDOSCOPE ASSEMBLY FOR FLUID SUPPLY

REFERENCE TO RELATED APPLICATIONS

This application is a division of U.S. patent application Ser. No. 10/588,131, filed Apr. 16, 2007, which was based on PCT/IL2005/000152 filed Feb. 7, 2005, and priority of which is hereby claimed.

Reference is made to U.S. Provisional Patent Application 60/542,680, filed Feb. 9, 2004 entitled "MICRO-ROBOT AND ACCESSORIES FOR ENDOSCOPY AND IN-PIPE LOCOMOTION" and to U.S. Provisional Patent Application 60/559,461, filed Apr. 6, 2004 entitled "DEVICES, ACCESSORIES AND METHODS FOR ENDOSCOPY AND IN-PIPE PROPAGATION", the disclosures of which are hereby incorporated by reference and priority of which is hereby claimed pursuant to 37 CFR 1.78(a) (4) and (5)(i).

FIELD OF THE INVENTION

The present invention relates to endoscopy generally and more particularly to locomotive endoscopes.

BACKGROUND OF THE INVENTION

The following U.S. patent Documents are believed to represent the current state of the art:
U.S. Pat. Nos. 4,040,413; 4,176,662 and 5,662,587 and
U.S. Patent Application Publication No. 2002/0156347

SUMMARY OF THE INVENTION

The present invention seeks to provide an improved locomotive endoscope.

The terms "endoscope" and "endoscopy" are used herein in a manner somewhat broader than their customary meaning and refer to apparatus and methods which operate within body cavities, passageways and the like, such as, for example, the small intestine, the large intestine, arteries and veins. Although these terms normally refer to visual inspection, as used herein they are not limited to applications which employ visual inspection and refer as well to apparatus, systems and methods which need not necessarily involve visual inspection.

There is thus provided in accordance with a preferred embodiment of the present invention a locomotive endoscope assembly including a locomotive endoscope head, including a main portion extending along a longitudinal axis and having a first selectably inflatable balloon associated therewith and a selectably positionable portion, selectably axially positionable along the main portion and having a second selectably inflatable balloon associated therewith and a locomotive endoscope head controller controlling the operation of the locomotive endoscope head and being operative for controlling positioning of the selectably positionable portion relative to the main portion and selectable inflation of the first and second selectably inflatable balloons.

In accordance with a preferred embodiment of the present invention at least one of the first and second selectably inflatable balloons includes a stretchable balloon. Preferably, the locomotive endoscope assembly also includes an endoscope body associated with the locomotive endoscope head. Optionally and preferably, an instrument channel at least partially extends through the locomotive endoscope head and the endoscope body.

In accordance with another preferred embodiment of the present invention the locomotive endoscope head has a fixed length. Preferably, the endoscope body includes a multi-lumen tube. Alternatively or additionally, the endoscope body interfaces with the locomotive endoscope head controller.

In accordance with yet another preferred embodiment of the present invention the locomotive endoscope assembly also includes an endoscopy system to which the locomotive endoscope head controller is connectable.

In accordance with still another preferred embodiment of the present invention the multi-lumen tube includes at least one lumen operative for at least one of balloon inflation; positioning of the selectably positionable portion of the locomotive endoscope head; passage therethrough of at least one of an optical fiber and an electrical conductor bundle and fluid communication. Preferably, the multi-lumen tube includes at least one lumen operative for each of balloon inflation; positioning of the selectably positionable portion of the locomotive endoscope head and passage therethrough of at least one of an optical fiber and an electrical conductor bundle. Typically and preferably, the at least one lumen includes at least one first lumen operative for inflation of the first selectably inflatable balloon and at least one second lumen operative for inflation of the second selectably inflatable balloon.

In accordance with a further preferred embodiment of the present invention the selectably positionable portion is slidably positionable with respect to the main portion. Preferably, the locomotive endoscope head includes at least one light source and at least one imaging sensor. Additionally or alternatively, the first selectably inflatable balloon includes at least two independently inflatable balloon portions. As a further alternative, the second selectably inflatable balloon includes at least two independently inflatable balloon portions. Preferably, the at least two independently inflatable balloon portions of the second selectably inflatable balloon are azimuthally offset with respect to the at least two independently inflatable balloon portions of the first selectably inflatable balloon.

In accordance with a still further preferred embodiment of the present invention the locomotive endoscope head controller provides locomotive functionality adapted to sequentially displace the locomotive endoscope head through a generally tubular body portion. Preferably, the locomotive functionality includes functionality providing the following sequential operations: inflating the first selectably inflatable balloon, thereby anchoring the first selectably inflatable balloon to an interior surface of the generally tubular body portion; axially repositioning the selectably positionable portion and the second selectably inflatable balloon relative to the first selectably inflatable balloon; inflating the second selectably inflatable balloon, thereby anchoring the second selectably inflatable balloon to an interior surface of the generally tubular body portion; deflating the first selectably inflatable balloon, thereby unanchoring the first selectably inflatable balloon from the interior surface of the generally tubular body portion; and axially repositioning the first selectably inflatable balloon relative to the selectably positionable portion and the second selectably inflatable balloon. Optionally, the first selectably inflatable balloon is arranged with respect to the generally tubular body portion to be forward of the second selectably inflatable balloon. Alternatively, the second selectably inflatable balloon is arranged with respect to the generally tubular body portion to be forward of the first selectably inflatable balloon.

There is also provided in accordance with another preferred embodiment of the present invention a locomotive endoscope assembly including a locomotive endoscope head, including a main portion extending along a longitudinal axis and having a first selectably radially extendible element associated therewith and a selectably positionable portion, selectably axially positionable along the main portion and having a second selectably radially extendible element associated therewith and a locomotive endoscope head controller controlling the operation of the locomotive endoscope head and being operative for controlling positioning of the selectably positionable portion relative to the main portion and selectable extension of the first and second selectably radially extendible elements.

In accordance with a preferred embodiment of the present invention at least one of the first and second selectably radially extendible elements includes a selectably inflatable balloon. Preferably, the selectably inflatable balloon includes a stretchable balloon.

In accordance with another preferred embodiment of the present invention the locomotive endoscope assembly also includes an endoscope body associated with the locomotive endoscope head. Preferably, an instrument channel at least partially extends through the locomotive endoscope head and the endoscope body. More preferably the locomotive endoscope head has a fixed length.

In accordance with yet another preferred embodiment of the present invention the endoscope body includes a multi-lumen tube. Preferably, the endoscope body interfaces with the locomotive endoscope head controller. Additionally and preferably, the locomotive endoscope assembly also includes an endoscopy system to which the locomotive endoscope head controller is connectable.

In accordance with still another preferred embodiment of the present invention the multi-lumen tube includes at least one lumen operative for at least one of radially extending element extension; positioning of the selectably positionable portion of the locomotive endoscope head; passage therethrough of at least one of an optical fiber and an electrical conductor bundle; and fluid communication. Preferably, the multi-lumen tube includes at least one lumen operative for each of radially extending element extension; positioning of the selectably positionable portion of the locomotive endoscope head; and passage therethrough of at least one of an optical fiber and an electrical conductor bundle. Typically and preferably, the at least one lumen includes at least one first lumen operative for extension of the first selectably radially extendible element and at least one second lumen operative for extension of the second selectably radially extendible element.

In accordance with a further preferred embodiment of the present invention the selectably positionable portion is slidably positionable with respect to the main portion. Preferably, the locomotive endoscope head includes at least one light source and at least one imaging sensor.

In accordance with yet a further preferred embodiment of the present invention the first selectably radially extendible element includes at least two independently extendible element portions. Additionally or alternatively, the second selectably radially extendible element includes at least two independently extendible element portions. Preferably, the at least two independently extendible element portions of the second selectably radially extendible element are azimuthally offset with respect to the at least two independently extendible element portions of the first selectably radially extendible element.

In accordance with still a further preferred embodiment of the present invention the locomotive endoscope head controller provides locomotive functionality adapted to sequentially displace the locomotive endoscope head through a generally tubular body portion. Preferably, the locomotive functionality includes functionality providing the following sequential operations: extending the first selectably radially extendible element, thereby anchoring the first selectably radially extendible element to an interior surface of the generally tubular body portion; axially repositioning the selectably positionable portion and the second selectably radially extendible element relative to the first selectably radially extendible element; extending the second selectably radially extendible element, thereby anchoring the second selectably radially extendible element to an interior surface of the generally tubular body portion; retracting the first selectably radially extendible element, thereby unanchoring the first selectably radially extendible element from the interior surface of the generally tubular body portion; and axially repositioning the first selectably radially extendible element relative to the selectably positionable portion and the second selectably radially extendible element Optionally, the first selectably radially extendible element is arranged with respect to the generally tubular body portion to be forward of the second selectably radially extendible element Alternatively, the second selectably radially extendible element is arranged with respect to the generally tubular body portion to be forward of the first selectably radially extendible element.

There is further provided in accordance with yet another preferred embodiment of the present invention an endoscope assembly including an endoscope head extending along a longitudinal axis and having a first plurality of selectably inflatable balloons associated therewith at at least one first axial location therealong and a second plurality of selectably inflatable balloons associated therewith at at least one second axial location therealong and an endoscope head controller being operative for controlling selectable inflation of the first and second pluralities of selectably inflatable balloons for selectable positioning of the endoscope head.

In accordance with a preferred embodiment of the present invention the endoscope head controller is operative for controlling selectable inflation of the first and second pluralities of selectably inflatable balloons for selectable parallel off-center orientation of the endoscope head. Preferably, the endoscope head controller is operative for controlling selectable inflation of the first and second pluralities of selectably inflatable balloons for selectable tilted orientation of the endoscope head. Optionally and preferably, at least one of the first and second pluralities of selectably inflatable balloons includes a plurality of balloons distributed generally azimuthally about the endoscope head. More preferably, at least one balloon of the first and second pluralities of selectably inflatable balloons includes a stretchable balloon.

In accordance with another preferred embodiment of the present invention the endoscope head includes a locomotive endoscope head. Preferably, the locomotive endoscope head includes a main portion extending along a longitudinal axis and associated with the first plurality of selectably inflatable balloons, and a selectably positionable portion, selectably axially positionable along the main portion and associated with the second plurality of selectably inflatable balloons.

In accordance with still another preferred embodiment of the present invention the endoscope assembly also includes an endoscope body associated with the endoscope head. Preferably, an instrument channel at least partially extends through the endoscope head and the endoscope body. Optionally and preferably, the endoscope head has a fixed length.

In accordance with a further preferred embodiment of the present invention the endoscope body includes a multi-lumen tube. Additionally or alternatively the endoscope body interfaces with the endoscope head controller. Preferably, the endoscope assembly also includes an endoscopy system to which the endoscope head controller is connectable.

In accordance with yet a further preferred embodiment of the present invention the multi-lumen tube includes at least one lumen operative for at least one of balloon inflation; positioning of the selectably positionable portion of the endoscope head; passage therethrough of at least one of an optical fiber and an electrical conductor bundle; and fluid communication. Preferably, the multi-lumen tube includes at least one lumen operative for each of balloon inflation; positioning of the selectably positionable portion of the endoscope head; and passage therethrough of at least one of an optical fiber and an electrical conductor bundle.

In accordance with a still further preferred embodiment of the present invention the selectably positionable portion is slidably positionable with respect to the main portion. Preferably, the endoscope head includes at least one light source and at least one imaging sensor. Additionally or alternatively, the first plurality of selectably inflatable balloons includes at least two independently inflatable balloon portions. As a further alternative, the second plurality of selectably inflatable balloons includes at least two independently inflatable balloon portions. Preferably, the at least two independently inflatable balloon portions of the second plurality of selectably inflatable balloons are azimuthally offset with respect to the at least two independently inflatable balloon portions of the first plurality of selectably inflatable balloons.

In accordance with an additional preferred embodiment of the present invention the endoscope head controller provides locomotive functionality adapted to sequentially displace the endoscope head through a generally tubular body portion. Preferably, the locomotive functionality includes functionality providing the following sequential operations: inflating at least part of the first plurality of selectably inflatable balloons, thereby anchoring the first plurality of selectably inflatable balloons to an interior surface of the generally tubular body portion; axially repositioning the selectably positionable portion and the second plurality of selectably inflatable balloons relative to the first plurality of selectably inflatable balloons; inflating at least part of the second plurality of selectably inflatable balloons, thereby anchoring the second plurality of selectably inflatable balloons to an interior surface of the generally tubular body portion; deflating the first plurality of selectably inflatable balloons, thereby unanchoring the first plurality of selectably inflatable balloons from the interior surface of the generally tubular body portion; and axially repositioning the first plurality of selectably inflatable balloons relative to the selectably positionable portion and the second plurality of selectably inflatable balloons. Optionally, the first plurality of selectably inflatable balloons is arranged with respect to the generally tubular body portion to be generally forward of the second plurality of selectably inflatable balloons. Alternatively, the second plurality of selectably inflatable balloons is arranged with respect to the generally tubular body portion to be generally forward of the first plurality of selectably inflatable balloons.

There is additionally provided in accordance with still another preferred embodiment of the present invention an endoscope assembly including an endoscope head extending along a longitudinal axis and having a first plurality of selectably radially extendible elements associated therewith at at least one first axial location therealong and a second plurality of selectably radially extendible elements associated therewith at at least one second axial location therealong and an endoscope head controller being operative for controlling selectable extension of the first and second pluralities of selectably radially extendible elements for selectable positioning of the endoscope head.

In accordance with a preferred embodiment of the present invention the endoscope head controller is operative for controlling selectable extension of the first and second pluralities of selectably radially extendible elements for selectable parallel off-center orientation of the endoscope head. Preferably, the endoscope head controller is operative for controlling selectable extension of the first and second pluralities of selectably radially extendible elements for selectable tilted orientation of the endoscope head. Additionally or alternatively, at least one of the first and second pluralities of selectably radially extendible elements includes a plurality of radially extendible elements distributed generally azimuthally about the endoscope head.

In accordance with another preferred embodiment of the present invention the endoscope head includes a locomotive endoscope head Preferably, the locomotive endoscope head includes a main portion extending along a longitudinal axis and associated with the first plurality of selectably radially extendible elements, and a selectably positionable portion, selectably axially positionable along the main portion and associated with the second plurality of selectably radially extendible elements.

In accordance with yet another preferred embodiment of the present invention least one of the first and second pluralities of selectably radially extendible elements includes a plurality of selectably inflatable balloons. Typically and preferably, at least one balloon of the plurality of selectably inflatable balloons includes a stretchable balloon.

In accordance with still another preferred embodiment of the present invention the endoscope assembly also includes an endoscope body associated with the endoscope head. Preferably, an instrument channel at least partially extends through the endoscope head and the endoscope body. Additionally or alternatively, the endoscope head has a fixed length.

In accordance with a further preferred embodiment of the present invention the endoscope body includes a multi-lumen tube. Preferably, the endoscope body interfaces with the endoscope head controller. Additionally or alternatively, the endoscope assembly also includes an endoscopy system to which the endoscope head controller is connectable.

In accordance with a still further preferred embodiment of the present invention the multi-lumen tube includes at least one lumen operative for at least one of: radially extending element extension; positioning of the selectably positionable portion of the endoscope head; passage therethrough of at least one of an optical fiber and an electrical conductor bundle; and fluid communication. Preferably, the multi-lumen tube includes at least one lumen operative for each of: radially extending element extension; positioning of the selectably positionable portion of the endoscope head; and passage therethrough of at least one of an optical fiber and an electrical conductor bundle.

In accordance with an additional preferred embodiment of the present invention the selectably positionable portion is slidably positionable with respect to the main portion. Preferably, the endoscope head includes at least one light source and at least one imaging sensor. Additionally or alternatively, the first plurality of selectably radially extendible elements includes at least two independently selectably radially extendible elements. As a further alternative, the second plurality of selectably radially extendible elements includes at least two independently selectably radially extendible elements. Preferably, the at least two independently selectably radially extendible elements of the second plurality of selectably radially extendible elements are azimuthally offset with respect to the at least two independently selectably radially extendible elements of the first plurality of selectably radially extendible elements.

In accordance with another preferred embodiment of the present invention the endoscope head controller provides locomotive functionality adapted to sequentially displace the endoscope head through a generally tubular body portion. Preferably, the locomotive functionality includes functionality providing the following sequential operations: extending at least part of the first plurality of selectably radially extendible elements, thereby anchoring the first plurality of selectably radially extendible elements to an interior surface of the generally tubular body portion; axially repositioning the selectably positionable portion and the second plurality of selectably radially extendible elements relative to the first plurality of selectably radially extendible elements; extending at least part of the second plurality of selectably radially extendible elements, thereby anchoring the second plurality of selectably radially extendible elements to an interior surface of the generally tubular body portion; retracing the first plurality of selectably radially extendible elements, thereby unanchoring the first plurality of selectably radially extendible elements from the interior surface of the generally tubular body portion; and axially repositioning the first plurality of selectably radially extendible elements relative to the selectably positionable portion and the second plurality of selectably radially extendible elements. Optionally, the first plurality of selectably radially extendible elements is arranged with respect to the generally tubular body portion to be generally forward of the second plurality of selectably radially extendible elements. Alternatively, the second plurality of selectably radially extendible elements is arranged with respect to the generally tubular body portion to be generally forward of the first plurality of selectably radially extendible elements.

There is also provided in accordance with another preferred embodiment of the present invention apparatus for fluid supply to the interior of a portion of a tubular body portion including an element extending along a longitudinal axis and having at least one first selectably extendible tubular body portion sealing element associated therewith at a first axial location therealong and at least one second tubular body portion sealing element associated therewith at a second axial location therealong, a controller for selectably extending the at least one first and second tubular body portion sealing elements within a tubular body portion to define a sealed region therebetween and a fluid supply functionality supplying a fluid to the sealed region.

In accordance with a preferred embodiment of the present invention at least one of the first and second tubular body portion sealing elements includes a selectably inflatable balloon. Preferably, the selectably inflatable balloon includes a stretchable balloon. More preferably, the selectably inflatable balloon includes a plurality of selectably inflatable balloon portions.

In accordance with another preferred embodiment of the present invention the apparatus includes a locomotive endoscope head. Preferably, the apparatus for fluid supply also includes at least one fluid supply reservoir which is operative to supply the fluid to the sealed region. More preferably, the apparatus for fluid supply also includes fluid suction functionality for suctioning fluid from the sealed region.

There is further provided in accordance with a further preferred embodiment of the present invention apparatus for fluid supply to the interior of a portion of a tubular body portion including a multi-lumen tube including at least first, second and third lumens extending therethrough, a forward selectably inflatable balloon in fluid communication with the first lumen, the forward selectably inflatable balloon being operative to seal the tubular body portion when inflated, a rear selectably inflatable balloon in fluid communication with the second lumen, the rear selectably inflatable balloon being operative to seal the tubular body portion when inflated, a fluid supply outlet, located intermediate the forward and rear selectably inflatable balloons, the outlet being in fluid communication with the third lumen and a controller for selectably inflating the first and second selectably inflatable balloons within a tubular body portion to define a sealed region therebetween and for supplying a fluid to the sealed region.

There is additionally provided in accordance with still another preferred embodiment of the present invention an endoscope assembly including an endoscope tube having an instrument channel an endoscope tool arranged to travel along the instrument channel to a utilization location forward of the endoscope tube, the endoscope tool being slidably and sealingly located within the instrument channel and a fluid endoscope tool positioner for selectably pressurizing the instrument channel for providing fluid driven desired positioning of the endoscope tool along the instrument channel.

In accordance with a preferred embodiment of the present invention the endoscope tool includes a piston-defining portion sealingly and slidably engaging the instrument channel.

There is provided in accordance with a preferred embodiment of the present invention an endoscope assembly including a tube having at least one lumen and an endoscope tool arranged to travel through the at least one lumen, the endoscope tool including a stretchable selectably inflatable anchoring balloon.

There is also provided in accordance with another preferred embodiment of the present invention an endoscope assembly including a tube having at least one lumen and an endoscope tool arranged to travel along the at least one lumen to a utilization location forward of the tube, the endoscope tool being selectably bendable forwardly of the tube.

There is additionally provided in accordance with yet another preferred embodiment of the present invention an endoscope assembly including a tube having at least one lumen and an endoscope tool arranged to travel along the at least one lumen, the endoscope tool including a tool head and a multi-lumen tube connected to the tool head.

In accordance with a preferred embodiment of the present invention the tube includes an endoscope tube. Preferably, the at least one lumen includes instrument channel. Additionally or alternatively, the multi-lumen tube includes at least a first lumen for inflation and deflation of the stretchable selectably inflatable anchoring balloon and a second lumen.

In accordance with another preferred embodiment of the present invention the endoscope assembly also includes a tensioning wire which extends through the second lumen and which is operative for selectably bending the endoscope tool forwardly of the tube. Preferably, the endoscope tool is generally more flexible than the tube. Additionally or alternatively, the endoscope assembly also includes an endoscopy system to which the endoscope tube is connectable. As a further alternative, the endoscope assembly also includes an endoscope tool positioning control device and a balloon inflation/deflation control.

In accordance with yet another preferred embodiment of the present invention the endoscope assembly also includes a tool port associated with the tube which is operative for insertion and removal of the endoscope tool.

There is further provided in accordance with a further preferred embodiment of the present invention an endoscope assembly including an endoscope tube, the endoscope tube having a first stretchable selectably inflatable anchoring balloon adjacent a forward end thereof and an endoscope tool arranged to travel relative to the endoscope tube to a utilization location forward of the endoscope tube, the endoscope tool having a second stretchable selectably inflatable anchoring balloon adjacent a forward end thereof.

In accordance with a preferred embodiment of the present invention the endoscope tool is selectably bendable forwardly of the endoscope tube. Optionally and preferably, the endoscope tool includes a tool head and a multi-lumen tube connected to the tool head. Additionally or alternatively, the multi-lumen tube includes at least a first lumen for inflation and deflation of the second stretchable selectably inflatable anchoring balloon and a second lumen.

In accordance with another preferred embodiment of the present invention the endoscope assembly also includes a tensioning wire which extends through the second lumen and which is operative for selectably bending the endoscope tool forwardly of the endoscope tube. Preferably, the endoscope tool is generally more flexible than the endoscope tube. Additionally or alternatively, the endoscope assembly also includes an endoscopy system to which the endoscope tube is connectable. Additionally or alternatively, the endoscope assembly also includes an endoscope tool positioning control device and at least one balloon inflation/deflation control. As a further alternative, the endoscope assembly also includes a tool port associated with the endoscope tube which is operative for insertion and removal of the endoscope tool.

There is yet further provided in accordance with yet another preferred embodiment of the present invention an endoscope assembly including a locomotive endoscope including a locomotive endoscope head and an endoscope body adapted for locomotion through a tubular body portion and for anchoring at a desired location in the tubular body portion and an endoscopy tool adapted for displacement along the endoscope body to a desired tool operation location.

In accordance with a preferred embodiment of the present invention the endoscope assembly also includes at least one selectably radially extendible element associated with the locomotive endoscope head and adapted for anchoring the locomotive endoscope head at a desired location in the tubular body portion. Preferably, the at least one selectably radially extendible element includes a selectably inflatable anchoring balloon. Additionally or alternatively, the locomotive endoscope head includes at least one light source and at least one imaging sensor.

In accordance with another preferred embodiment of the present invention the endoscope assembly also includes an overtube which is slidable along the endoscope body. Preferably, the overtube is associated with the endoscopy tool. Additionally or alternatively, the endoscope body is adapted to function as a guide wire for the overtube.

In accordance with yet another preferred embodiment of the present invention the endoscopy tool includes a therapeutic tool. Alternatively, the endoscopy tool includes a diagnostic tool. As a further alternative, the endoscopy tool includes a surgical tool.

There is also provided in accordance with another preferred embodiment of the present invention a locomotive endoscopy method including providing a locomotive endoscope head, including a main portion extending along a longitudinal axis and having a first selectably radially extendible element associated therewith and a selectably positionable portion, selectably axially positionable along the main portion and having a second selectably radially extendible element associated therewith and providing locomotion of the locomotive endoscope head by selectably positioning the slidable portion relative to the main portion and selectably extending and retracting the first and second selectably radially extendible elements.

In accordance with a preferred embodiment of the present invention at least one of the first and second selectably radially extendible elements includes a selectably inflatable balloon. Preferably, the locomotive endoscopy method also includes positioning the locomotive endoscope head in a selectably non-parallel orientation relative to a tubular body portion by selectably non-identically extending at least two independently radially extendible element portions of the first selectably radially extendible element and at least two independently radially extendible element portions of the second selectably radially extendible element. Additionally or alternatively, the locomotive endoscopy method also includes positioning the locomotive endoscope head in a selectably off-center parallel orientation relative to a tubular body portion by selectably non-identically extending at least two independently radially extendible element portions of the first selectably radially extendible element and at least two independently radially extendible element portions of the second selectably radially extendible element.

In accordance with another preferred embodiment of the present invention providing locomotion includes sequentially displacing the locomotive endoscope head through a generally tubular body portion. Preferably, providing locomotion includes sequentially displacing the locomotive endoscope head through at least one of a large intestine, a small intestine, an artery and a vein. More preferably, the sequentially displacing includes the following sequential operations: extending the first selectably radially extendible element, thereby anchoring the first selectably radially extendible element to an interior surface of the generally tubular body portion; axially repositioning the selectably positionable portion and the second selectably radially extendible element relative to the first selectably radially extendible element; inflating the second selectably radially extendible element, thereby anchoring the second selectably radially extendible element to an interior surface of the generally tubular body portion; deflating the first selectably radially extendible element, thereby unanchoring the first selectably radially extendible element from the interior surface of the generally tubular body portion; and axially repositioning the first selectably radially extendible element relative to the selectably positionable portion and the second selectably radially extendible element.

There is additionally provided in accordance with yet another preferred embodiment of the present invention an endoscope positioning method including providing an endoscope head extending along a longitudinal axis and having a first plurality of selectably radially extendible elements associated therewith at at least a first axial location therealong and a second plurality of selectably radially extendible elements associated therewith at at least a second axial location therealong and selectably positioning the endoscope head by selectable extension of the first and second pluralities of selectably radially extendible elements.

In accordance with a preferred embodiment of the present invention at least one of the first and second pluralities of selectably radially extendible elements includes a plurality of radially extendible elements distributed azimuthally about the endoscope head and the positioning the endoscope head includes selectable extension of individual ones of the plurality of radially extendible elements. Preferably, at least one selectably radially extendable element of the first and second pluralities of selectably radially extendible elements includes an inflatable balloon.

There is further provided in accordance with still another preferred embodiment of the present invention a method for fluid supply to the interior of a portion of a tubular body portion including providing an element extending along a longitudinal axis and having at least one first selectably extendible tubular body portion sealing element associated therewith at a first axial location therealong and at least one second tubular body portion sealing element associated therewith at a second axial location therealong, extending the at least one first and second tubular body portion sealing elements within a tubular body portion to define a sealed region therebetween and supplying a fluid to the sealed region.

In accordance with a preferred embodiment of the present invention the supplying a fluid includes supplying a therapeutic fluid. Alternatively, the supplying a fluid includes supplying a contrast enhancing fluid. As a further alternative, the supplying a fluid includes supplying an antiseptic fluid.

In accordance with another preferred embodiment of the present invention the supplying a fluid includes supplying an acidic solution. Alternatively, the supplying a fluid includes supplying a basic solution.

There is also provided in accordance with a further preferred embodiment of the present invention an endoscopy method including providing an endoscope tube having an instrument channel and an endoscope tool arranged to travel along the instrument channel to a utilization location forward of the endoscope tube, the endoscope tool being slidably and sealingly located within the instrument channel and selectably pressurizing the instrument channel for providing fluid driven desired positioning of the endoscope tool along the instrument channel.

There is additionally provided in accordance with a still further preferred embodiment of the present invention an endoscopy method including providing a tube having at least one lumen and an endoscope tool arranged to travel through the at least one lumen, the endoscope tool including a stretchable selectably inflatable anchoring balloon and anchoring the endoscope tool forward of the tube within a tubular body portion by inflating the anchoring balloon into anchoring engagement with an interior wall of the tubular body portion.

There is also provided in accordance with another preferred embodiment of the present invention an endoscopy method including providing a tube having at least one lumen and an endoscope tool arranged to travel through the at least one lumen, the endoscope tool being selectably bendable forwardly of the tube and selectably bending the endoscope tool forwardly of the tube.

In accordance with a preferred embodiment of the present invention the endoscope tool includes a stretchable selectably inflatable anchoring balloon and the method also includes anchoring the endoscope tool forward of the tube within a tubular body portion by inflating the anchoring balloon into anchoring engagement with an interior wall of the tubular body portion. Preferably, the endoscopy method also includes sliding the tube forwardly along the endoscope tool, thereby employing the endoscope tool as a guide.

In accordance with another preferred embodiment of the present invention the endoscopy method also includes, prior to sliding the tube forwardly, the step of tensioning the endoscope tool. Preferably, the endoscopy method also includes the steps of sequentially repeating at least two of the anchoring, tensioning and sliding steps.

In accordance with yet another preferred embodiment of the present invention the tube includes an endoscope tube. Preferably, the at least one lumen includes an instrument channel.

There is also provided in accordance with a still further preferred embodiment of the present invention an endoscopy method including providing an endoscope tube having a first stretchable selectably inflatable anchoring balloon adjacent a forward end thereof and an endoscope tool having a second stretchable selectably inflatable anchoring balloon adjacent a forward end thereof and positioning the endoscope tool at a utilization location forward of the endoscope tube.

In accordance with a preferred embodiment of the present invention the endoscopy method also includes prior to the positioning, inflating the first selectably inflatable anchoring balloon on the endoscope tube within a tubular body portion for anchoring the endoscope tube to an inner wall of the tubular body portion, subsequent to the positioning, inflating the second selectably inflatable anchoring balloon on the tool forward of the endoscope tube within the tubular body portion for anchoring the endoscope tool to the inner wall of the tubular body portion, thereafter, deflating the first selectably inflatable anchoring balloon and advancing the endoscope tube over the endoscope tool by employing the endoscope tool as a guide.

In accordance with another preferred embodiment of the present invention the endoscopy method also includes bending the endoscope tool when it is forward of the endoscope tube and prior to inflating the second selectably inflatable anchoring balloon. Preferably, the endoscopy method also includes the step of sequentially repeating at least two of the inflating, positioning, deflating and advancing steps.

In accordance with yet another preferred embodiment of the present invention the endoscopy method also includes the step of sequentially repeating at least two of the inflating, positioning, bending, deflating and advancing steps. Preferably, the positioning of the endoscope tool includes passing the endoscope tool through an instrument channel of the endoscope tube.

There is further provided in accordance with another preferred embodiment of the present invention an endoscopy method including providing a locomotive endoscope including a locomotive endoscope head and an endoscope body, providing locomotion of the locomotive endoscope head through a tubular body portion, anchoring the locomotive endoscope head at a desired location in the tubular body portion and displacing an endoscopy tool along the endoscope body to a desired tool operation location.

In accordance with a preferred embodiment of the present invention the endoscopy method also includes tensioning the endoscope body following the anchoring of the locomotive endoscope head and prior to the displacing the endoscopy tool. Preferably, the endoscopy method also includes, prior to the anchoring, the step of detecting the desired location in the tubular body portion by use of at least one light source and at least one imaging sensor associated with the locomotive endoscope head.

In accordance with another preferred embodiment of the present invention the endoscopy method also includes, prior to the displacing the endoscopy tool, the step of detecting the desired tool operation location in the tubular body portion by use of at least one light source and at least one imaging sensor associated with the locomotive endoscope head. Preferably, the displacing the endoscopy tool includes sliding an overtube associated with the endoscopy tool over the endoscope body.

BRIEF DESCRIPTION OF THE DRAWINGS

The present invention will be understood and appreciated more fully from the following detailed description, taken in conjunction with the drawings in which:

FIGS. 2 and 3 are respective simplified exploded and assembled view illustrations of a locomotive endoscope head constructed and operative in accordance with a preferred embodiment of the present invention;

FIGS. 5A, 5B, 5C, 5D, 5E, 5F and 5G are simplified sectional illustrations, taken along lines IVB-IVB in FIG. 3 of the locomotive endoscope head of FIGS. 2-4C at various stages of forward motion through an intestine;

FIGS. 16A, 16B and 16C, are simplified pictorial illustrations of the locomotive endoscope head of FIGS. 1-12B in a guide wire mode of operation.

FIGS. 18, 19A and 19B are respective simplified pictorial and sectional view illustrations of an accessory constructed and operative in accordance with a preferred embodiment of the present invention;

FIGS. 20A, 20B, 20C, 20D, 20E, 20F, 20G, 20H and 20I are simplified illustrations of various functionalities which may be provided by the system of FIG. 17.

FIG. 21 is a simplified pictorial illustration of an endoscopy system constructed and operative in accordance with another preferred embodiment of the present invention;

FIGS. 22, 23A and 23B are respective simplified pictorial and sectional view illustrations of an accessory constructed and operative in accordance with a preferred embodiment of the present invention.

DETAILED DESCRIPTION OF PREFERRED EMBODIMENTS

Figure 1:
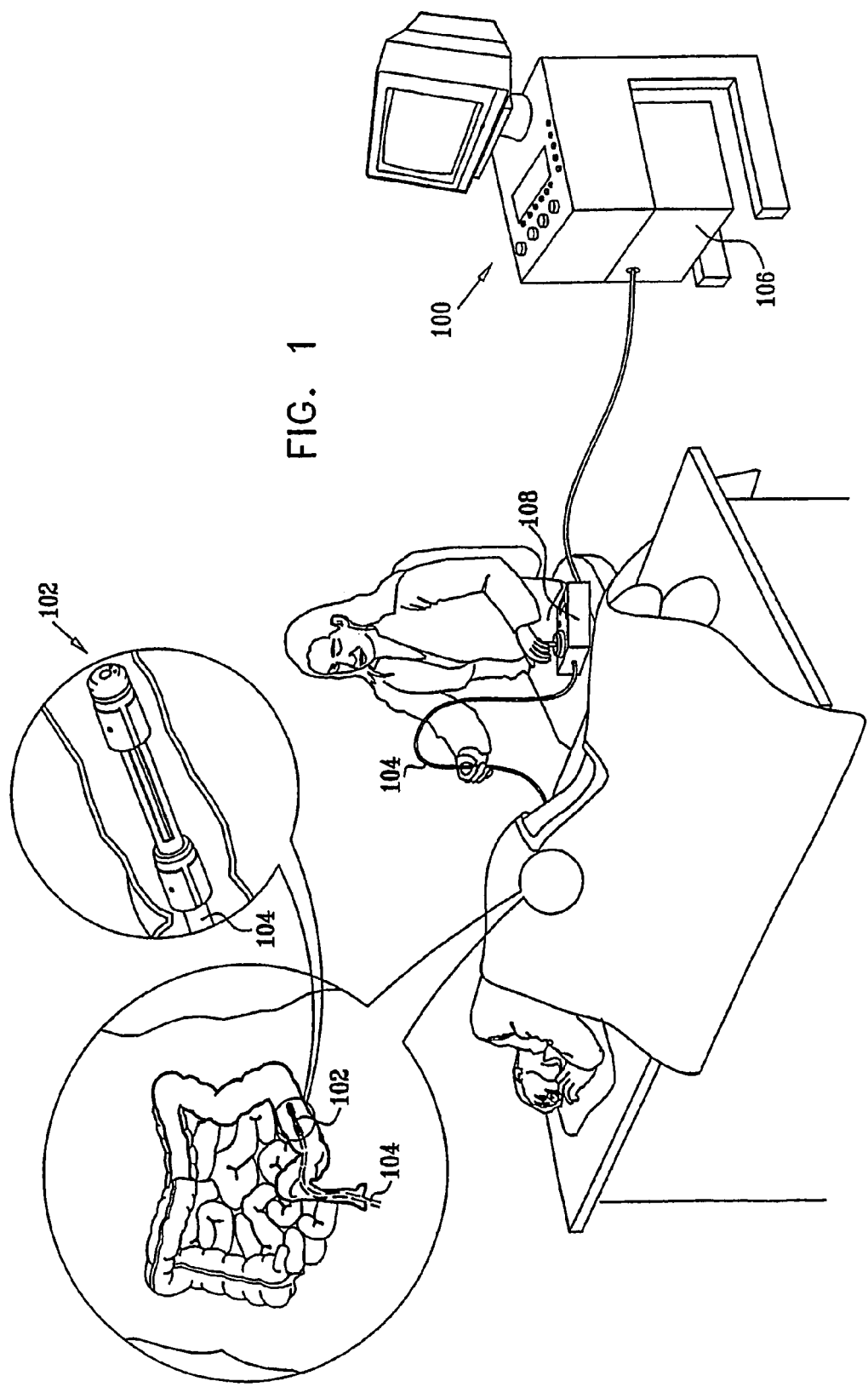
FIG. 1 is a simplified pictorial illustration of an endoscopy system constructed and operative in accordance with a preferred embodiment of the present invention.

Reference is now made to FIG. 1, which is a simplified pictorial illustration of an endoscopy system constructed and operative in accordance with a preferred embodiment of the present invention.

The terms "endoscope" and "endoscopy" are used throughout in a manner somewhat broader than their customary meaning and refer to apparatus and methods which operate within body cavities, passageways and the like, such as, for example, the small intestine, the large intestine, arteries and veins. Although these terms normally refer to visual inspection, as used herein they are not limited to applications which employ visual inspection and refer as well to apparatus, systems and methods which need not necessarily involve visual inspection.

As seen in FIG. 1, a conventional endoscopy system 100, such as a console including a CV-160 video system center, a CLC-160 light source, an OEV-203 video monitor, and an OFP flushing pump, all commercially available from Olympus America Inc. of 2 Corporate Center Drive, Melville, N.Y. 11747, USA, is being employed. A locomotive endoscope head 102, constructed and operative in accordance with a preferred embodiment of the present invention is located within the large intestine of a patient and is coupled to system 100 by a multi-lumen tube 104, also constructed and operative in accordance with a preferred embodiment of the present invention, which interfaces with locomotive head controller 106 and an operator control 108, both of which are also constructed and operative in accordance with a preferred embodiment of the present invention.

Figure 2:
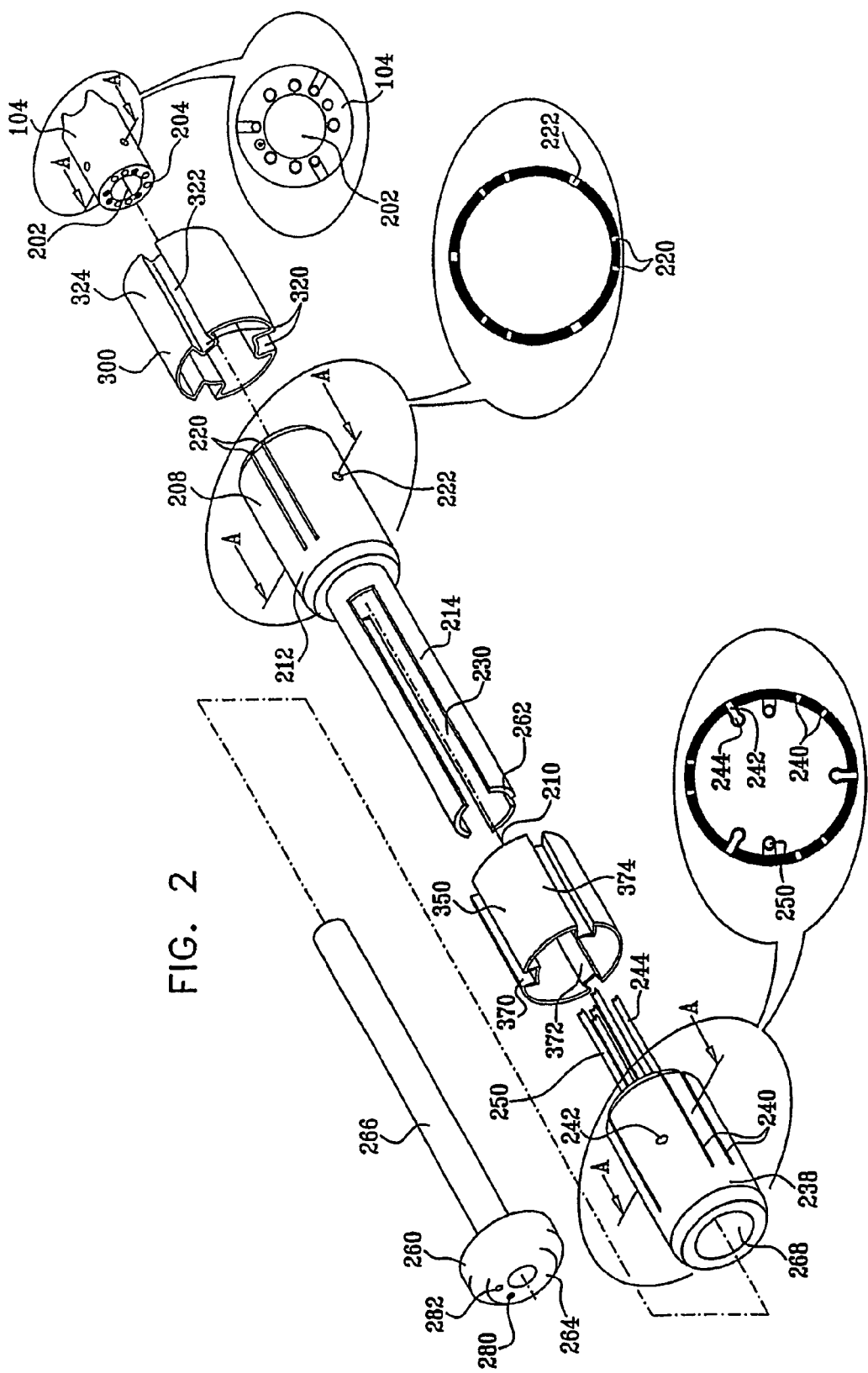
Figure 4A:
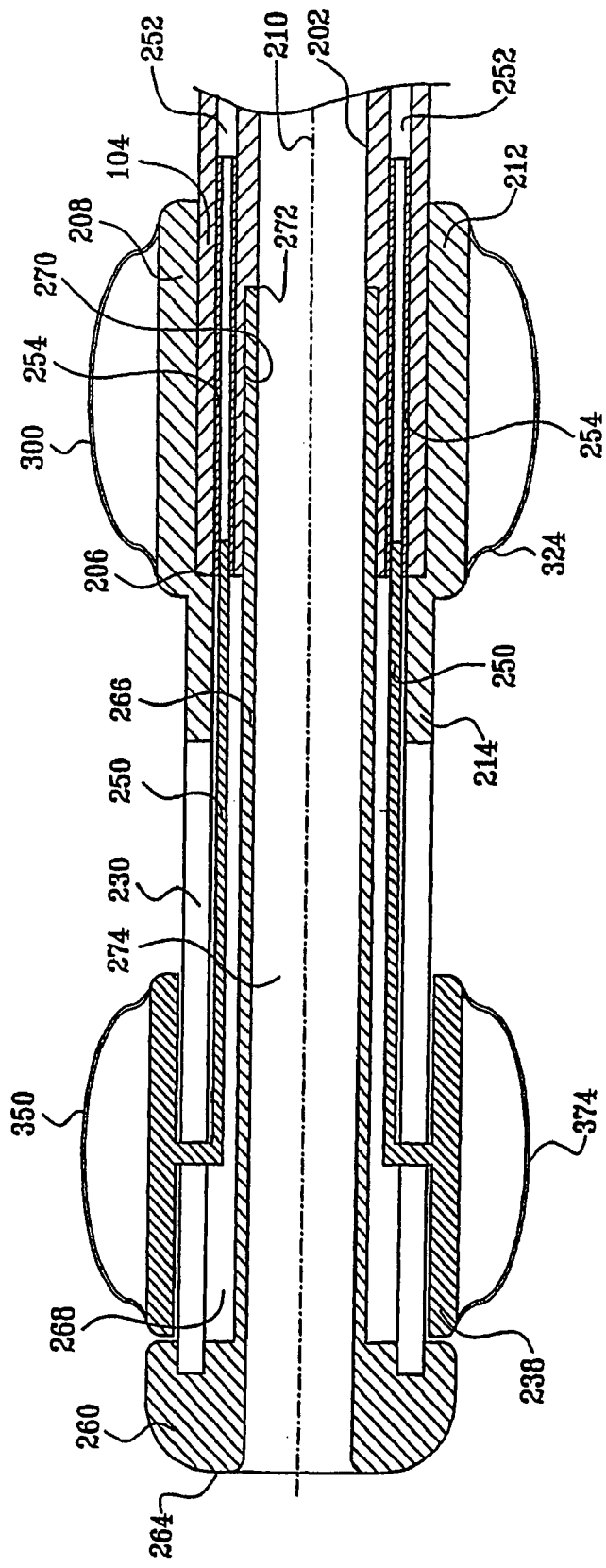
FIGS. 4A, 4B and 4C are simplified sectional illustrations taken along respective lines IVA-IVA, IVB-IVB and IVC-IVC in FIG. 3.
Figure 4B:
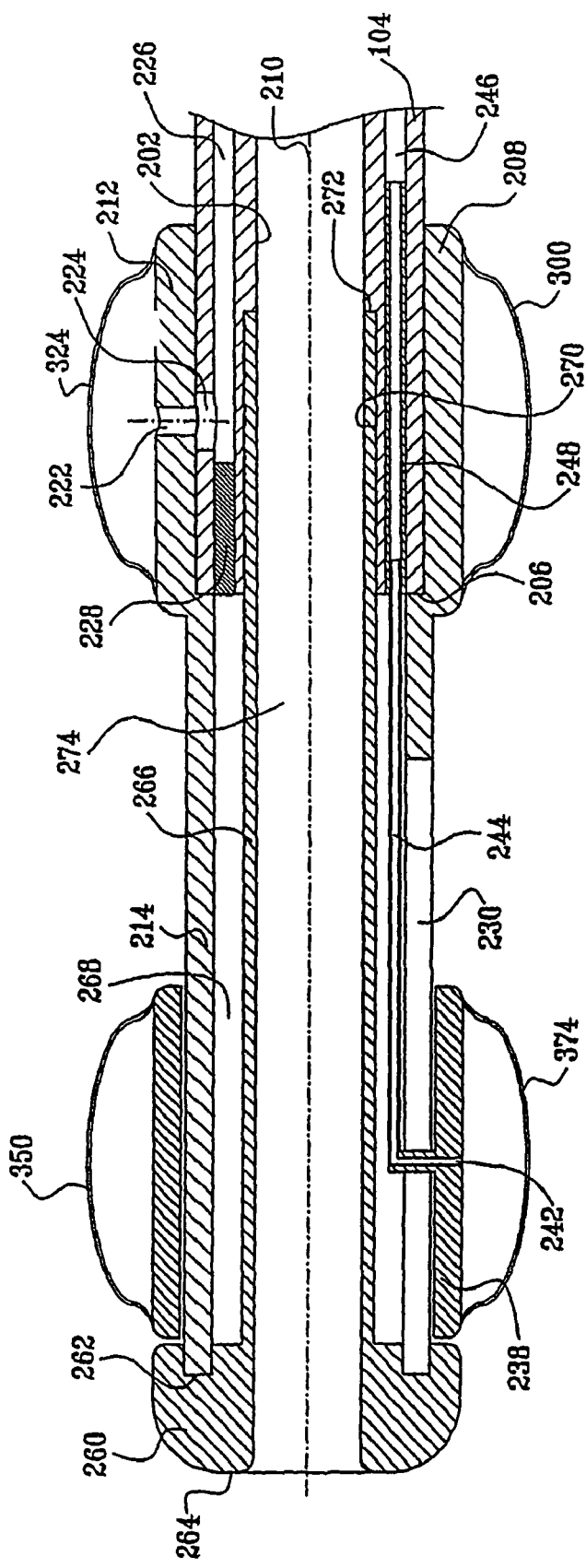
Figure 4C:
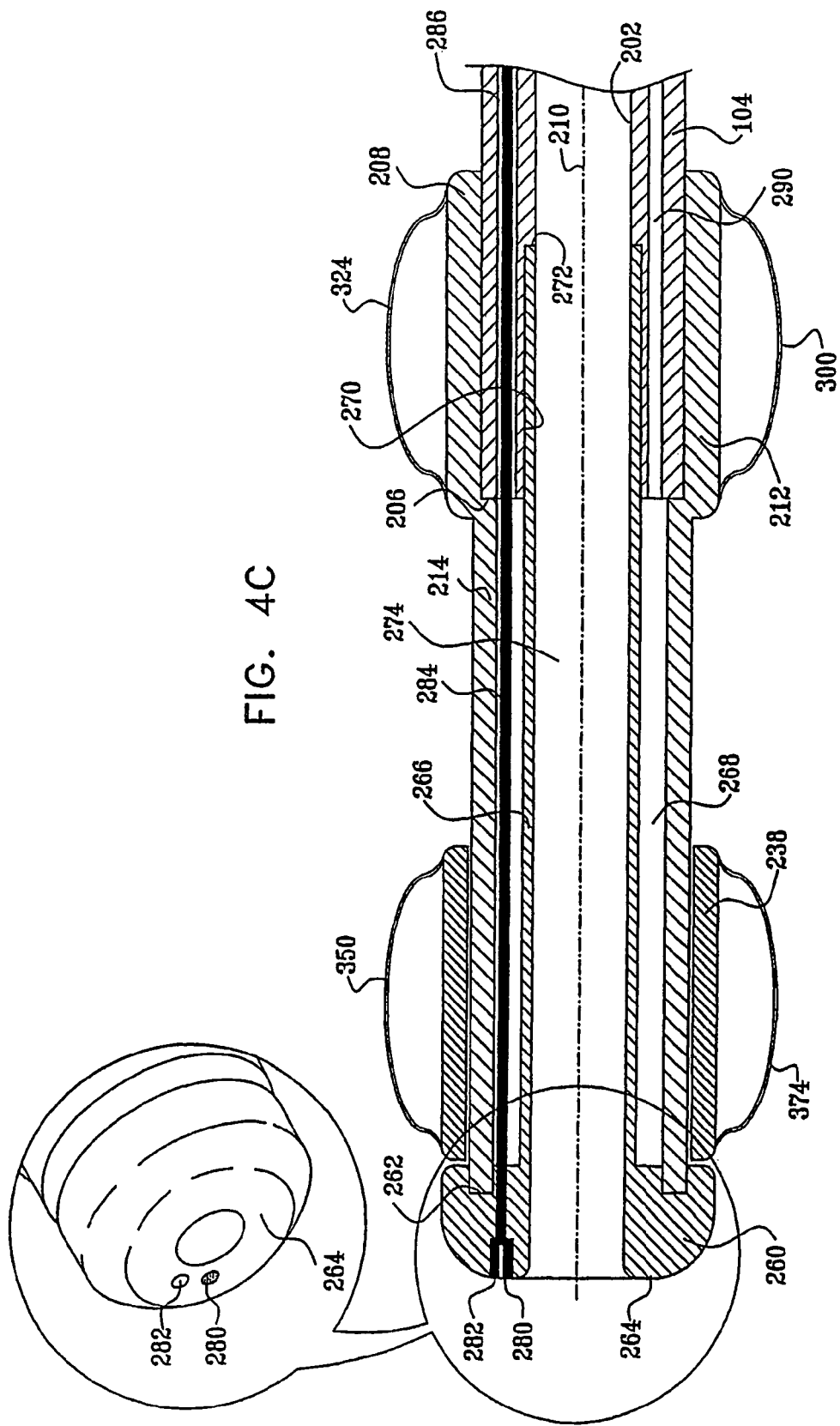

Reference is now made to FIGS. 2 and 3, which are respective simplified exploded and assembled view illustrations of a locomotive endoscope head constructed and operative in accordance with a preferred embodiment of the present invention and to FIGS. 4A, 4B and 4C, which are simplified sectional illustrations taken along respective lines IVA-IVA, IVB-IVB and IVC-IVC in FIG. 3.

As seen in FIGS. 2-4C, a multi-lumen tube 104, having a central passageway 202, defining an instrument channel useful inter alia for tool insertion, inssuflation and suction, and a plurality of peripheral lumens 204, typically ten in number, is seated in a suitably configured recess 206 formed in a housing portion 208. Housing portion 208, which is generally symmetric about a longitudinal axis 210, includes a relatively wider rear portion 212, which defines recess 206 and a relatively narrower main portion 214.

Rear portion 212 is formed with three pairs 220 of axial slits which extend to the rear of rear portion 212 and which are mutually separated along the circumference of rear portion 212 by 120 degrees. Intermediate each pair 220 of axial slits, there is provided an inflation passageway 222, each of which communicates with a corresponding inflation passageway 224 formed in multi-lumen tube 202, which in turn communicates with a respective one of three rear balloon inflation lumens 226, which are included in the nine multiple peripheral lumens 204. Rear balloon inflation lumens 226 are sealed forwardly of inflation passageways 224 by seals 228.

Main portion 214 is formed with three axial slots 230 which extend to the rear of rear portion 212 and which are mutually separated along the circumference of rear portion 212.

A slidable forward balloon support 238 is slidably mounted onto main portion 214 of housing portion 208. Forward balloon support 238 is formed with three pairs 240 of axial slits which extend to the rear of forward balloon support 238 and which are mutually separated along the circumference of forward balloon support 238 by 120 degrees. Intermediate each pair 240 of axial slits, there is provided an inflation passageway 242, each of which communicates with a corresponding inflation passageway 244 which extends rearwardly into slidable sealing engagement with a respective one of three forward balloon inflation lumens 246, which are included in the nine multiple peripheral lumens 204. It is appreciated that inflation passageways 244 are typically relatively rigid and sealingly slide within suitably configured low friction liners 248 which are inserted into forward balloon inflation lumens 246 at the forward end of the multi-lumen tube 104.

A pair of piston rods 250 are fixed to or integrally formed with forward balloon support 238 and extend inwardly and rearwardly thereof into slidable sealing engagement with a respective one of two forward balloon support axial positioning lumens 252, which are included in the ten multiple peripheral lumens 204. It is appreciated that piston rods 250 are typically relatively rigid and sealingly slide within suitably configured low friction liners 254 which are inserted into forward balloon support axial positioning lumens 252 at the forward end of the multi-lumen tube 104.

The relatively rigid inflation passageways 244 and the piston rods 250 are preferably located within axial slots 230.

A front housing portion 260 is fixedly mounted onto a forward end 262 of the main portion 214 of the housing portion 208. Front housing portion includes a cap portion 264 which is fixed to or integrally formed with a cylindrical portion 266 which extends through a central bore 268 of slidable forward balloon support 238. A rearward end of cylindrical portion 266 is seated in a recess 270 and against a shoulder 272 defined in central passageway 202 of multi-lumen tube 104. An interior bore 274 of cylindrical portion 266 defines a continuation of the instrument channel defined by central passageway 202.

At a forward end of cap portion 264 there are preferably provided a light emitting diode 280 and one or more imaging sensors 282. Electrical current is supplied to the light emitting diode 280 and imaging data is received from sensors 282 via an optical fiber and electrical conductor bundle 284 which extends from the forward end of cap portion 264, through a peripheral lumen 286 in multi-lumen tube 104 to locomotive head controller 106 (FIG. 1).

An additional peripheral lumen 290 is provided in multi-lumen tube 104 for fluid communication with the interior of the intestine via slots 230 in housing portion 208. Liquids or pressurized gas may be introduced or drained through this lumen.

An inflatable balloon cylinder 300 is mounted onto rear portion 212 of housing portion 208. As seen clearly in FIG. 2, inflatable balloon cylinder 300 has a uniform cross section which includes three pairs 320 of axial walls which extend along the longitudinal length thereof and engage corresponding axial slits 220 which extend to the rear of rear portion 212. Each pair 320 of axial walls is joined by a circumferential wall portion 322. Axial walls pairs 320 are mutually separated along the circumference of inflatable balloon cylinder 300 by 120 degrees.

Intermediate pairs 320 of axial walls there are defined three inflatable balloon portions 324, each of which separately communicates with a separate inflation passageway 222. Balloon portions 324 are sealed with respect to the rear portion 212 at forward and rearward ends thereof and at slits 220 by adhesive or in any other suitable manner to define three separate and independently controllably inflatable and deflatable balloon portions, distributed about the periphery of rear portion 212. It is appreciated that any suitable smaller or larger number of separate and independently controllably inflatable and deflatable balloon portions may be alternatively employed, although at least three such separate and independently controllably inflatable and deflatable balloon portions are preferred.

An inflatable balloon cylinder 350 is mounted onto forward balloon support 238. As seen clearly in FIG. 2, inflatable balloon cylinder 350 has a uniform cross section which includes three pairs 370 of axial walls which extend along the longitudinal length thereof and engage corresponding axial slits 240 which extend to the rear of forward balloon support 238. Each pair 370 of axial walls is joined by a circumferential wall portion 372. Axial walls pairs 370 are mutually separated along the circumference of inflatable balloon cylinder 350 by 120 degrees.

Intermediate pairs 370 of axial walls there are defined three inflatable balloon portions 374, each of which separately communicates with a separate inflation passageway 242. Balloon portions 374 are sealed with respect to the forward balloon support 238 at forward and rearward ends thereof and at slits 240 by adhesive or in any other suitable manner to define three separate and independently controllably inflatable and deflatable balloon portions, distributed about the periphery of forward balloon support 238. It is appreciated that any suitable smaller or larger number of separate and independently controllably inflatable and deflatable balloon portions may be alternatively employed, although at least three such separate and independently controllably inflatable and deflatable balloon portions which are 60 degrees out of phase with the balloon portions on rear portion 212 are preferred.

It is appreciated that in accordance with a preferred embodiment of the present invention the balloon cylinders 300 and 350 are generally stretchable, and can be stretched to accommodate expansion to a radius up to about 5-20 times greater than the radius of cylinders 300 and 350, when uninflated. Preferably inflation of balloon cylinders 300 and 350 may be achieved using relatively low pressure, such as in the range of 10-50 milibars.

It is appreciated that in accordance with a preferred embodiment of the present invention useful for in vivo inspection of a generally tubular body portion having a variable cross-sectional diameter, the expansion diameter range of balloon cylinders 300 and 350 is larger than the maximum cross-sectional diameter of the generally tubular body portion, thereby ensuring engagement of expanded balloon cylinders 300 and 350 with the interior surface of the generally tubular body portion, and anchoring of the locomotive endoscope head 102 thereto. Preferably, balloon cylinders 300 and 350 are relatively soft, highly compliant balloons, operative to at least partially conform to the shape of the interior surface of the generally tubular body portion when in engagement therewith.

It is appreciated that balloon cylinders 300 and 350 may be formed of well-known stretchable materials such as latex, flexible silicon, or highly flexible nylon. Alternatively, balloon cylinders 300 and 350 may be formed of polyurethane which is less stretchable and conforming than latex, flexible silicon, or highly flexible nylon. Preferably, balloon cylinders 300 and 350 have diameters which are sufficient to ensure tight anchoring at any part of the generally tubular body portion.

Reference is now made to FIGS. 5A, 5B, 5C, 5D, 5E, 5F and 5G, which are simplified sectional illustrations, taken along lines IVB-IVB in FIG. 3, of the locomotive endoscope head of FIGS. 2-4C at various stages of forward motion through an intestine. As seen in FIGS. 5A-5G, locomotion of the locomotive endoscope head 102 of FIGS. 2-4C is achieved by a combination of sequential inflations and deflations of balloons, here respectively designated by reference numerals 500 and 502 mounted onto the housing portion 208 and the forward balloon support 238, combined with relative axial displacement of forward balloon support 238 vis-à-vis housing portion 208. It is appreciated that each of balloons 500 and 502 preferably includes multiple separate and independently controllably inflatable and deflatable balloon portions as described hereinabove.

Figure 5A:
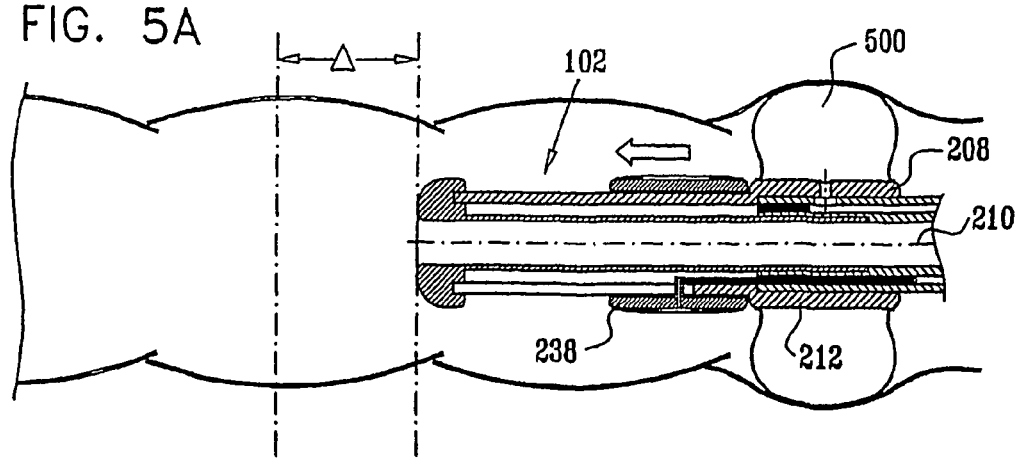

Turning to FIG. 5A, it is seen that balloon 500 is inflated, thus engaging an inner wall of an intestine and fixing the position of the housing portion 208 relative thereto. In this orientation, the forward balloon support 238 is shown in a rearward axial orientation, adjacent rear portion 212. Considering FIG. 5B, it is seen that forward balloon support 238 has moved axially forward relative to housing portion 208, while the housing portion 208 remains axially fixed relative to the intestine.

Figure 5B:
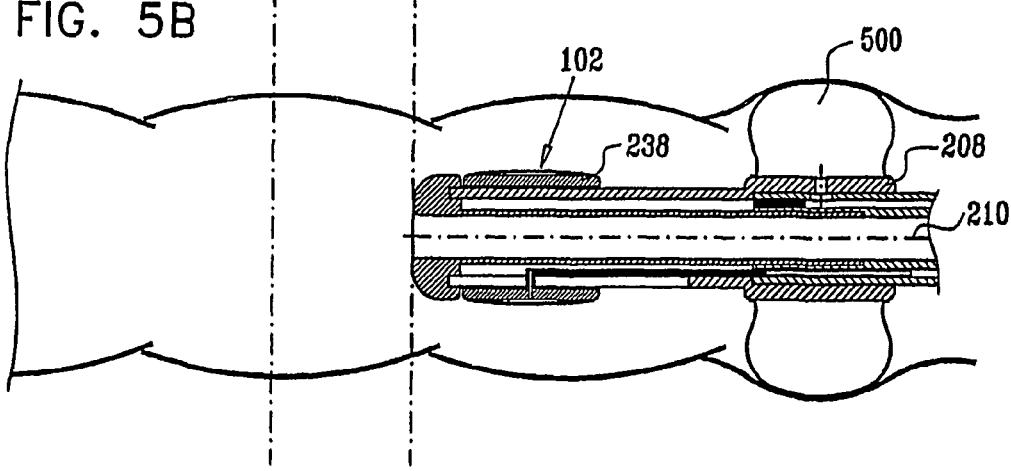
Figure 5C:
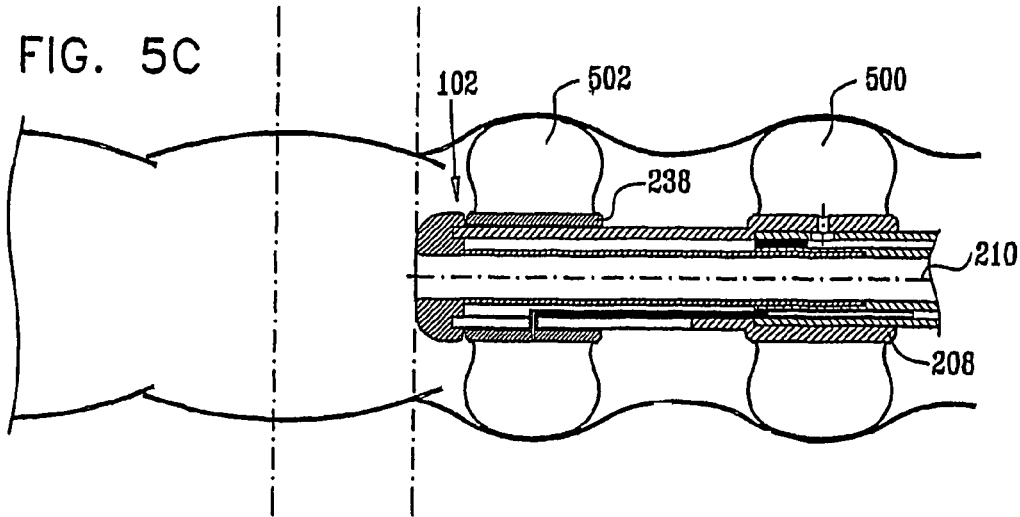

Turning to FIG. 5C, it is seen that with the forward balloon support 238 in its FIG. 5B axial orientation, the balloon 502 is inflated, thus engaging the inner wall of the intestine and fixing the position of the forward balloon support 238 relative thereto. Thereafter, as shown in FIG. 5D, balloon 500 is deflated.

Turning to FIG. 5E, it is seen that subsequent to deflation of balloon 500, the forward balloon support 238 is moved axially rearward relative to housing portion 208, while the forward balloon support 238 remains axially fixed relative to the intestine. This results in axial forward movement of the housing portion 208 and thus of the locomotive endoscope head 102.

Figure 5F:
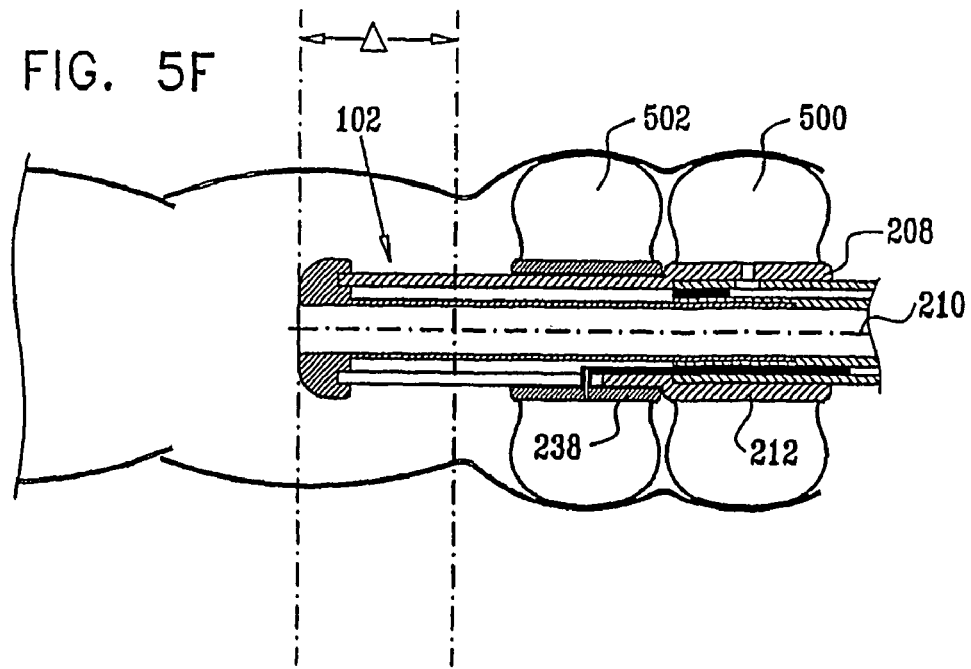
Figure 5G:
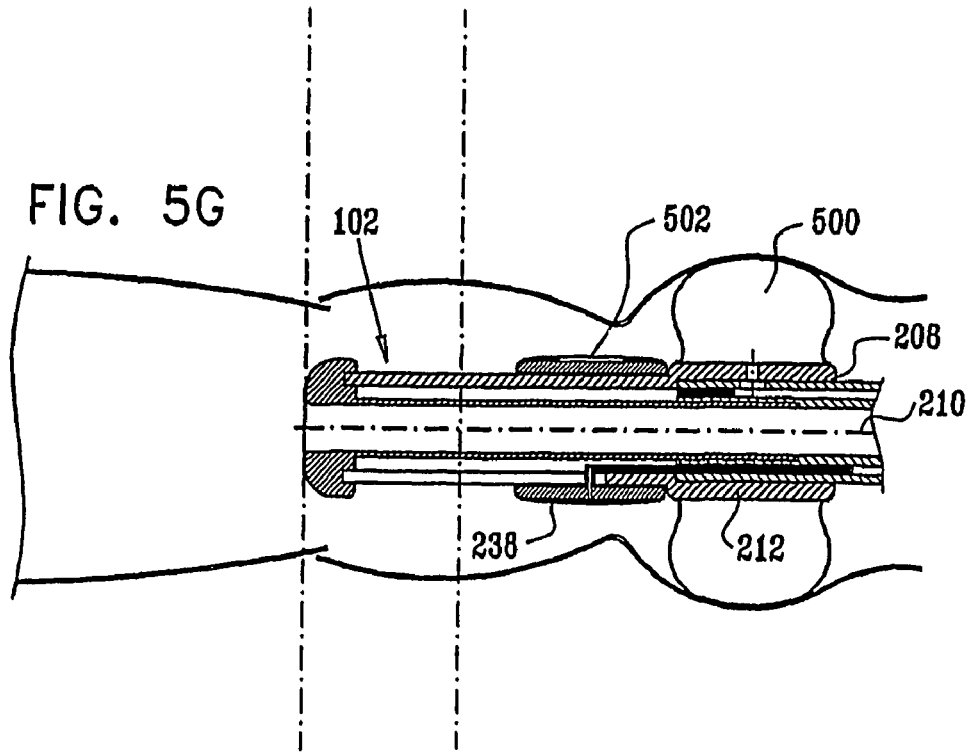

Turning to FIG. 5F, it is seen that with the forward balloon support 238 in its FIG. 5E axial orientation, the balloon 500 is inflated, thus engaging the inner wall of the intestine and fixing the position of the housing portion 208 relative thereto. Thereafter, as shown in FIG. 5G, balloon 502 is deflated.

It is thus appreciated that in this manner, forward displacement of the locomotive endoscope head 102 is effected.

Reference is now made to FIGS. 6A, 6B, 6C, 6D, 6E, 6F and 6G, which are simplified sectional illustrations, taken along lines IVB-IVB in FIG. 3, of the locomotive endoscope head of FIGS. 2-4C at various stages of rearward motion through an intestine. As seen in FIGS. 6A-6G, rearward locomotion of the locomotive endoscope head 102 of FIGS. 2-4C is achieved by a combination of sequential inflations and deflations of balloons, here too respectively designated by reference numerals 500 and 502 mounted onto the housing portion 208 and the forward balloon support 238, combined with relative axial displacement of forward balloon support 238 vis-à-vis housing portion 208. It is appreciated that each of balloons 500 and 502 preferably includes multiple separate and independently controllably inflatable and deflatable balloon portions as described hereinabove.

Figure 6A:
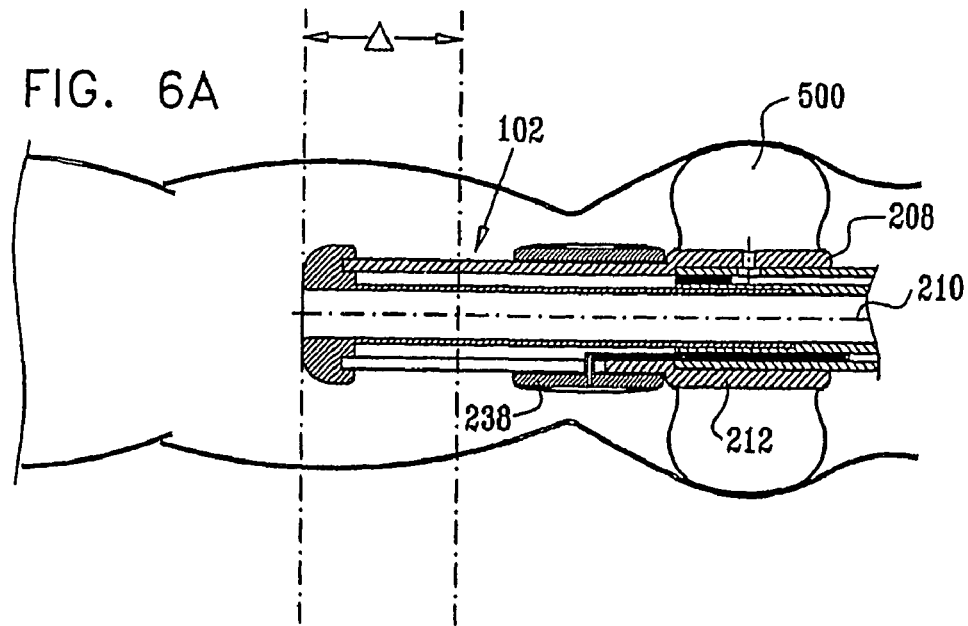
FIGS. 6A, 6B, 6C, 6D, 6E, 6F and 6G are simplified sectional illustrations, taken along lines IVB-IVB in FIG. 3 of the locomotive endoscope head of FIGS. 2-4C at various stages of rearward motion through an intestine.
Figure 6B:
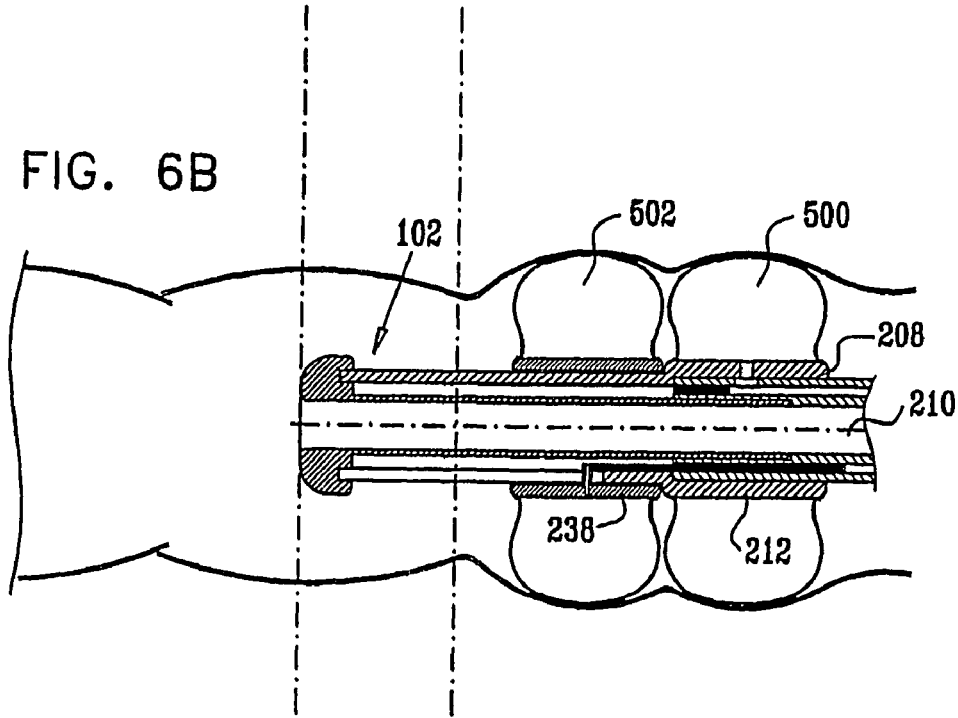
Figure 6C:
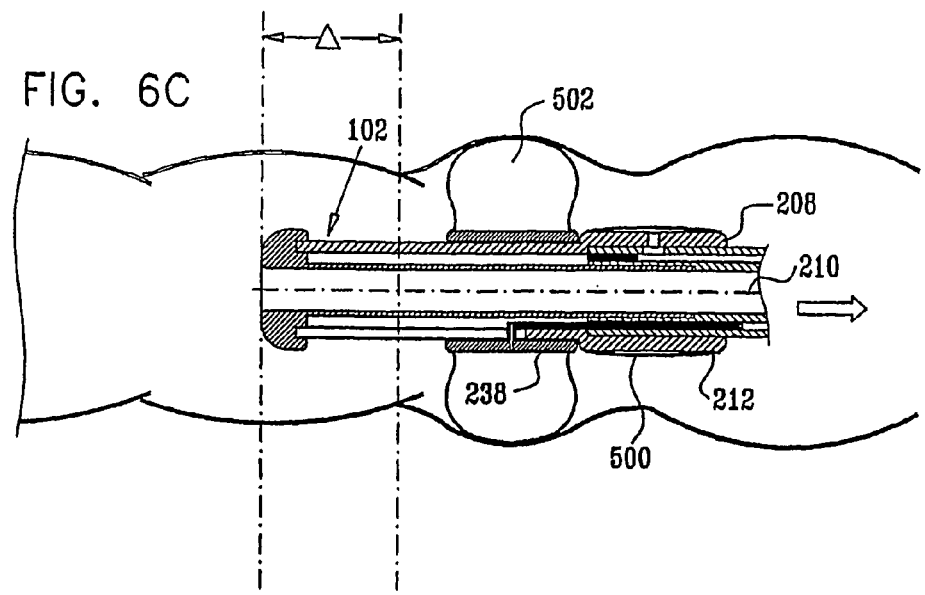

Turning to FIG. 6A, it is seen that balloon 500 is inflated, thus engaging an inner wall of an intestine and fixing the position of the housing portion 208 relative thereto. In this orientation, the forward balloon support 238 is shown in a rearward axial orientation, adjacent rear portion 212. Considering FIG. 6B, it is seen that with the forward balloon support 238 in its FIG. 6A axial orientation, the balloon 502 is inflated, thus engaging the inner wall of the intestine and fixing the position of the forward balloon support 238 relative thereto. Thereafter, as shown in FIG. 6C, balloon 500 is deflated.

Figure 6D:
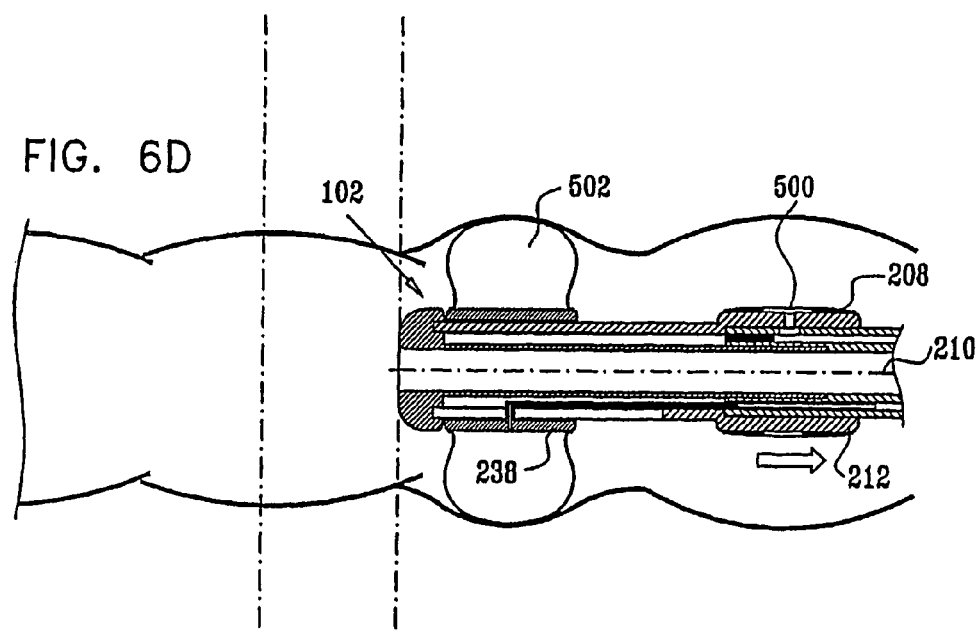

Turning to FIG. 6D, it is seen that forward balloon support 238 has moved axially forward relative to housing portion 208, while the forward balloon support 238 remains axially fixed relative to the intestine.

Figure 6E:
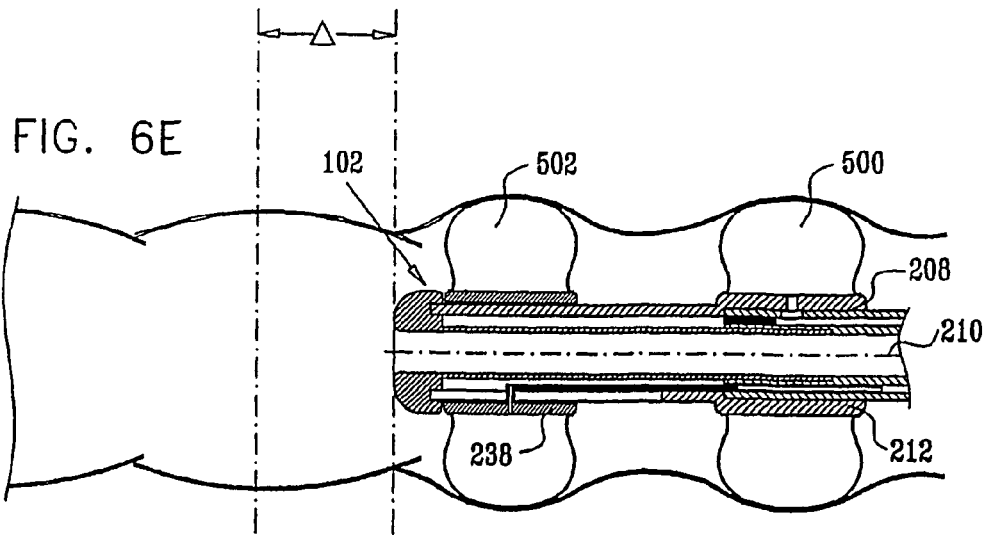
Figure 6F:
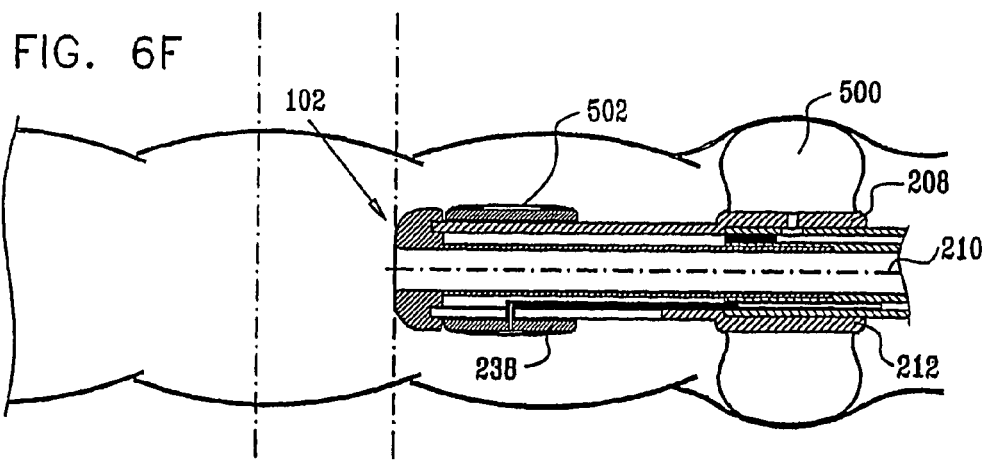

Turning to FIG. 6E, it is seen that with the forward balloon support 238 in its FIG. 6D axial orientation, the balloon 500 is inflated, thus engaging the inner wall of the intestine and fixing the position of the housing portion 208 relative thereto. Thereafter, as shown in FIG. 6F, balloon 502 is deflated.

Figure 6G:
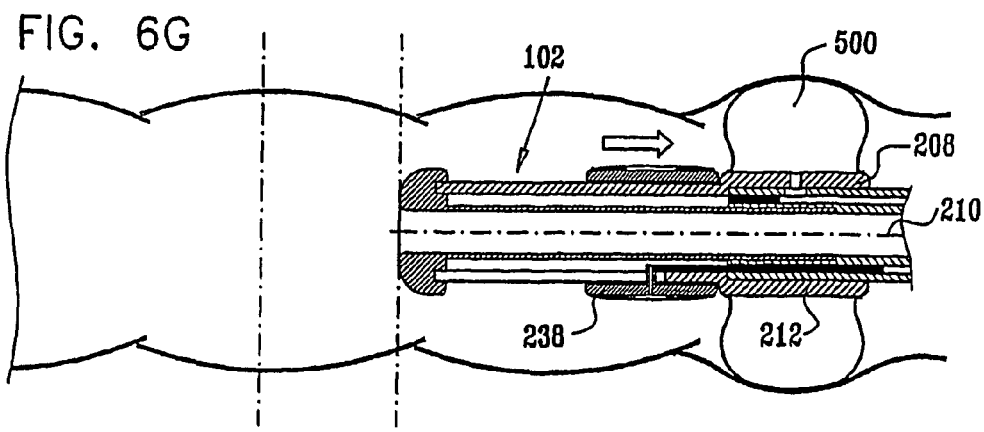

Turning now to FIG. 6G, it is seen that forward balloon support 238 has moved axially rearward relative to housing portion 208, while the housing portion 208 remains axially fixed relative to the intestine.

It is thus appreciated that in this manner, rearward displacement of the locomotive endoscope head 102 is effected. Alternatively, both balloons 500 and 502 may be deflated and the locomotive endoscope head 102 may be pulled out of the intestine by pulling on the multi-lumen tube 104.

Reference is now made to FIGS. 7A-9C, which illustrate various different orientations of the locomotive endoscope head 102 of FIGS. 2-4C which may be realized by suitable selectable inflation of individual balloon lobes of balloons 500 and 502. These illustrations are examples of non-parallel, tilted orientations achieved by any suitable non-identical inflation of balloon lobes of balloon 500 as well as a corresponding non-identical inflation of the balloon lobes 502 in an opposite sense, taking into account the phase difference in the rotational orientations of the balloon lobes of balloons 500 and 502.

Figure 7A:
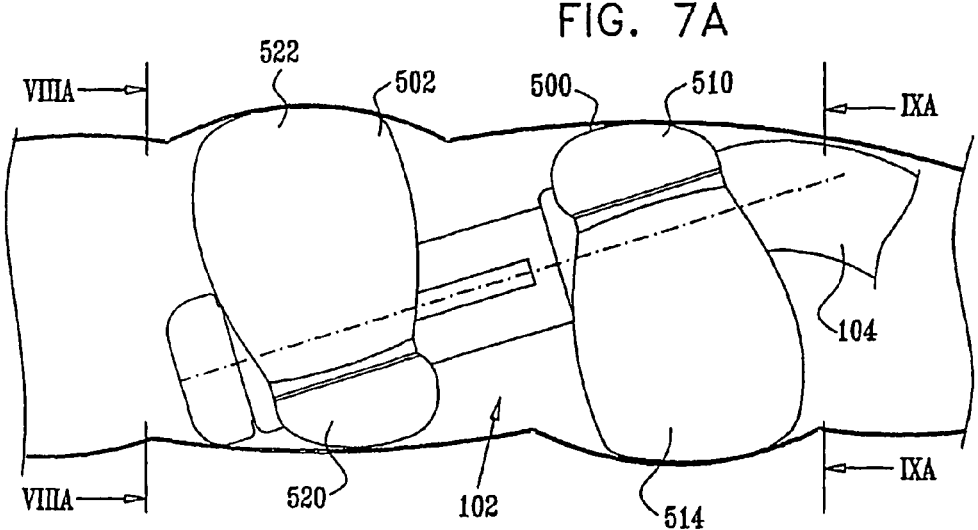
FIGS. 7A, 7B and 7C are side view illustrations of selectable tilting orientation of the locomotive endoscope head of FIGS. 1-6G within a body passageway.
Figure 7B:
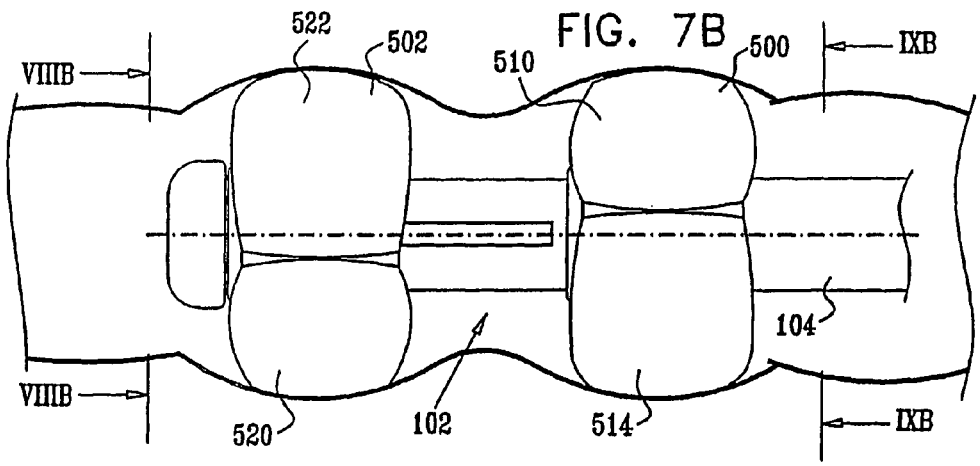
Figure 7C:
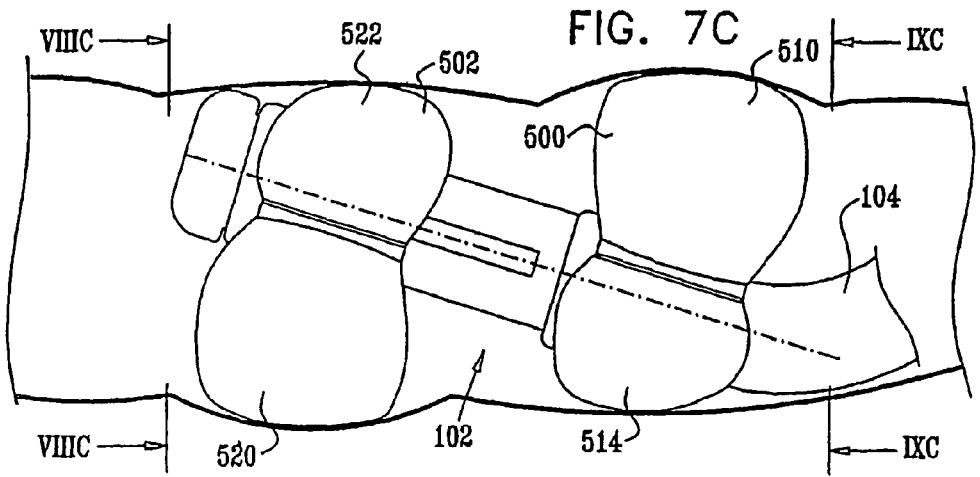
Figure 8A:
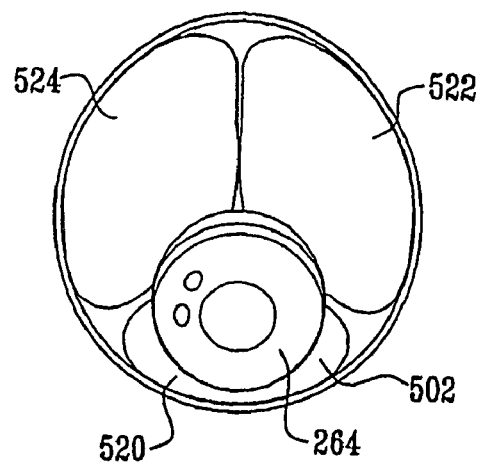
FIGS. 8A, 8B and 8C are simplified rearward facing views corresponding to FIGS. 7A, 7B and 7C, taken along planes VIIIA-VIIIA, VIIIB-VIIIB and VIIIC-VIIIC in FIGS. 7A, 7B and 7C respectively.
Figure 9A:
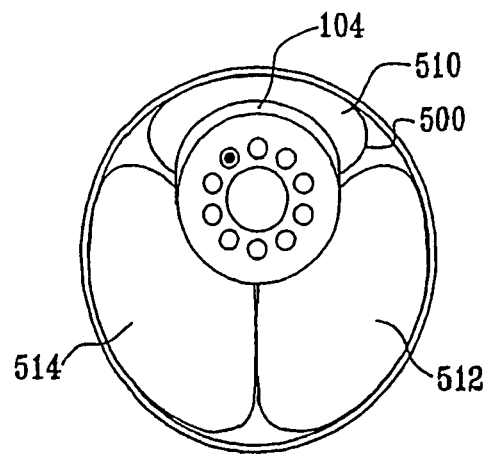
FIGS. 9A, 9B and 9C are simplified forward facing views corresponding to FIGS. 7A, 7B and 7C, taken along planes IXA-IXA, IXB-IXB and IXC-IXC in FIGS. 7A, 7B and 7C respectively.

Turning to FIGS. 7A, 8A and 9A, there are seen illustrations of a downward facing, selectable tilting orientation of the locomotive endoscope head of FIGS. 1-6G within a body passageway. This orientation is achieved by relatively low inflation of one balloon lobe of balloon 500, here designated by reference numeral 510 and relatively high inflation of balloon lobes of balloon 500 designated by reference numerals 512 and 514, at the same time as there is provided relatively low inflation of one balloon lobe of balloon 502, here designated by reference numeral 520 and relatively high inflation of balloon lobes of balloon 502 designated by reference numerals 522 and 524. It is noted that in the orientation of FIGS. 7A-7C, balloon lobes 510 and 520 are respectively at the top and the bottom of locomotive endoscope head 102, in the sense of FIGS. 7A-7C.

Figure 8B:
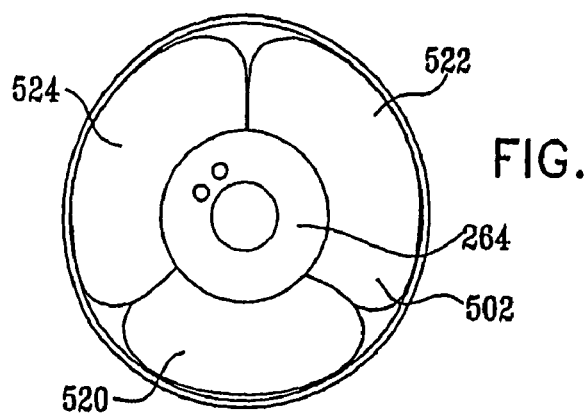
Figure 9B:
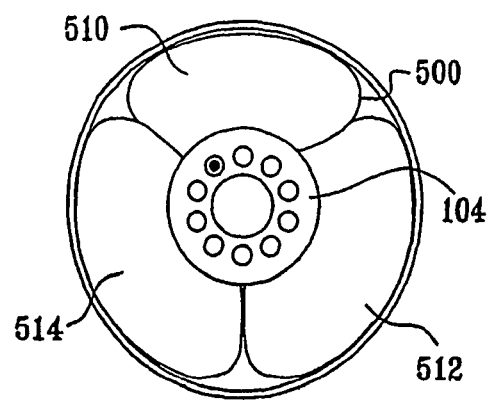

Turning to FIGS. 7B, 8B and 9B, there are seen illustrations of a second, parallel orientation of the locomotive endoscope head of FIGS. 1-6G within a body passageway. This orientation is achieved by generally identical inflation of balloon lobes 510, 512 and 514 of balloon 500 as well as identical inflation of balloon lobes 520, 522 and 524 of balloon 502.

Figure 8C:
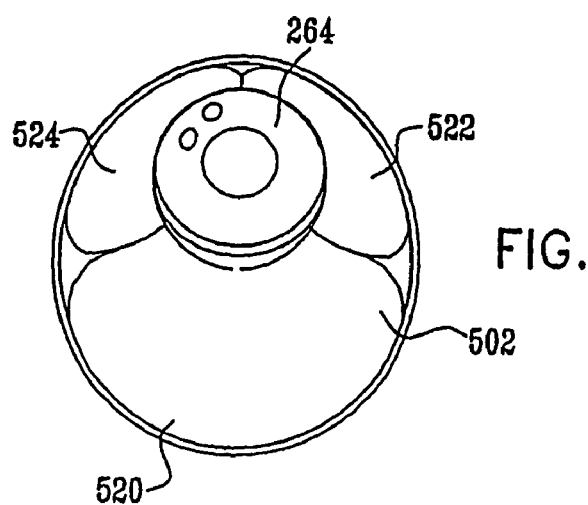
Figure 9C:
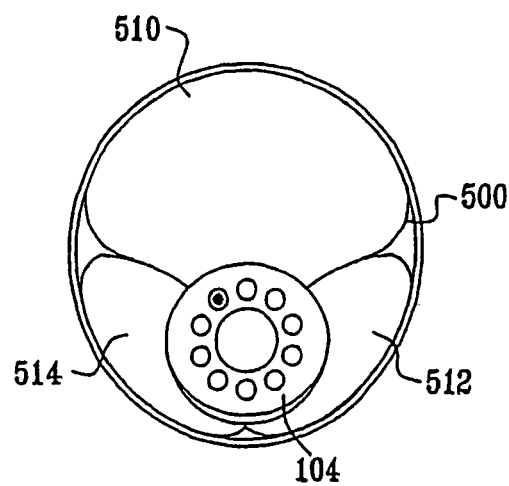

Turning to FIGS. 7C, 8C and 9C, there are seen illustrations of a third, upward facing, selectable tilting orientation of the locomotive endoscope head of FIGS. 1-6G within a body passageway. This orientation is achieved by relatively high inflation of balloon lobe 510 of balloon 500 and relatively low inflation of balloon lobes 512 and 514 of balloon 500, at the same time as there is provided relatively high inflation of balloon lobe 520 of balloon 502 and relatively low inflation of balloon lobes 522 and 524 of balloon 502.

Figure 10A:
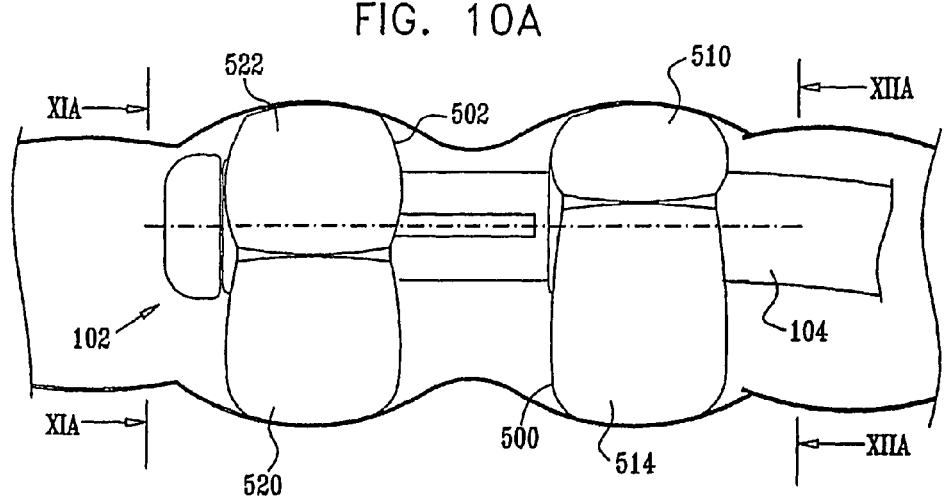
FIGS. 10A and 10B are side view illustrations of selectable parallel orientation of the locomotive endoscope head of FIGS. 1-6G within a body passageway.
Figure 10B:
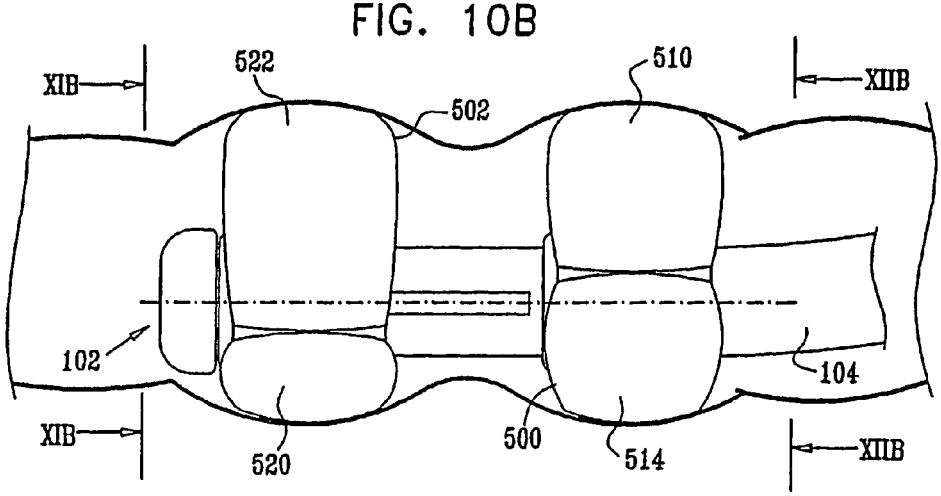
Figure 11A:
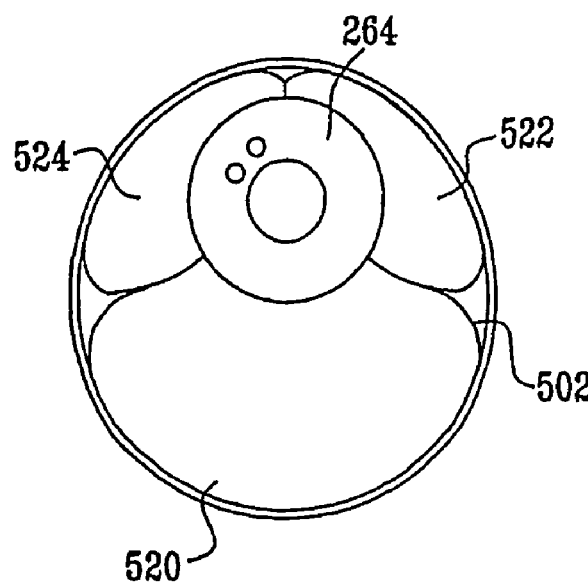
FIGS. 11A and 11B are simplified rearward facing views corresponding to FIGS. 10A and 10B taken along planes XIA-XIA and XIB-XIB in FIGS. 10A and 10B respectively.
Figure 11B:
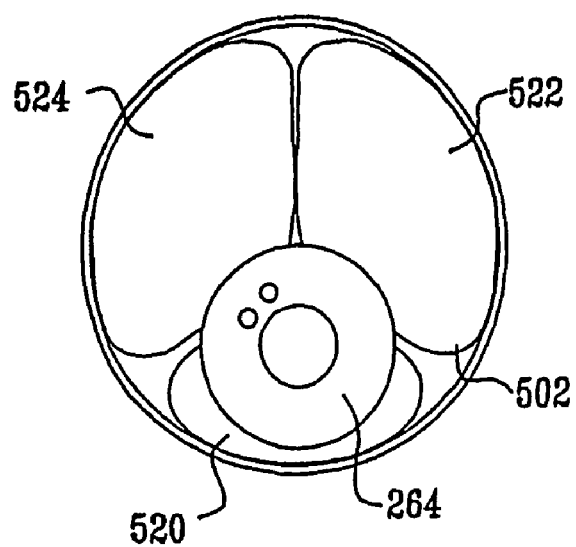
Figure 12A:
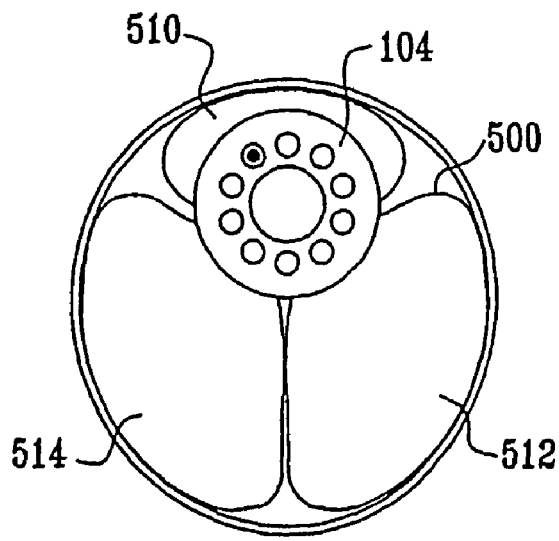
FIGS. 12A and 12B are simplified forward facing views corresponding to FIGS. 10A and 10B taken along planes XIIA-XIIA and XIIB-XIIB in FIGS. 10A and 10B respectively.
Figure 12B:
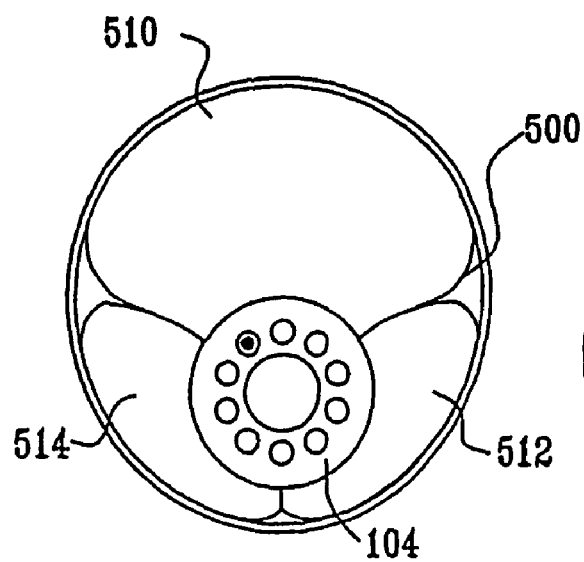

Reference is now made to FIGS. 10A and 10B, which are side view illustrations of selectable parallel, off-center orientation of the locomotive endoscope head of FIGS. 1-6G within a body passageway, to FIGS. 11A and 11B, which are rearward facing views corresponding to FIGS. 10A and 10B taken along planes XIA-XIA and XIB-XIB in FIGS. 10A and 10B respectively and to FIGS. 12A and 12B, which are forward facing views corresponding to FIGS. 10A and 10B taken along planes XIIA-XIIA and XIIB-XIIB in FIGS. 10A and 10B respectively. These illustrations are examples of parallel orientations achieved by any suitable non-identical inflation of balloon lobes 510, 512 and 514 of balloon 500 as well as a corresponding non-identical inflation of balloon lobes 520, 522 and 524 of balloon 502, taking into account the phase difference in the rotational orientations of the balloon lobes of balloons 500 and 502.

Turning to FIGS. 10A, 11A and 12A, there are seen illustrations of a first, off center parallel orientation of the locomotive endoscope head of FIGS. 1-6G within a body passageway. This orientation is achieved by relatively low inflation of balloon lobe 510 and relatively high inflation of balloon lobes 512 and 514 of balloon 500 as well as a corresponding relatively high inflation of balloon lobe 520 and relatively low inflation of balloon lobes 522 and 524 of balloon 502, which takes into account the phase difference in the rotational orientations of the balloon lobes of balloons 500 and 502.

Turning to FIGS. 10B, 11B and 12B, there are seen illustrations of a second, off center parallel orientation of the locomotive endoscope head of FIGS. 1-6G within a body passageway. This orientation is achieved by relatively high inflation of balloon lobe 510 and relatively low inflation of balloon lobes 512 and 514 of balloon 500 as well as a corresponding relatively low inflation of balloon lobe 520 and relatively high inflation of balloon lobes 522 and 524 of balloon 502.

It may be appreciated from a consideration of FIGS. 7A-12B that in practice any desired, geometrically permitted, orientation of the locomotive endoscope head 102 may be realized if at least three balloon lobes are provided on both balloons 500 and 502. This includes, for example up-down and side-to-side tilts and combinations thereof as well as desired up-down and side-to-side off-center parallel orientations and combinations thereof.

It is appreciated that various desired, geometrically permitted, orientations of the locomotive endoscope head 102 may be realized if at least two balloon lobes are provided on each of balloons 500 and 502, and in particular if the at least two balloon lobes of balloons 500 and 502 are azimuthally offset.

It is a particular feature of the present invention that due to the fact that the locomotive endoscope is moved other than by a push mechanism, multi-lumen tube 104 may be substantially more flexible than other endoscope tubes.

Figure 13:
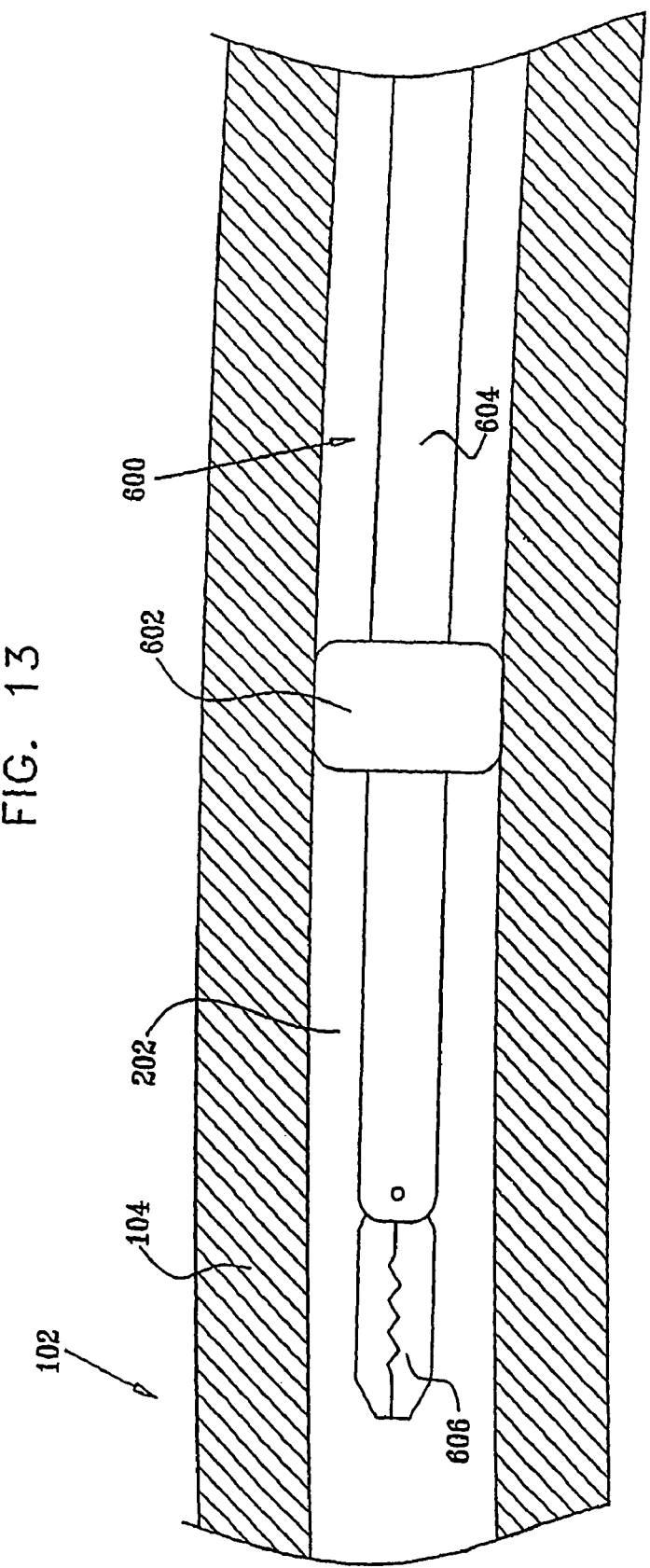
FIG. 13 is a simplified pictorial illustration of an accessory which is adapted to travel through the instrument channel in the locomotive endoscope head of any of FIGS. 1-12B.

Reference is now made to FIG. 13, which is a simplified pictorial illustration of an accessory 600 which is adapted to travel through the instrument channel defined in the central passageway 202 of the multi-lumen tube 104 and in interior bore 274 of cylindrical portion 266 of locomotive endoscope head 102. The accessory 600 may be selected from among any suitable accessories, such as biopsy forceps, polypectomy snares, foreign body retrieval devices, heat probes and needles, some of which are well known in the art. In accordance with a preferred embodiment of the invention, a piston 602 is associated with the accessory along its body 604 and upstream of its head 606. The piston 602 is configured for slidable sealed motion along the instrument channel in response to pressure differences upstream and downstream thereof, such as provided by suitable positive or negative pressurization of the instrument channel, which may be carried out for example, by conventional inssuflation and suction functionalities that are provided in conventional endoscope systems.

Figure 14:
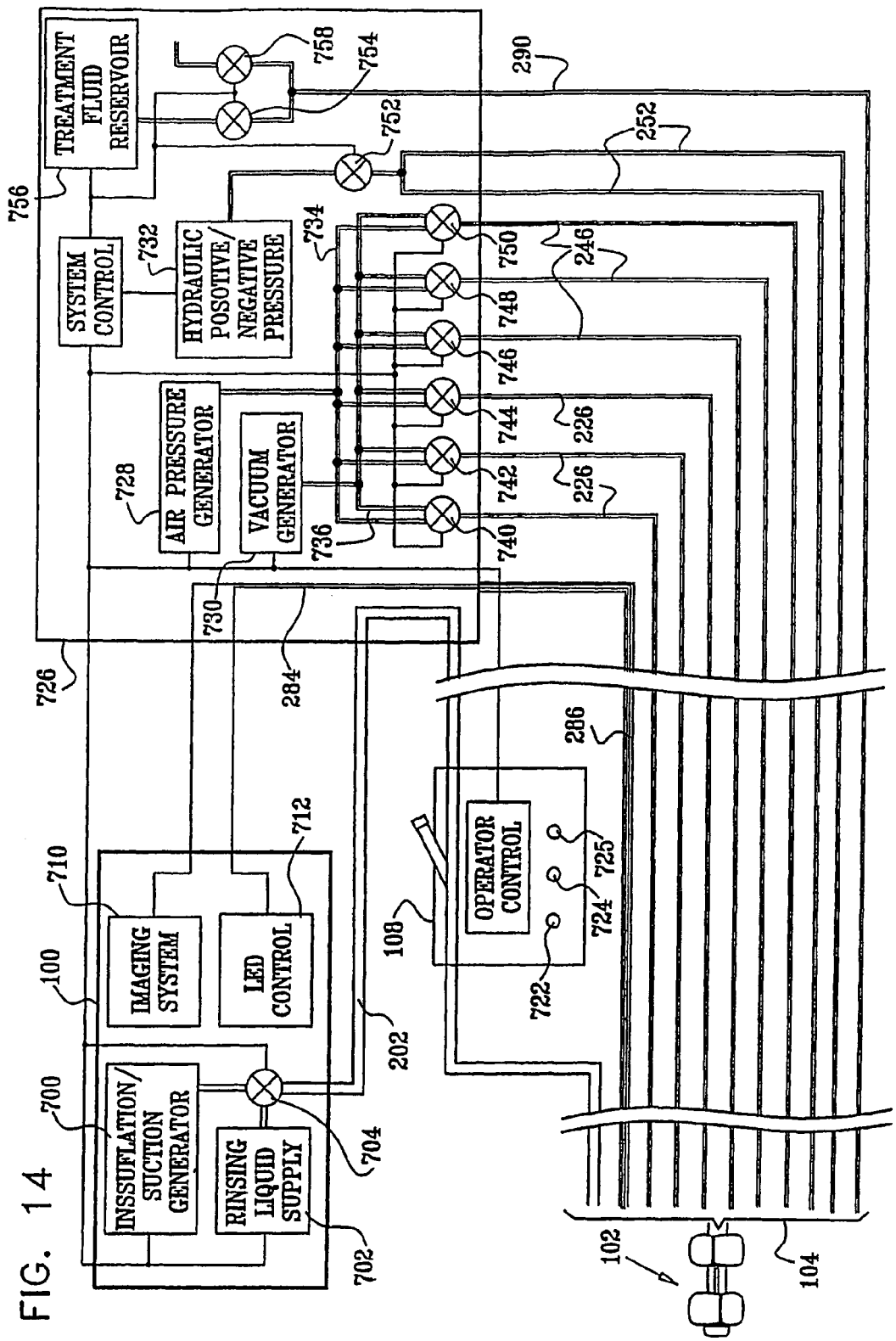
FIG. 14 is a simplified partially block diagram, partially schematic illustration of part of the endoscopy system of FIGS. 1-13, constructed and operative in accordance with a preferred embodiment of the present invention.

Reference is now made to FIG. 14, which is a simplified partially block diagram, partially schematic illustration of part of the endoscopy system of FIGS. 1-13, constructed and operative in accordance with a preferred embodiment of the present invention.

As seen in FIG. 14, a conventional endoscopy system 100, such as a console including a CV-160 video system center, a CLC-160 light source, an OEV-203 video monitor, and an OFP flushing pump, all commercially available from Olympus America Inc. of 2 Corporate Center Drive, Melville, N.Y. 11747, USA, is being employed. Conventional endoscopy system 100 includes an inssuflation/suction generator 700 and a liquid supply 702 which communicate via a flow control valve 704 with the instrument channel defined by central passageway 202 of the multi-lumen tube 104 and by interior bore 274 of cylindrical portion 266 of locomotive endoscope head 102. The conventional endoscopy system 100 also preferably includes an imaging system 710 and an LED controller 712 which communicate via electrical data and power lines preferably embodied in optical fiber and electrical conductor bundle 284 which extend through lumen 286 in multi-lumen tube 104.

Operator control 108, preferably including a joystick 722, tilt/non-tilt functionality selection switch 724 and a button 725 for governing the direction (forward/backward) and speed of motion, governs the operation of locomotive head controller 106. In a preferred embodiment of the present invention, as shown, the operator control 108 provides control inputs to locomotive head control circuitry 726, which operates an air pressure generator 728, a vacuum generator 730 and a hydraulic positive/negative pressure supply 732.

Air pressure generator 728 and vacuum generator 730 are coupled to lumens 226 and 246 for selectable inflation of balloon lobes 510, 512, 514, 520, 522 and 524 via suitable manifolds 734 and 736 and via individual flow valves for each of the lumens, the flow valves being designated by reference numerals 740, 742, 744, 746, 748 and 750. Hydraulic positive/negative pressure supply 732 is coupled via a flow valve 752 to lumens 252 for driving piston rods 250. Additionally a flow valve 754 governs supply of a treatment fluid to lumen 290 from a treatment fluid reservoir 756. A further fluid valve 758 governs removal of the treatment fluid via lumen 290 from the intestine to a discard fluid location (not shown) which is maintained under vacuum.

Figure 15:
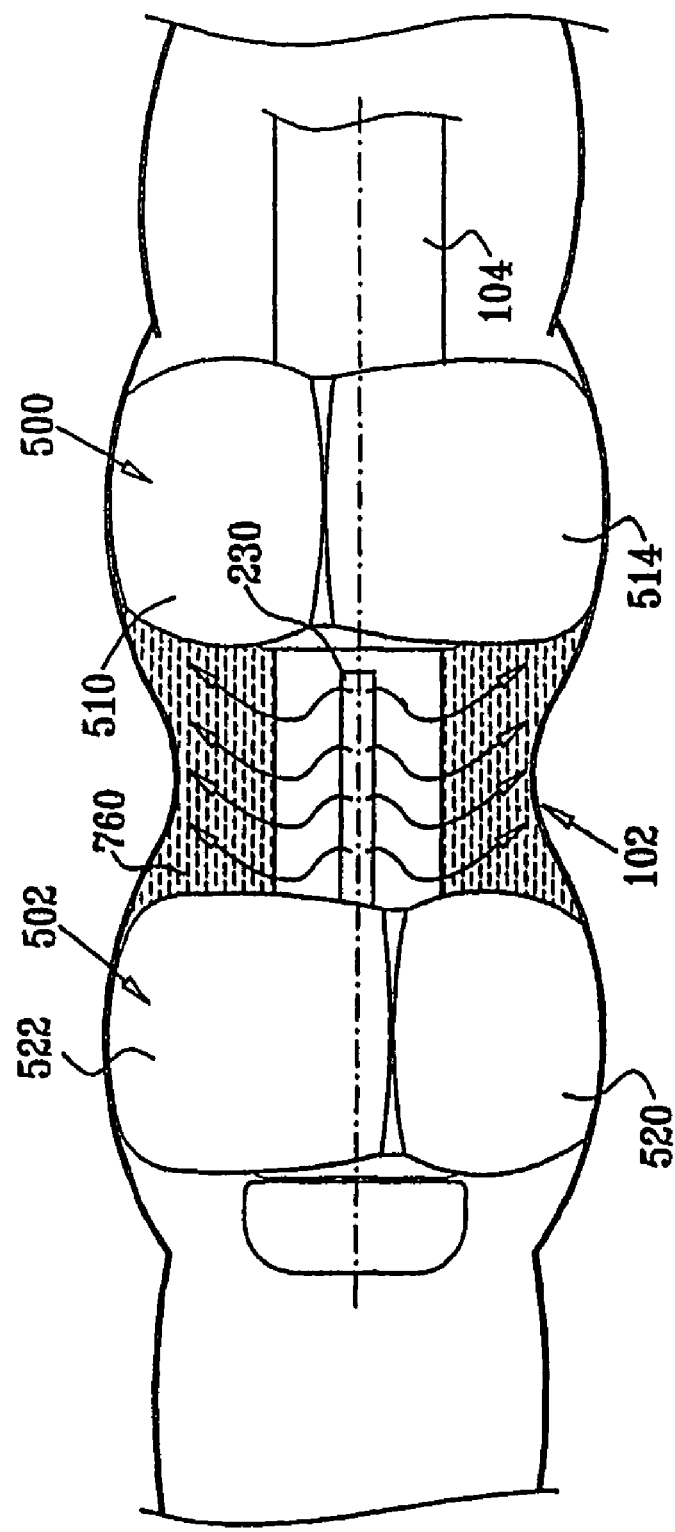
FIG. 15 is a simplified pictorial illustration of the locomotive endoscope head of FIGS. 1-12B in an intestine fluid treatment mode of operation.
Figure 17:
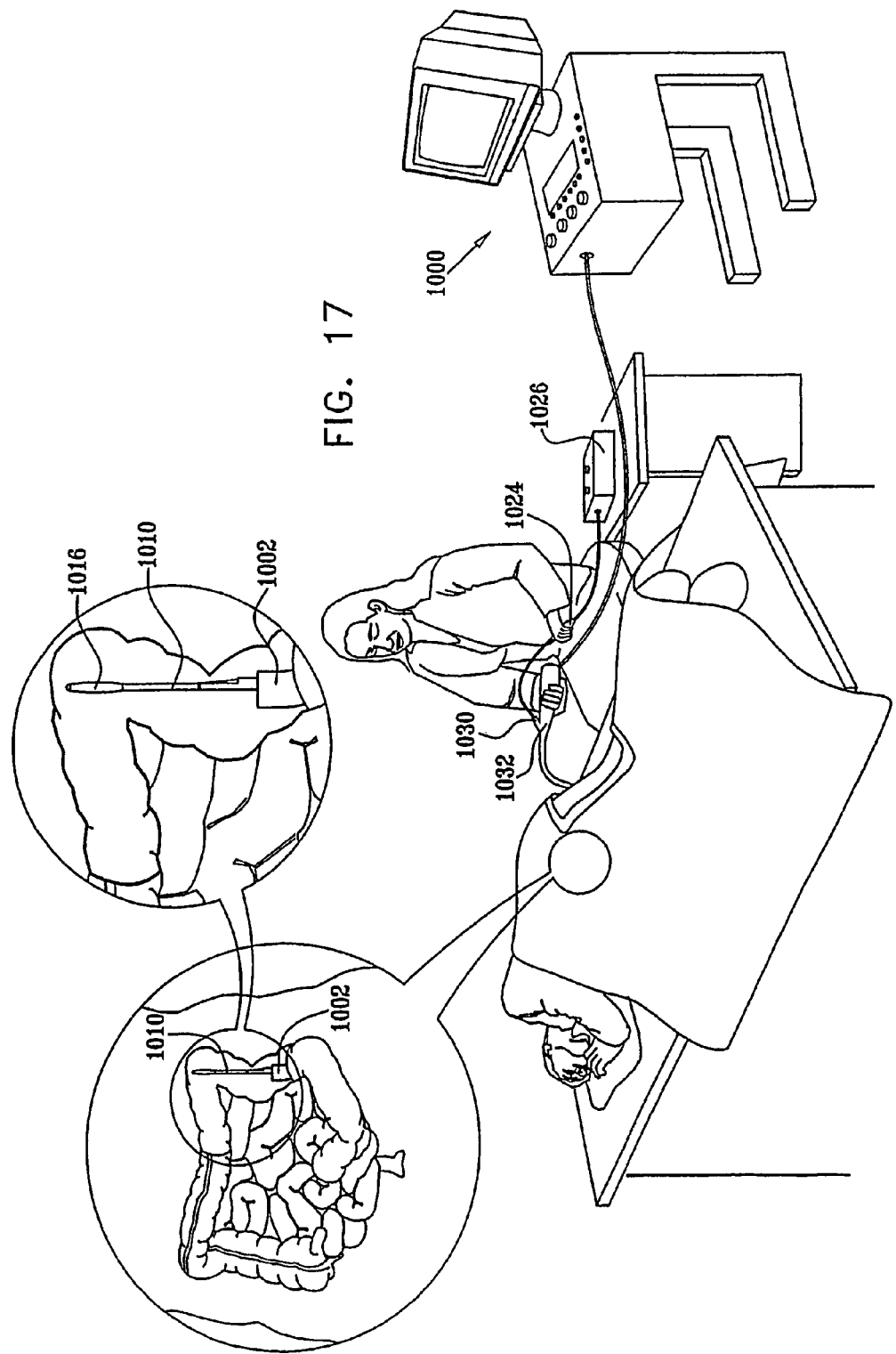
FIG. 17 is a simplified pictorial illustration of an endoscopy system constructed and operative in accordance with another preferred embodiment of the present invention.
Figure 18:
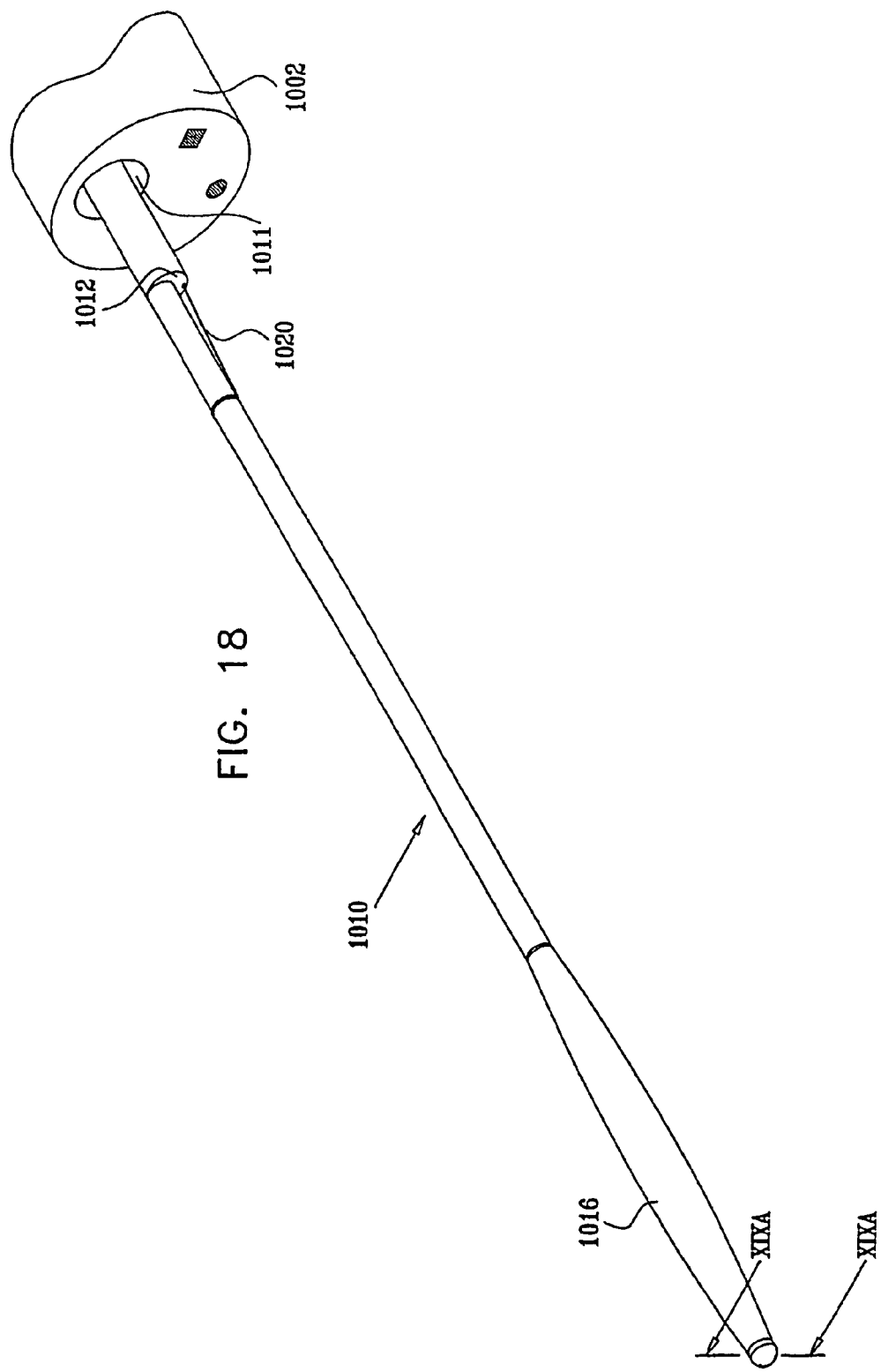

Flow valves 704, 740, 742, 744, 746, 748, 750, 752, 754 and 758 are controlled by operator control 108 via locomotive head control circuitry 726 to suitably inflate and deflate balloon lobes 510, 512, 514, 520, 522 and 524 for providing selected positioning and/or tilt of the locomotive endoscope head 102 within the intestine; to suitably displace forward balloon support 238 for locomotion of the locomotive endoscope head 102 and for selectably supplying treatment fluid to the intestine as described hereinbelow with reference to FIG. 15.

Reference is now made to FIG. 15, which is a simplified pictorial illustration of the locomotive endoscope head of FIGS. 1-12B in an intestine fluid treatment mode of operation. As seen in FIG. 15, tubular body portion sealing elements such as balloon lobes 510, 512 and 514 of balloon 500 and balloon lobes 520, 522 and 524 of balloon 502 are preferably all inflated, so as to seal the volume of the intestine intermediate balloon lobes 510, 512 and 514 and balloon lobes 520, 522 and 524 from the remainder of the interior volume of the intestine.

Once sealing is achieved, a treatment fluid 760 is supplied from treatment fluid reservoir 756 via valve 754, lumen 290 and slots 230 to the sealed portion of the intestine. Following treatment, the treatment fluid 760 may be suctioned from the sealed portion of the intestine via slots 230, lumen 290 and valve 758 to a fluid discard location (not shown). Optionally and preferably, treatment fluid 760 includes at least one of a therapeutic fluid, a contrast enhancing fluid, an antiseptic fluid, an acidic solution, a basic solution or any other suitable fluid.

Reference is now made to FIGS. 16A-16C, which are simplified pictorial illustrations of the locomotive endoscope head of FIGS. 1-12B in a guide wire mode of operation. As seen in FIG. 16A, balloon lobes 510, 512 and 514 of balloon 500 and balloon lobes 520, 522 and 524 of balloon 502 are preferably all inflated, so as to anchor the locomotive endoscope head 102 to the intestine. Once anchoring is achieved at a desired location, multi-lumen tube 104 is tensioned, as seen in FIG. 16B.

It is appreciated that respective diameter of balloons 500 and 502 are sufficient to ensure tight anchoring at any part of the intestine.

As seen in FIG. 16C, an overtube 800 is slid over multi-lumen tube 104, using it as a guide wire. The overtube 800 preferably includes, at a forward portion 802 thereof, an endoscopy tool 804. Preferably, endoscopy tool 804 may be a therapeutic, diagnostic or surgical tool, and may be selectably positioned along the multi-lumen tube 104. In a preferred embodiment of the present invention, endoscopy tool 804 is an ultrasonic transducer. In another preferred embodiment of the present invention, endoscopy tool 804 is an X-ray radiation source/generator.

Reference is now made to FIGS. 17-19B, which are respectively a simplified pictorial illustration of an endoscopy system constructed and operative in accordance with another preferred embodiment of the present invention and respective simplified pictorial and sectional view illustrations of an accessory constructed and operative in accordance with a preferred embodiment of the present invention.

As seen in FIGS. 17-19B, a conventional endoscopy system 1000, such as a console including a CV-160 video system center, a CLC-160 light source, an OEV-203 video monitor, and an OFP flushing pump, all commercially available from Olympus America Inc. of 2 Corporate Center Drive, Melville, N.Y. 11747, USA, is being employed. A conventional endoscope 1002, which forms part of conventional endoscopy system 1000 may be employed, such as a CF-Q160AL video colonoscope which is commercially available from Olympus America Inc. of 2 Corporate Center Drive, Melville, N.Y. 11747, USA.

An endoscope tool 1010, constructed and operative in accordance with a preferred embodiment of the present invention extends through the instrument channel 1011 of the conventional endoscope 1002. Endoscope tool 1010 is characterized in that it includes a multi-lumen tube 1012 which includes at least a first lumen 1014 for inflation and deflation of a balloon 1016 via an inflation aperture 1017, and a second lumen 1018. Preferably the second lumen 1018 may accommodate a tensioning or compression wire 1020. Alternatively or additionally, the second lumen 1018 may have other functionality. As a further alternative, the multi-lumen tube 1012 forming part of the endoscope tool 1010 may include more than two lumens. Preferably, the cross-sectional area of the multi-lumen tube 1012 is sufficiently less than that of the instrument channel 1011, so as to allow supply of fluid for inssuflation and draining of fluid therethrough.

It is appreciated that in accordance with a preferred embodiment of the present invention the endoscope tool 1010 and the multi-lumen tube 1012 are generally substantially more flexible than conventional endoscope 1002 and an endoscope tube thereof.

It is appreciated that in accordance with a preferred embodiment of the present invention the balloon 1016 is generally stretchable, and can be stretched to a diameter about 5-20 times larger than its diameter when not inflated. In a specific embodiment, useful for small intestine endoscopy, the balloon diameter when fully stretched is four centimeters. Preferably, inflation of the balloon 1016 to a diameter less than four centimeters may be achieved using relatively low pressure, such as in the range of 10-50 milibars. In another specific embodiment, useful for large intestine endoscopy, the balloon diameter when fully stretched is seven centimeters. Preferably, inflation of the balloon 1016 to a diameter less than seven centimeters may be achieved using relatively low pressure, such as in the range of 10-50 milibars.

It is appreciated that in accordance with a preferred embodiment of the present invention useful for in vivo inspection of a generally tubular body portion having a variable cross-sectional diameter, the expansion diameter range of balloon 1016 is larger than the maximum cross-sectional diameter of the generally tubular body portion, thereby ensuring engagement of expanded balloon 1016 with the interior surface of the generally tubular body portion, and anchoring of the endoscope tool 1010 thereto. Preferably, balloon 1016 is a relatively soft, highly compliant balloon, operative to at least partially conform to the shape of the interior surface of the generally tubular body portion when in engagement therewith.

It is appreciated that balloon 1016 may be formed of well-known stretchable materials such as latex, flexible silicon, or highly flexible nylon. Alternatively, balloon 1016 may be formed of polyurethane, which is less stretchable and conforming than latex, flexible silicon or highly flexible nylon. Preferably, the diameter of balloon 1016 is sufficient to ensure tight anchoring at any part of the generally tubular body portion.

As seen in FIGS. 17-19B, the endoscope tool 1010 preferably includes a tool positioning control device 1024 and a balloon inflation/deflation control interface 1026. It is appreciated that multi-lumen tube 1012 and the entire endoscope tool 1010 may be inserted and removed via a conventional tool port 1030 on a conventional operator control 1032 which forms part of conventional endoscope 1002.

Reference is now made to FIGS. 20A, 20B, 20C, 20D, 20E, 20F, 20G, 20H and 20I, which are simplified illustrations of the endoscope tool 1010 of FIGS. 17-19B in various operative orientations. In the illustrated embodiment, desired directional orientation of the forward end of the endoscope tool 1010 is obtained by suitable axial displacement of the tool through the instrument channel 1011 of the endoscope 1002 combined with suitable tensioning of wire 1020 and with suitable rotational orientation of the endoscope tool 1010 relative to the intestine.

Figure 20A:
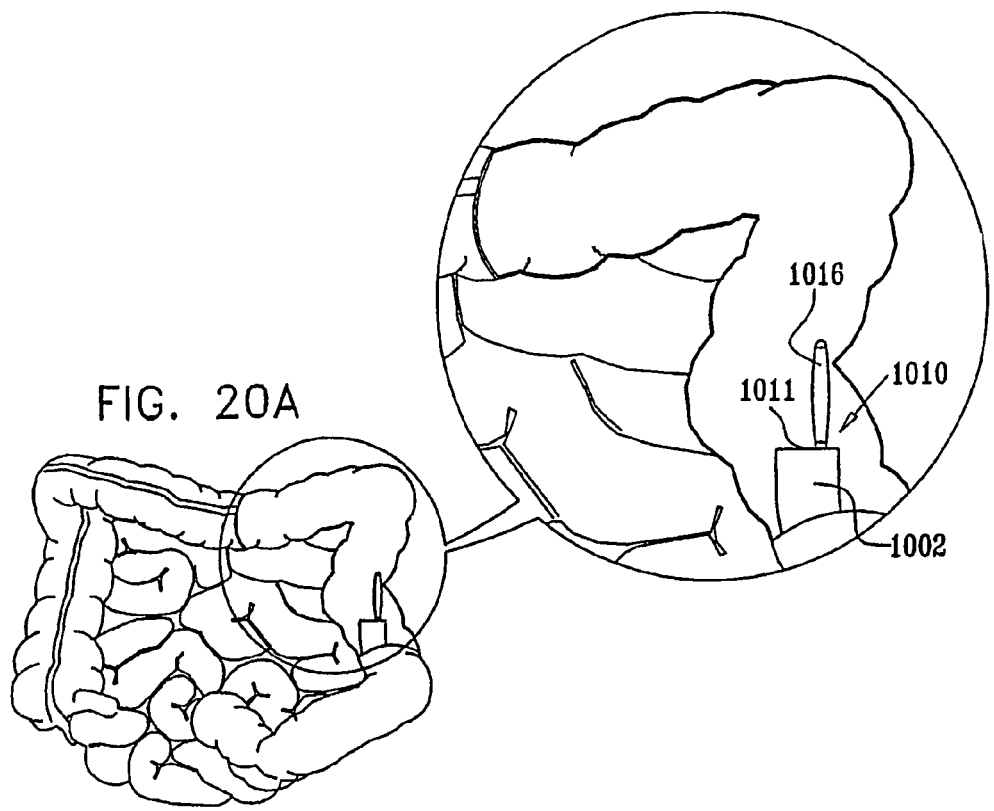

As seen in FIG. 20A, endoscope tool 1010 is principally located within the instrument channel 1011 of endoscope 1002, and has balloon 1016 protruding therefrom, while in a deflated state.

Figure 20B:
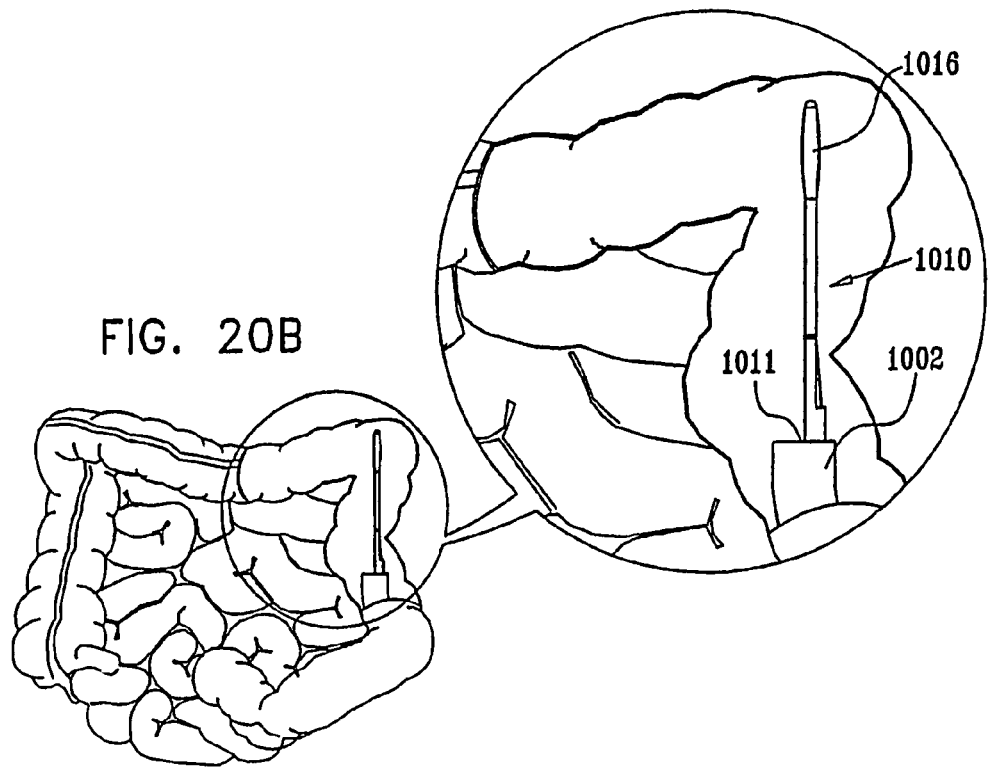
Figure 20C:
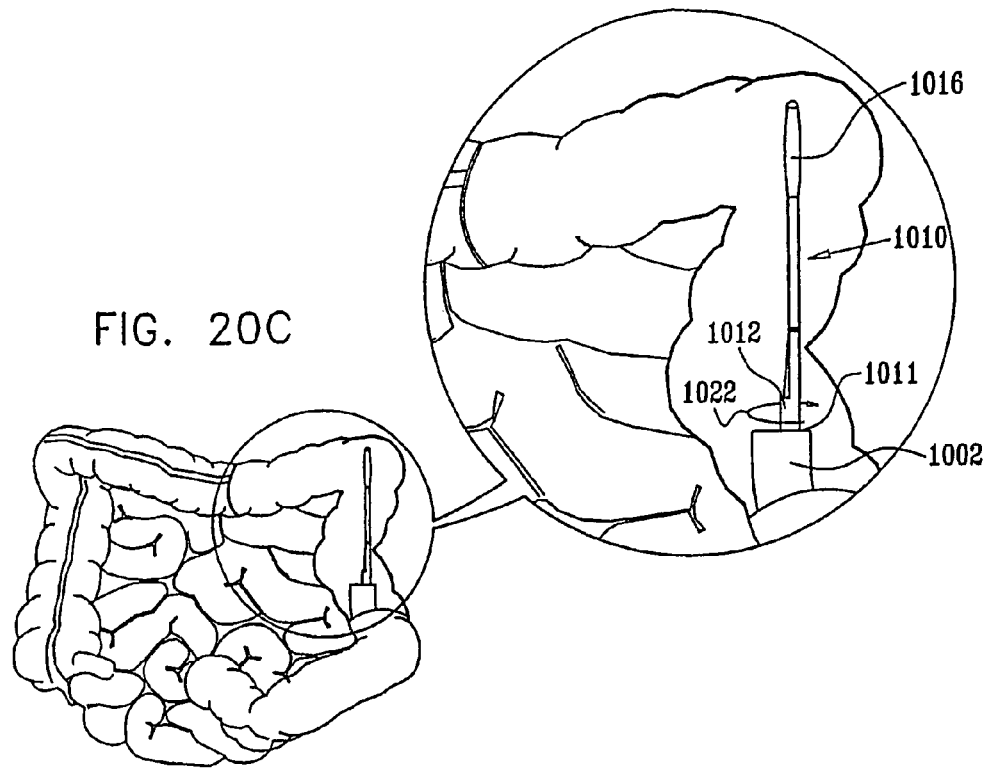

FIG. 20B shows the endoscope tool 1010 extending further from the instrument channel 1011, while FIG. 20C shows the endoscope tool 1010 having been rotated by 180 degrees relative to its orientation in FIG. 20B by suitable twisting of multi-lumen tube 1012, as indicated by arrow 1022.

Figure 20D:
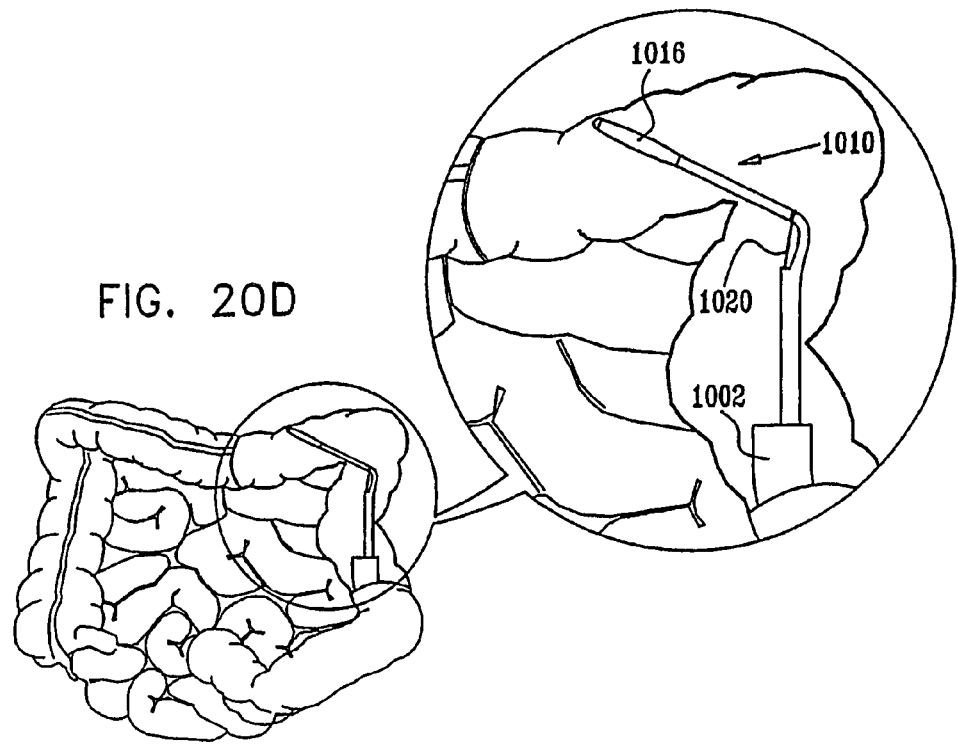

FIG. 20D shows bending of the forward end of the endoscope tool 1010 resulting from tensioning of wire 1020, when the tool is in its FIG. 20C orientation having been pushed forward in a conventional manner.

Figure 20E:
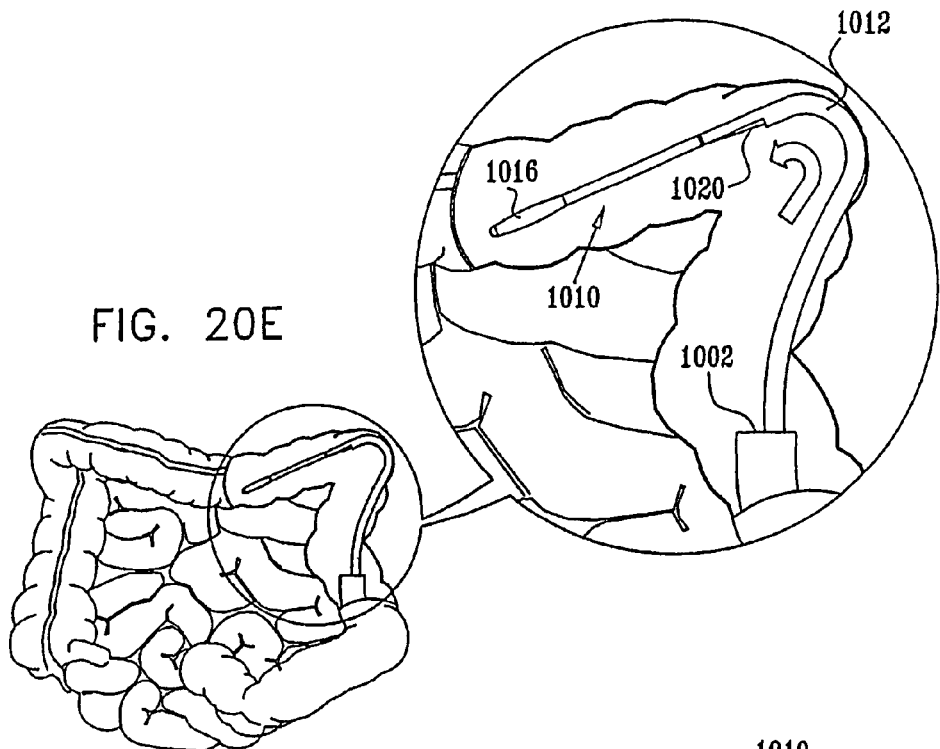

FIG. 20E shows further progress of the endoscope tool 1010 through the intestine resulting from forward pushing of the tool coupled with release the tension on the wire 1020 by operation of tool positioning control device 1024.

Figure 20F:
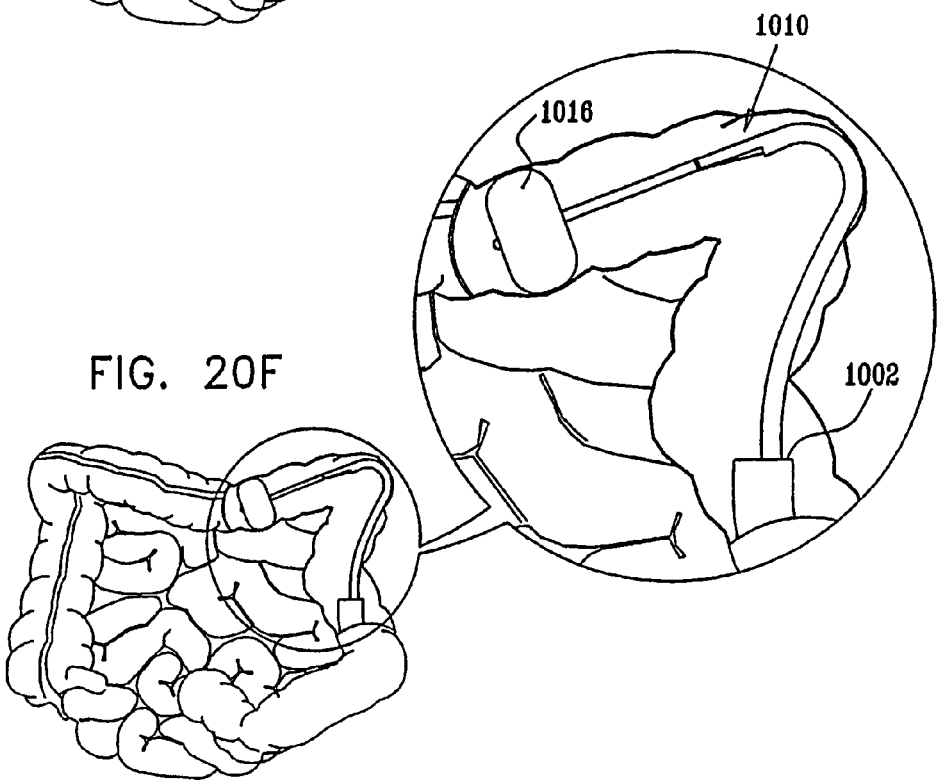

FIG. 20F shows inflation of the balloon 1016 by operation of the balloon inflation/deflation control interface 1026. In accordance with a preferred embodiment of the invention, this inflation anchors the forward end of the endoscope tool 1010 to the intestine at the location of the balloon 1016.

Figure 20G:
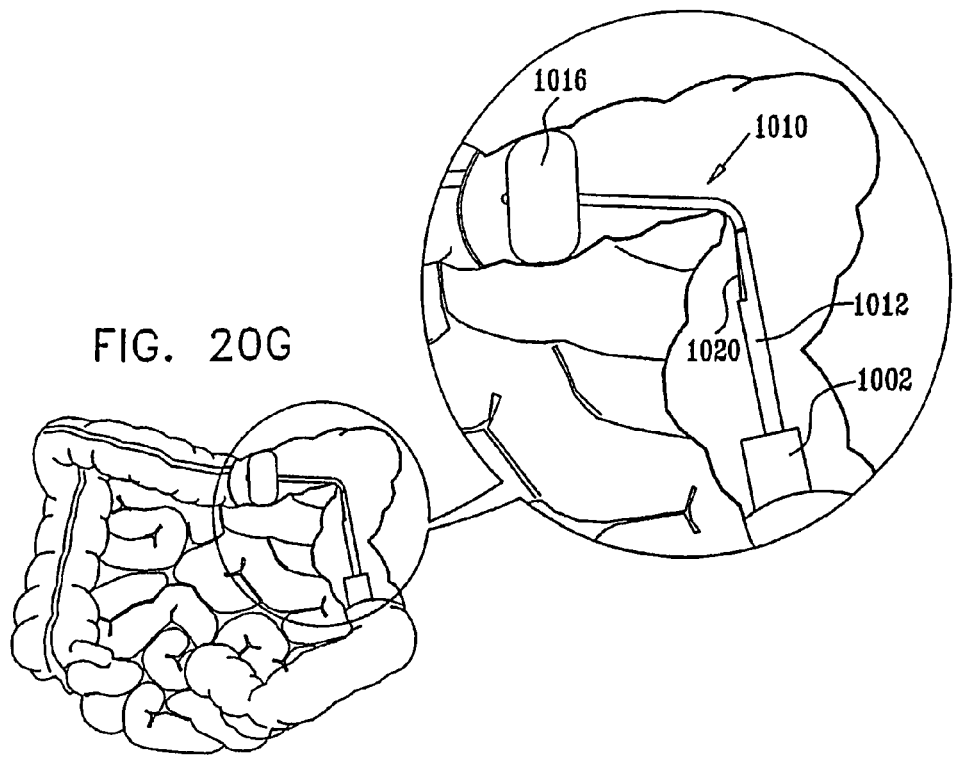

FIG. 20G shows tensioning of the endoscope tool 1010 including the multi-lumen tube 1012 by pulling on the multi-lumen tube 1012.

Figure 20H:
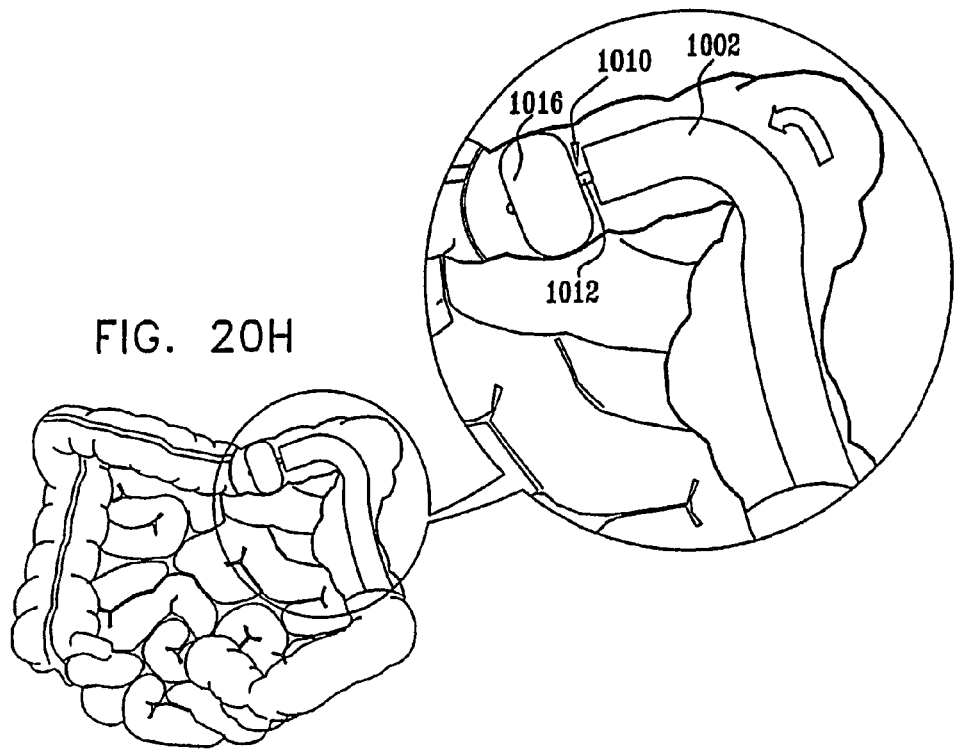
Figure 201:
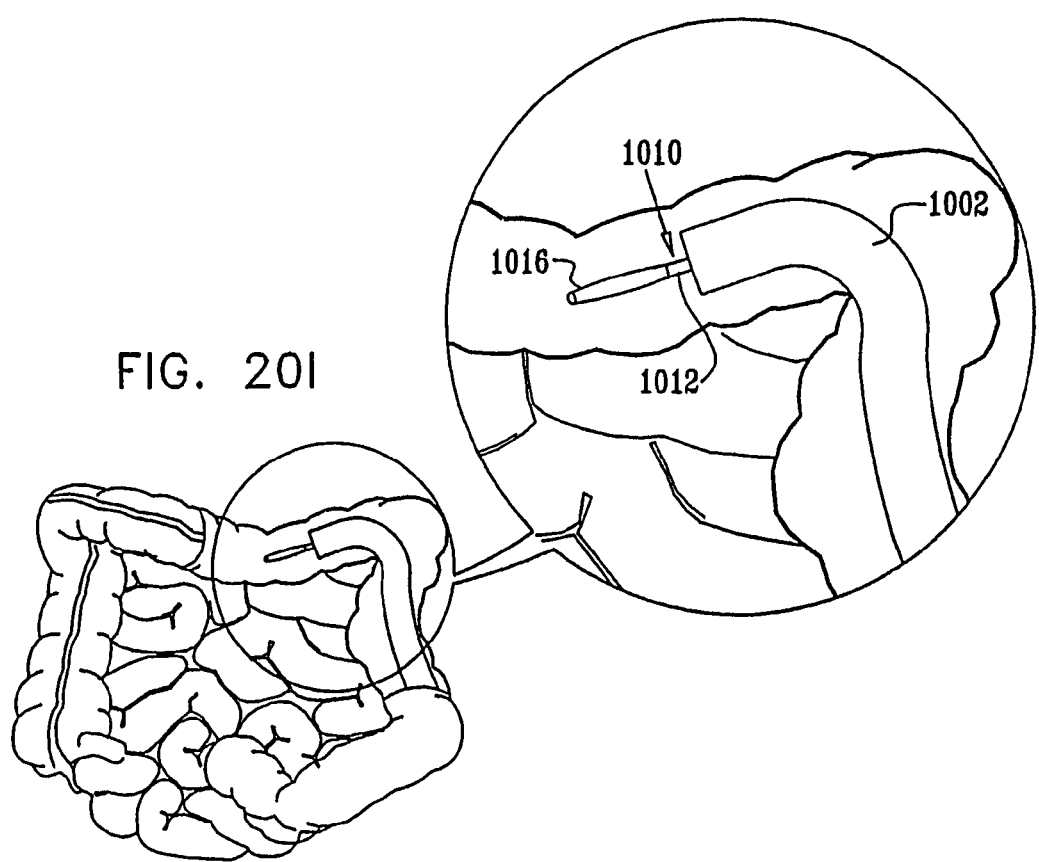

FIG. 20H shows the endoscope 1002 having been pushed forward along the multi-lumen tube 1012, using the multi-lumen tube as a sort of guide wire. Endoscope 1002 may be pushed forward in a conventional manner. Thereafter, as shown in FIG. 19, the balloon 1016 may be deflated.

Further forward progress of the endoscope through the intestine, preferably to a position where the forward end of the instrument channel 1011 lies just behind the balloon 1016, similarly to the orientation shown in FIG. 20A, may be achieved by repeating some or all of the steps described hereinabove with reference to FIGS. 20A-20I, as required by the geometries encountered.

Reference is now made to FIGS. 21-23B, which are respectively a simplified pictorial illustration of an endoscopy system constructed and operative in accordance with another preferred embodiment of the present invention and respective simplified pictorial and sectional view illustrations of an accessory constructed and operative in accordance with a preferred embodiment of the present invention.

As seen in FIGS. 21-23B a conventional endoscopy system 1300, such as a console including a CV-160 video system center, a CLC-160 light source, an OEV-203 video monitor, and an OFP flushing pump, all commercially available from Olympus America Inc. of 2 Corporate Center Drive, Melville, N.Y. 11747, USA, is being employed. A conventional endoscope 1302, which forms part of conventional endoscopy system 1300 may be employed, such as a CF-Q160AL video colonoscope which is commercially available from Olympus America Inc. of 2 Corporate Center Drive, Melville, N.Y. 11747, USA. In accordance with a preferred embodiment of the invention, a peripheral balloon 1304 may be mounted onto endoscope 1302 as shown. Preferably inflation and deflation of peripheral balloon 1304 may be provided by a tube 1306 communicating with the interior thereof.

An endoscope tool 1310, constructed and operative in accordance with a preferred embodiment of the present invention extends through the instrument channel 1311 of the conventional endoscope 1302. Endoscope tool 1310 is characterized in that it includes a multi-lumen tube 1312 which includes at least a first lumen 1314 for inflation and deflation of a balloon 1316 via an inflation aperture 1317, and a second lumen 1318. Preferably the second lumen 1318 may accommodate a tensioning or compression wire 1320. Alternatively or additionally, the second lumen 1318 may have other functionality. As a further alternative, the multi-lumen tube 1312 forming part of the endoscope tool 1310 may include more than two lumens. Preferably, the cross-sectional area of the multi-lumen tube 1312 is sufficiently less than that of the instrument channel 1311, so as to allow supply of fluid for inssuflation and draining of fluid therethrough.

It is appreciated that in accordance with a preferred embodiment of the present invention the endoscope tool 1310 and the multi-lumen tube 1312 are generally substantially more flexible than endoscope 1302 and an endoscope tube thereof.

It is appreciated that in accordance with a preferred embodiment of the present invention the balloon 1316 is generally stretchable, and can be stretched to a diameter about 5-20 times larger than its diameter when not inflated. In a specific embodiment, useful for small intestine endoscopy, the balloon diameter when fully stretched is four centimeters. Preferably, inflation of the balloon 1316 to a diameter less than four centimeters may be achieved using relatively low pressure, such as in the range of 10-50 milibars. In another specific embodiment, useful for large intestine endoscopy, the balloon diameter when fully stretched is seven centimeters. Preferably, inflation of the balloon 1316 to a diameter less than seven centimeters may be achieved using relatively low pressure, such as in the range of 10-50 milibars.

It is appreciated that in accordance with a preferred embodiment of the present invention useful for in vivo inspection of a generally tubular body portion having a variable cross-sectional diameter, the expansion diameter range of balloon 1316 is larger than the maximum cross-sectional diameter of the generally tubular body portion, thereby ensuring engagement of expanded balloon 1316 with the interior surface of the generally tubular body portion, and anchoring of the endoscope tool 1310 thereto. Preferably, balloon 1316 is a relatively soft, highly compliant balloon, operative to at least partially conform to the shape of the interior surface of the generally tubular body portion when in engagement therewith.

It is appreciated that balloon 1316 may be formed of well-known stretchable materials such as latex, flexible silicon, or highly flexible nylon. Alternatively, balloon 1316 may be formed of polyurethane, which is less stretchable and conforming than latex, flexible silicon or highly flexible nylon. Preferably, the diameter of balloon 1316 is sufficient to ensure tight anchoring at any part of the generally tubular body portion.

As seen in FIGS. 21-23B, the endoscope tool 1310 preferably includes a tool positioning control device 1324 and a balloon inflation/deflation control interface 1326. Additionally, there is preferably provided a peripheral balloon inflation/deflation control interface 1328, which communicates with tube 1306 and governs inflation and deflation of peripheral balloon 1304. It is appreciated that multi-lumen tube 1312 and the entire endoscope tool 1310 may be inserted and removed via a conventional tool port 1330 on a conventional operator control 1332 which forms part of conventional endoscope 1302.

Reference is now made to FIGS. 24A, 24B, 24C, 24D, 24E, 24F, 24G, 24H, 24I, 24J, 24K and 24L, which are simplified illustrations of the endoscope tool 1310 of FIGS. 21-23B in various operative orientations. In the illustrated embodiment, desired directional orientation of the forward end of the endoscope tool 1310 is obtained by suitable axial displacement of the tool through the instrument channel 1311 of the endoscope 1302 combined with suitable tensioning of wire 1320 and with suitable rotational orientation of the endoscope tool 1310 relative to the intestine.

Figure 24A:
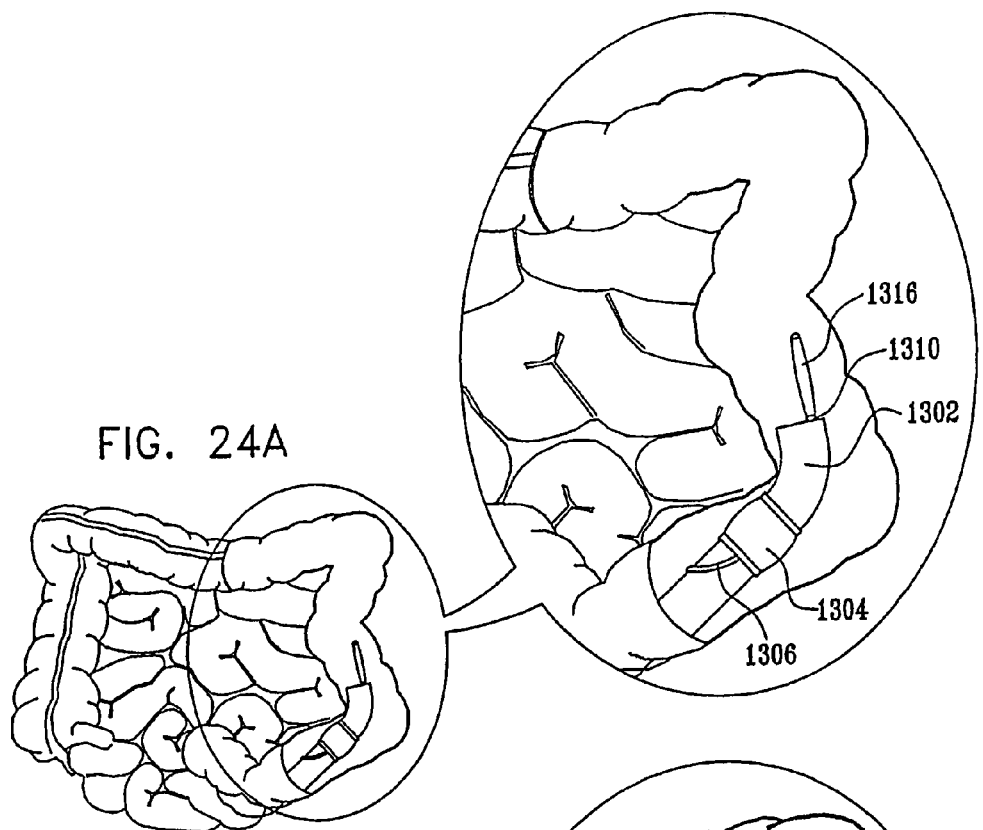
FIGS. 24A, 24B, 24C, 24D, 24E, 24F, 24G, 24H, 24I, 24J, 24K and 24L are simplified illustrations of various functionalities which may be provided by the system of FIG. 21.

As seen in FIG. 24A, endoscope tool 1310 is principally located within the instrument channel 1311 of endoscope 1302, and has balloon 1316 protruding therefrom, while in a deflated state. As seen, peripheral balloon 1304 is in a deflated state.

Figure 24B:
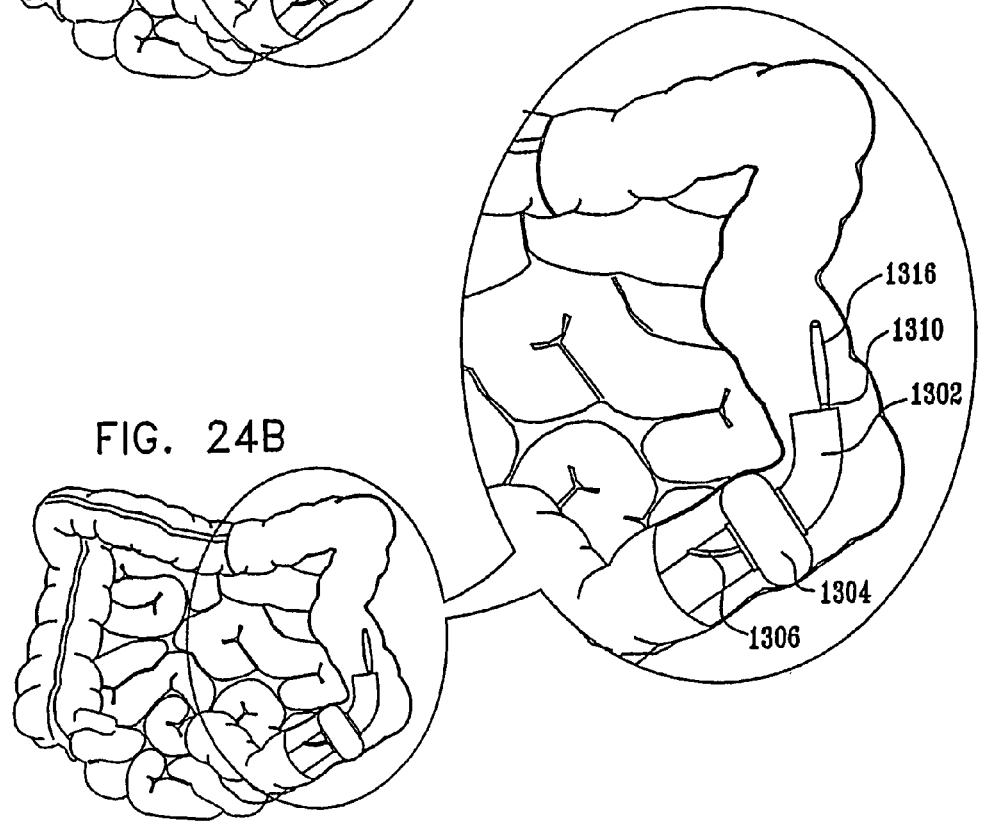

FIG. 24B shows endoscope tool 1310 being principally located within the instrument channel 1311 of endoscope 1302, and has balloon 1316 protruding therefrom, while in a deflated state. As seen, peripheral balloon 1304 is in an inflated state in engagement with an interior wall of the intestine, thereby anchoring the endoscope 1302 thereat.

Figure 24C:
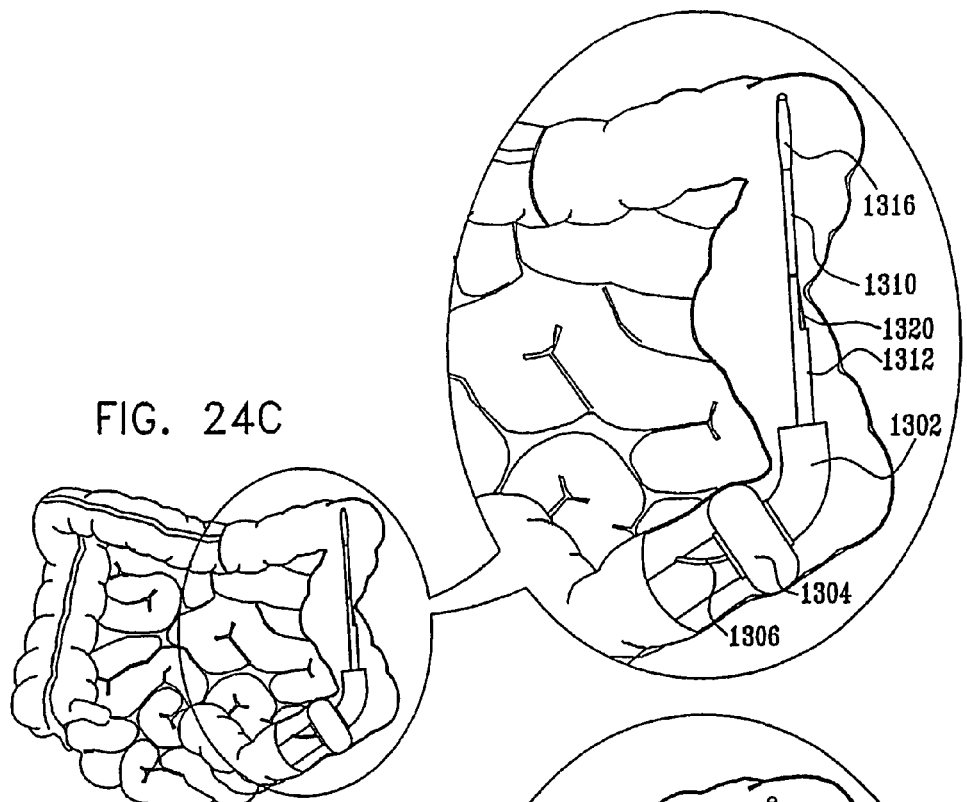
Figure 24D:
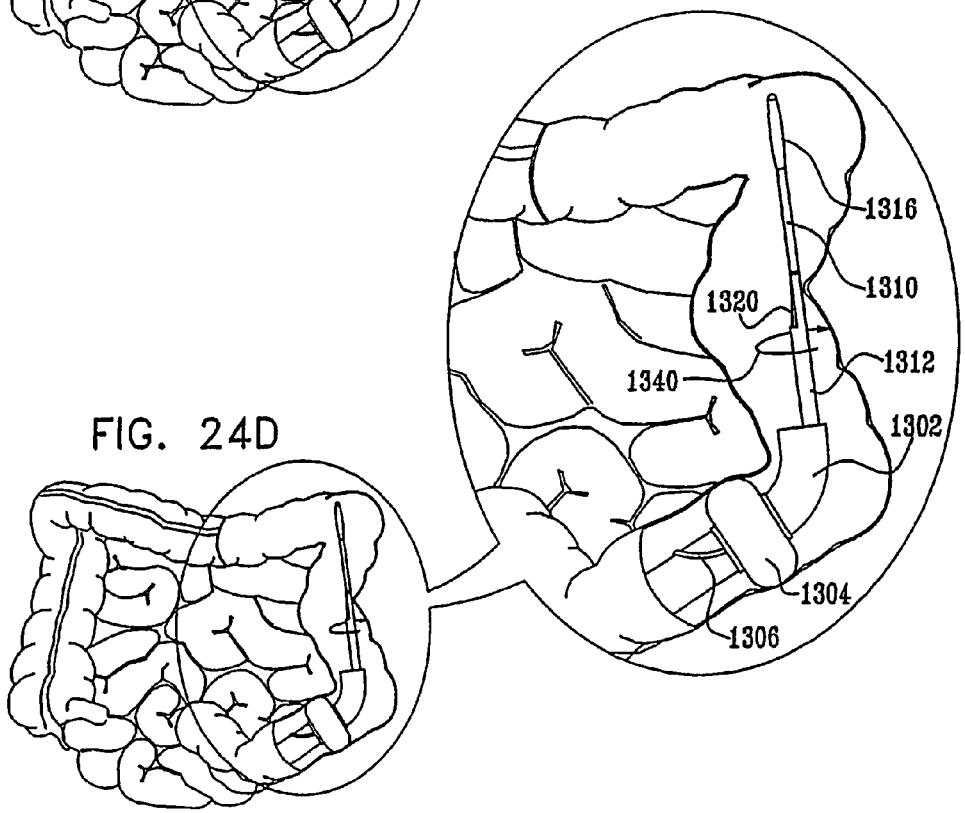

FIG. 24C shows the endoscope tool 1310 extending further from the instrument channel 1311, while FIG. 24D shows the endoscope tool 1310 having been rotated by 180 degrees relative to its orientation in FIG. 24C, by suitable twisting of multi-lumen tube 1312, as indicated by arrow 1340.

Figures 24E, 24F:
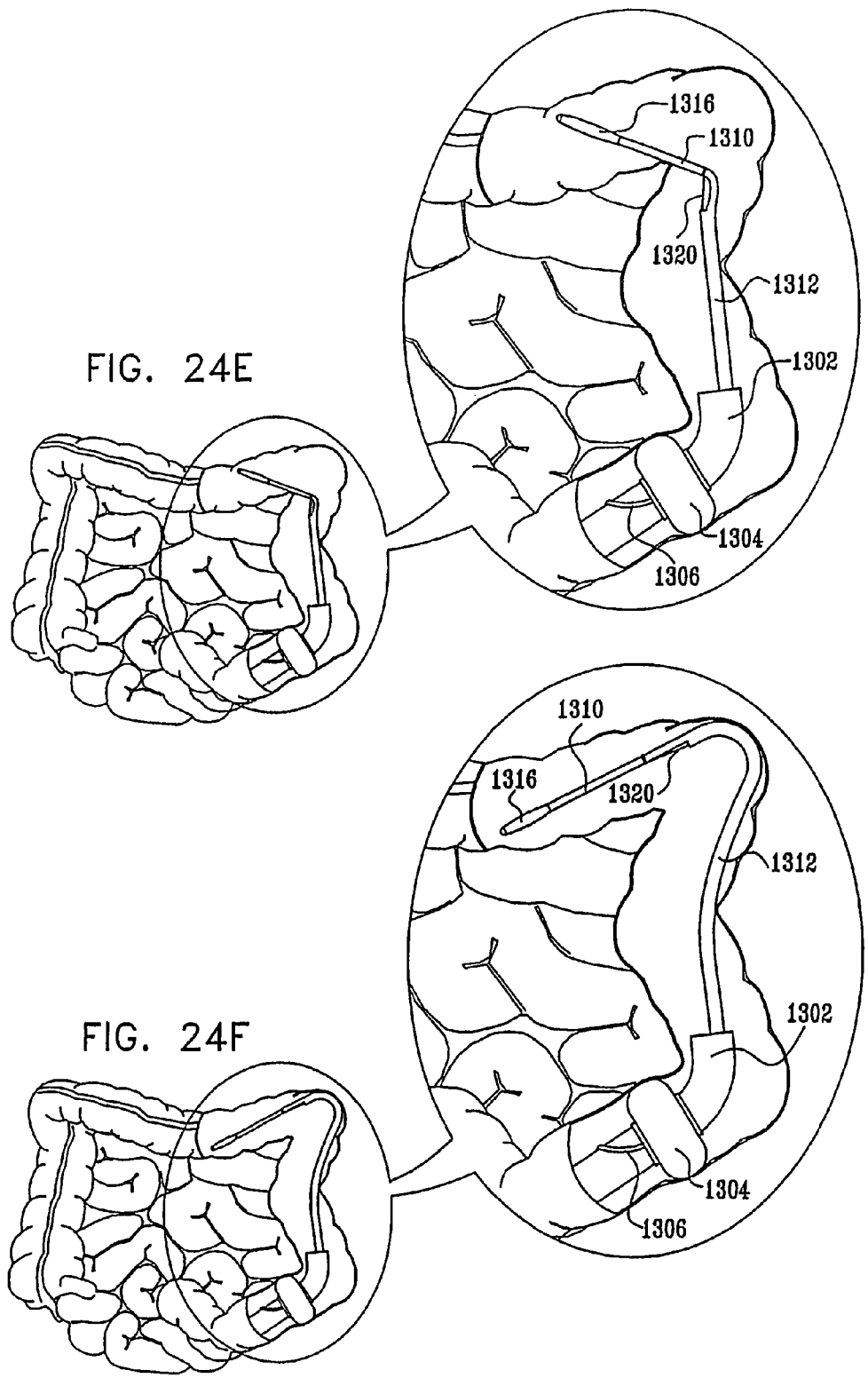

FIG. 24E shows bending of the forward end of the endoscope tool 1310 resulting from tensioning of wire 1320, when the tool is in its FIG. 24D orientation having been pushed forward in a conventional manner.

FIG. 24F shows further progress of the endoscope tool 1310 through the intestine resulting from forward pushing of the tool coupled with release the tension on the wire 1320 by operation of tool positioning control device 1324.

Figure 24G:
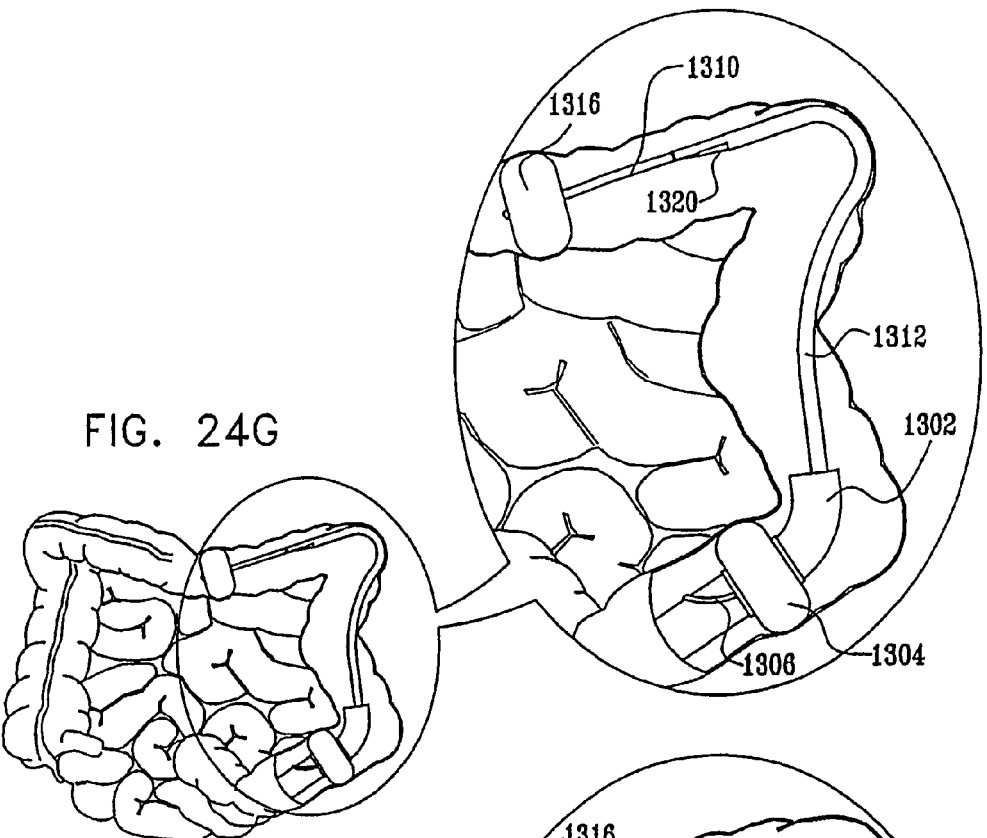

FIG. 24G shows inflation of the balloon 1316 by operation of the balloon inflation/deflation control interface 1326. In accordance with a preferred embodiment of the invention, this inflation anchors the forward end of the endoscope tool 1310 to the intestine at the location of the balloon 1316.

Figure 24H:
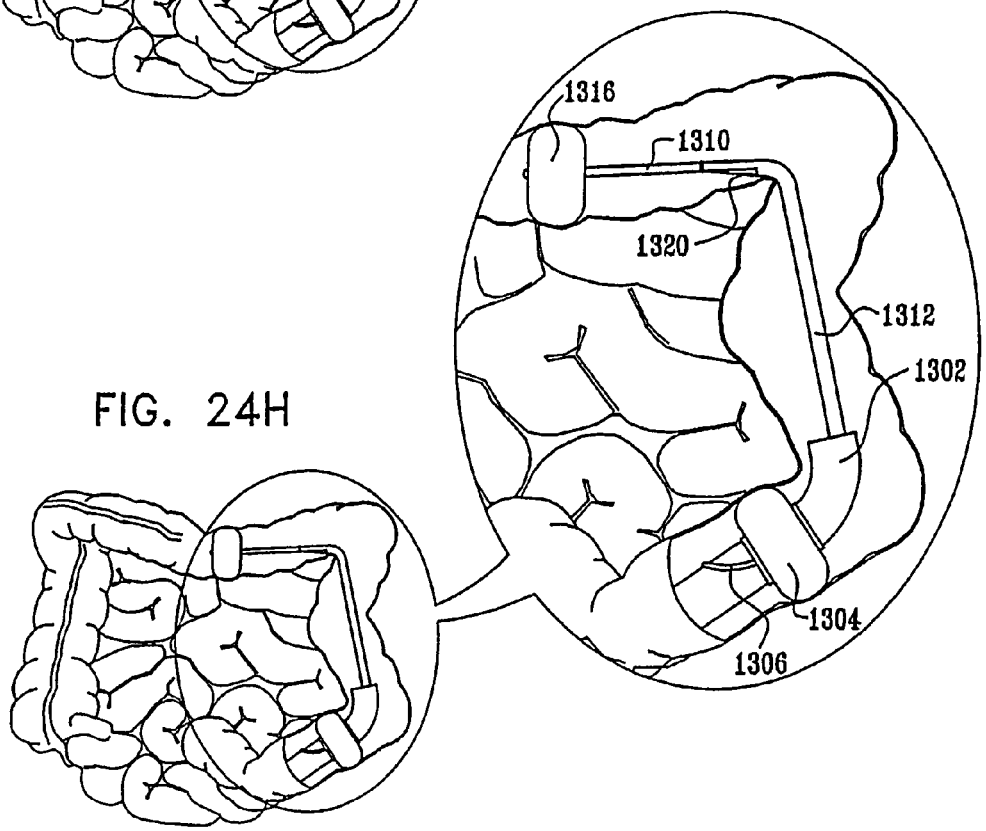

FIG. 24H shows tensioning of the endoscope tool 1310 including the multi-lumen tube 1312 by pulling on the multi-lumen tube 1312.

Figure 24I:
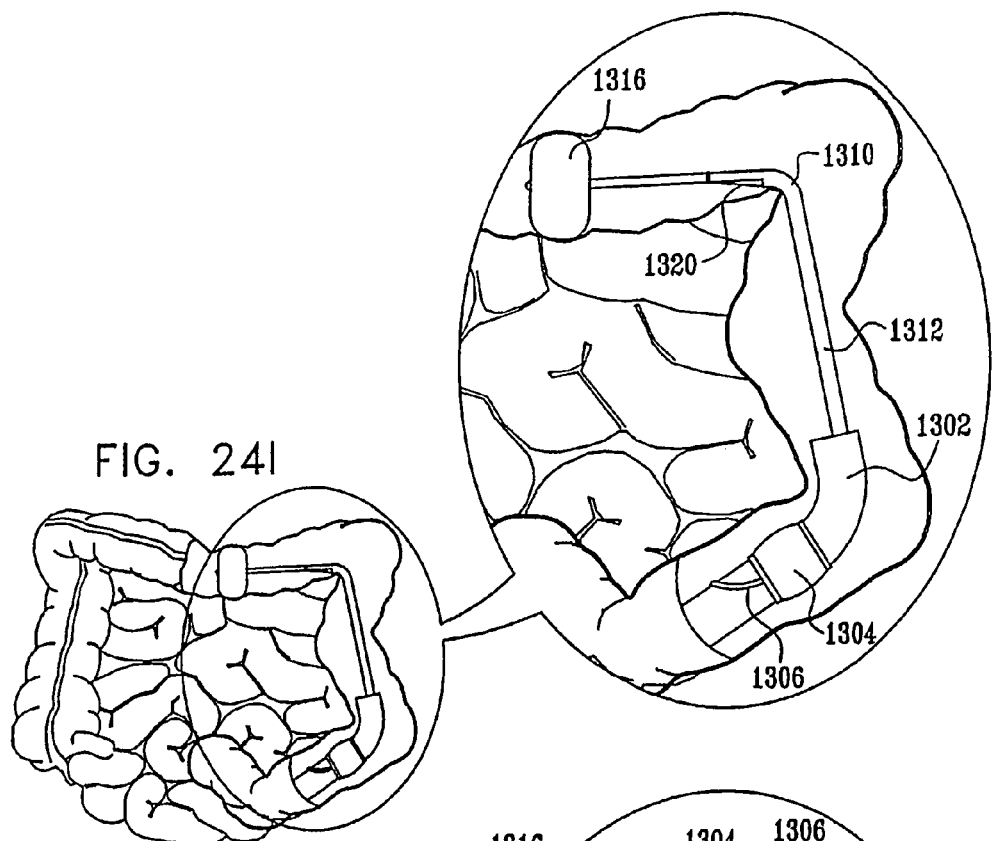

FIG. 24I shows deflation of peripheral balloon 1304.

Figure 24J:
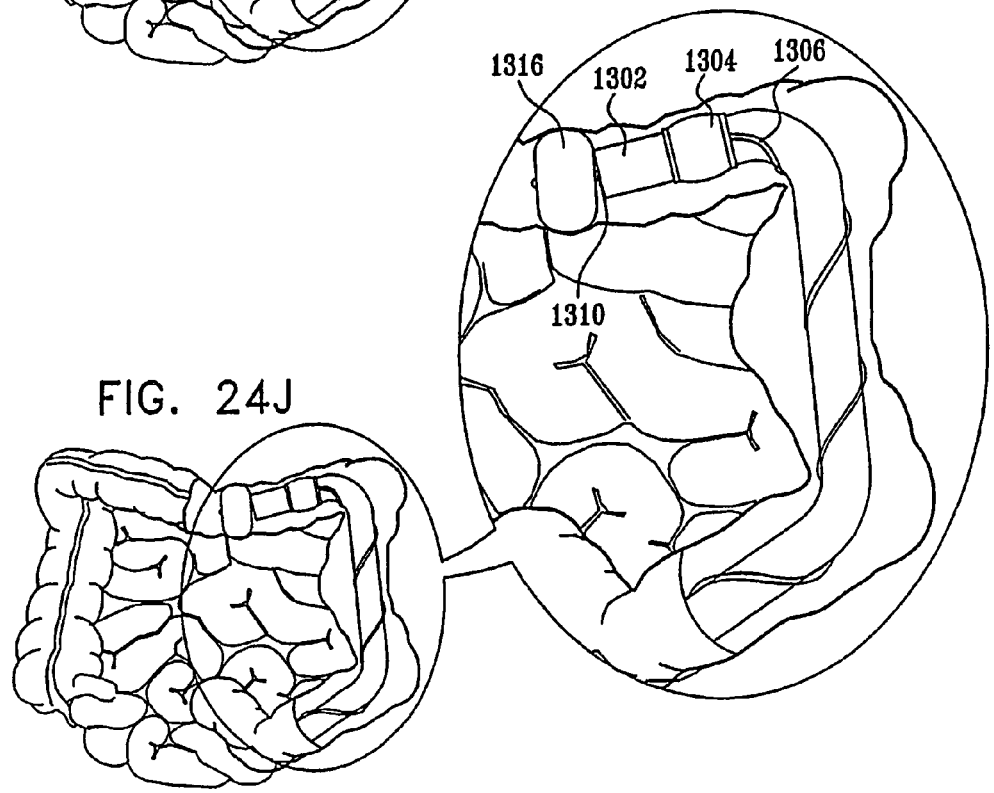

FIG. 24J shows the endoscope 1302 having been pushed forward along the multi-lumen tube 1312, using the multi-lumen tube as a sort of guide wire. Endoscope 1302 may be pushed forward in a conventional manner.

Figure 24K:
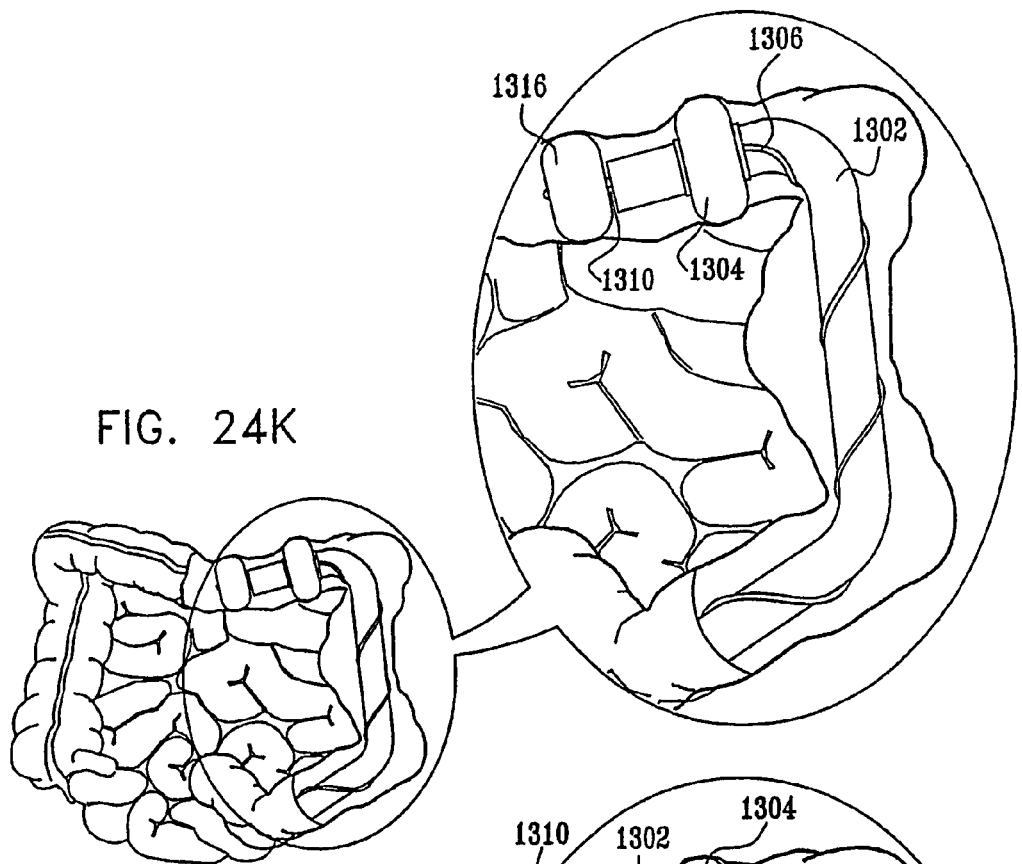

FIG. 24K shows inflation of peripheral balloon 1304 into engagement with an interior wall of the intestine, thereby anchoring the endoscope 1302 thereat.

Figure 24L:
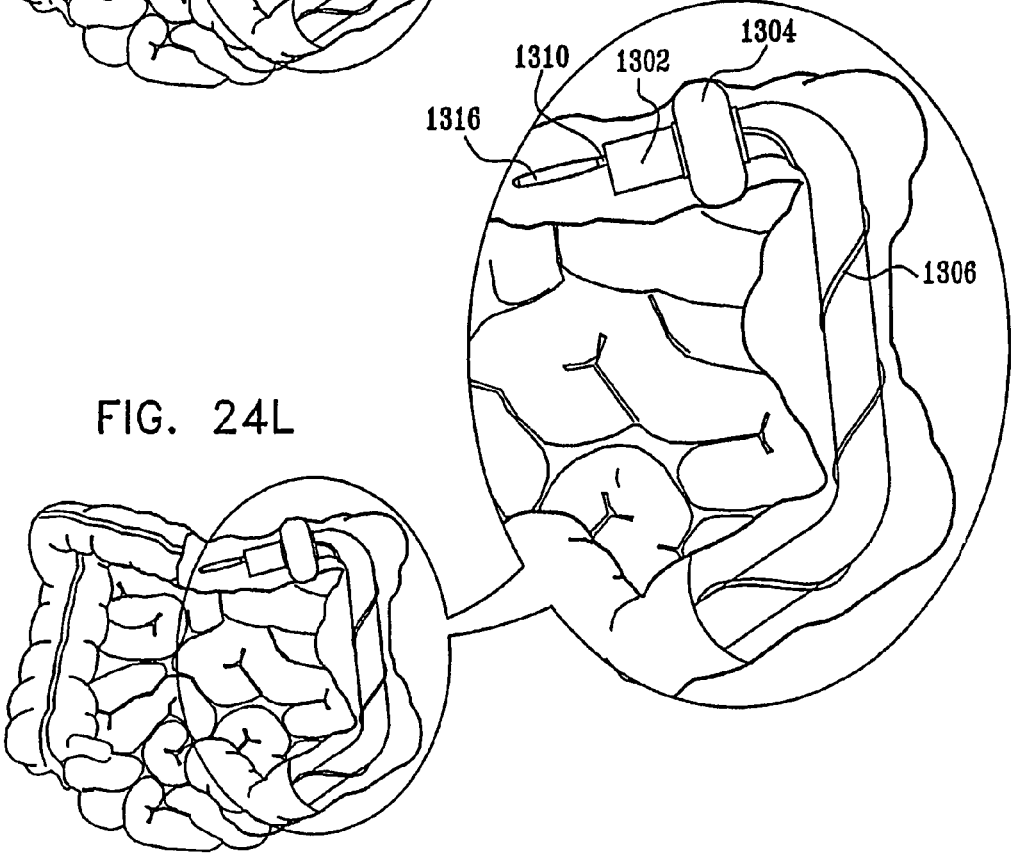

Thereafter, as shown in FIG. 24L, the balloon 1316 may be deflated.

Further forward progress of the endoscope through the intestine, preferably to a position where the forward end of the instrument channel 1311 lies just behind the balloon 1316, similarly to the orientation shown in FIG. 24B, may be achieved by repeating some or all of the steps described hereinabove with reference to FIGS. 24B-24L, as required by the geometries encountered.

It will be appreciated by persons skilled in the art that the present invention is not limited to what has been particularly shown and described hereinabove. Rather the scope of the present invention includes both combinations and subcombinations of various features described hereinabove as well as modifications thereof which would occur to persons skilled in the art upon reading the foregoing specification and which are not in the prior art.

The invention claimed is:

1. A locomotive endoscope assembly for fluid supply to the interior of a portion of a tubular body portion comprising:
   an endoscope body;
   a locomotive endoscope head, adapted to allow pulling of the endoscope body through said tubular body portion, which is arranged at a distal end of said endoscope body, extends along a longitudinal axis and has a first selectably radially extendible sealing element and a second selectably radially extendible sealing element located distal to the first selectably radially extendible sealing element, wherein at least one of said first and second selectably radially extendible sealing elements is axially displaceable along the longitudinal axis with respect to the other, the distance between a proximal end of the first selectably radially extendible sealing element and a distal end of the locomotive endoscope head being fixed;
   the distal end of the locomotive endoscope head comprising one or more imaging sensors and a light source;
   a fluid passageway adapted for supplying fluid at a region radially outward of said locomotive endoscope head and intermediate said first and second selectably radially extendible sealing elements when said selectably radially extendible sealing elements are in radially extended sealing engagement with said tubular body portion; and
   a locomotive endoscope head controller controlling the operation of the locomotive endoscope head and being operative for controlling selectable extension of said first and second selectably radially extendible sealing elements, axial displacement of said at least one of said first and second selectably radially extendible sealing elements and fluid introduction through said fluid passageway.

2. A locomotive endoscope assembly for fluid supply according to claim 1 and wherein at least one of said first and second selectably radially extendible sealing elements comprises a selectably inflatable balloon.

3. A locomotive endoscope assembly for fluid supply according to claim 1 and also comprising an instrument channel at least partially extending through said locomotive endoscope head and said endoscope body.

4. A locomotive endoscope assembly for fluid supply according to claim 1 and wherein said locomotive endoscope head controller provides locomotive functionality adapted to sequentially displace said locomotive endoscope head through a generally tubular body portion.

* * * * *

UNITED STATES PATENT AND TRADEMARK OFFICE
CERTIFICATE OF CORRECTION

| | | |
|---|---|---|
| PATENT NO. | : 7,963,911 B2 | Page 1 of 1 |
| APPLICATION NO. | : 11/980025 | |
| DATED | : June 21, 2011 | |
| INVENTOR(S) | : Gad Terliuc | |

It is certified that error appears in the above-identified patent and that said Letters Patent is hereby corrected as shown below:

ON THE TITLE PAGE:

Item (75) Inventor:
Please delete inventor "Gad Turliuc"; please insert --Gad Terliuc--.

Signed and Sealed this
Sixth Day of March, 2012

David J. Kappos
*Director of the United States Patent and Trademark Office*